(12) United States Patent
Russell et al.

(10) Patent No.: US 11,213,303 B2
(45) Date of Patent: Jan. 4, 2022

(54) BONE DRILL GUIDES AND METHODS OF USE THEREOF

(71) Applicant: Innovision, Inc., Memphis, TN (US)

(72) Inventors: Thomas A Russell, Memphis, TN (US); Todd A Glover, Memphis, TN (US)

(73) Assignee: Innovision, Inc., Memphis, TN (US)

( * ) Notice: Subject to any disclaimer, the term of this patent is extended or adjusted under 35 U.S.C. 154(b) by 275 days.

(21) Appl. No.: 16/416,932

(22) Filed: May 20, 2019

(65) Prior Publication Data
US 2019/0290298 A1 Sep. 26, 2019

Related U.S. Application Data

(63) Continuation of application No. 14/849,184, filed on Sep. 9, 2015, now Pat. No. 10,413,306.

(30) Foreign Application Priority Data

Sep. 12, 2014 (WO) ............... PCT/US2014/055497

(51) Int. Cl.
*A61B 17/17* (2006.01)
*A61B 17/88* (2006.01)
(Continued)

(52) U.S. Cl.
CPC ...... *A61B 17/1721* (2013.01); *A61B 17/8897* (2013.01); *A61B 17/742* (2013.01); *A61B 17/848* (2013.01); *A61B 17/863* (2013.01)

(58) Field of Classification Search
CPC ............. A61B 17/864; A61B 17/1721; A61B 17/1725; A61B 17/1728; A61B 17/1742; A61B 17/7098
See application file for complete search history.

(56) References Cited

U.S. PATENT DOCUMENTS 2,200,120 A * 5/1940 Nauth ................ A61B 17/1703
606/97
2,531,734 A * 11/1950 Hopkins ............ A61B 17/1721
606/97
(Continued)

FOREIGN PATENT DOCUMENTS

CN 1889889 A 1/2007
CN 102341052 A 2/2012
(Continued)

OTHER PUBLICATIONS

"U.S. Appl. No. 14/849,184, Final Office Action dated Jun. 13, 2018", 13 pgs.
(Continued)

*Primary Examiner* — Matthew J Lawson
(74) *Attorney, Agent, or Firm* — Schwegman Lundberg & Woessner, P.A.

(57) ABSTRACT

The invention features bone drill guides, sleeves, and methods of use thereof in inserting hardware into bones, in particular to repair bone defects. The bone drill guides are designed to seat firmly against bone while allowing translational, rotational, and angular movement during an operation. The bone drill guides also allow for insertion of multiple devices, such as guide wires, into bone at defined and constrained relative position.

19 Claims, 36 Drawing Sheets

(51) Int. Cl.
*A61B 17/74* (2006.01)
*A61B 17/86* (2006.01)
*A61B 17/84* (2006.01)

(56) References Cited

U.S. PATENT DOCUMENTS

| | | | | |
|---|---|---|---|---|
| 2,607,339 | A * | 8/1952 | Price | A61B 17/1703 |
| | | | | 606/96 |
| 3,727,611 | A | 4/1973 | Schultz | |
| 4,364,381 | A | 12/1982 | Sher | |
| 4,383,527 | A | 5/1983 | Asnis | |
| 4,450,835 | A * | 5/1984 | Asnis | A61B 17/1721 |
| | | | | 606/65 |
| 4,465,065 | A * | 8/1984 | Gotfried | A61B 17/1721 |
| | | | | 606/65 |
| 4,653,489 | A * | 3/1987 | Tronzo | A61B 17/746 |
| | | | | 606/304 |
| 4,917,604 | A * | 4/1990 | Small | A61C 1/084 |
| | | | | 433/173 |
| 5,324,295 | A * | 6/1994 | Shapiro | A61B 17/1714 |
| | | | | 606/86 R |
| 5,429,641 | A * | 7/1995 | Gotfried | A61B 17/746 |
| | | | | 606/67 |
| 6,066,142 | A | 5/2000 | Serbousek et al. | |
| 6,231,611 | B1 | 5/2001 | Mosseri | |
| 6,869,283 | B2 | 3/2005 | Sussman | |
| 7,153,309 | B2 * | 12/2006 | Huebner | A61B 17/1728 |
| | | | | 606/96 |
| 7,727,236 | B2 | 6/2010 | Choe et al. | |
| 8,080,045 | B2 | 12/2011 | Wotton, III | |
| 8,696,680 | B2 | 4/2014 | Iannotti et al. | |
| 9,681,904 | B2 * | 6/2017 | Wolf | A61B 17/808 |
| 9,814,453 | B2 | 11/2017 | Bonutti et al. | |
| 10,413,306 | B2 | 9/2019 | Russell et al. | |
| 2003/0208122 | A1 | 11/2003 | Melkent et al. | |
| 2005/0027301 | A1 | 2/2005 | Stihl | |
| 2006/0098851 | A1 | 5/2006 | Shoham et al. | |
| 2011/0166573 | A1 | 7/2011 | Wenk et al. | |
| 2012/0209334 | A1 | 8/2012 | Lewis et al. | |
| 2014/0074174 | A1 | 3/2014 | Schacherer et al. | |
| 2015/0066041 | A1 * | 3/2015 | Kim | A61B 17/1721 |
| | | | | 606/96 |
| 2015/0080967 | A1 | 3/2015 | Dasilva | |
| 2016/0074049 | A1 | 3/2016 | Russell et al. | |

FOREIGN PATENT DOCUMENTS

| | | | |
|---|---|---|---|
| CN | 202761428 U | 3/2013 | |
| CN | 107835665 A | 3/2018 | |
| GB | 1448111 * | 1/1973 | ......... A61B 17/1721 |
| GB | 2442441 A | 4/2008 | |
| JP | 2002034999 A | 2/2002 | |
| JP | 2007501670 A | 2/2007 | |
| JP | 2010505488 A | 2/2010 | |
| JP | 2017527430 A | 9/2017 | |
| WO | WO-2016039775 A1 | 3/2016 | |

OTHER PUBLICATIONS

"U.S. Appl. No. 14/849,184, Non Final Office Action dated Feb. 15, 2018", 13 pgs.
"U.S. Appl. No. 14/849,184, Non Final Office Action dated Dec. 3, 2018", 11 pgs.
"U.S. Appl. No. 14/849,184, Notice of Allowance dated Apr. 2, 2019", 6 pgs.
"U.S. Appl. No. 14/849,184, Response filed Jan. 9, 2018 to Restriction Requirement dated Dec. 26, 2017", 9 pgs.
"U.S. Appl. No. 14/849,184, Response filed Jan. 18, 2019 to Non Final Office Action dated Dec. 3, 2018", 13 pgs.
"U.S. Appl. No. 14/849,184, Response filed May 16, 2018 to Non Final Office Action dated Feb. 15, 2018", 15 pgs.
"U.S. Appl. No. 14/849,184, Response filed Sep. 5, 2018 to Final Office Action dated Jun. 13, 2018", 13 pgs.
"U.S. Appl. No. 14/849,184, Restriction Requirement dated Dec. 26, 2017", 8 pgs.
"Australian Application Serial No. 2014405942, First Examination Report dated Jan. 7, 2019", 4 pgs.
"Canadian Application Serial No. 2,960,373, Office Action dated Feb. 11, 2019", 3 pgs.
"European Application Serial No. 14901686.7, Extended European Search Report dated Jan. 18, 2018", 7 pgs.
"European Application Serial No. 14901686.7, Response filed Aug. 16, 18 to Extended European Search Report dated Jan. 18, 2018", 13 pgs.
"European Application Serial No. 14901686.7, Response filed Nov. 22, 2017 to Communication pursuant to Rules 161(1) and 162 EPC dated May 12, 2017", 13 pgs.
"International Application Serial No. PCT/US2014/055497, International Preliminary Report on Patentability dated Mar. 23, 2017", 7 pgs.
"International Application Serial No. PCT/US2014/055497, International Search Report dated Jan. 2, 2015", 3 pgs.
"International Application Serial No. PCT/US2014/055497, Written Opinion dated Jan. 2, 2015", 5 pgs.
"Japanese Application Serial No. 2017-534516, Office Action dated Jun. 26, 2018", (W/ English Translation), 8 pgs.
"Japanese Application Serial No. 2017-534516, Response filed Sep. 14, 2018 to Office Action dated Jun. 26, 2018", (W/ English Translation of Claims), 14 pgs.
"U.S. Appl. No. 14/849,184, Notice of Allowability dated May 24, 2019", 3 pgs.
"Canadian Application Serial No. 2,960,373, Response filed Aug. 6, 2019 to Office Action dated Feb. 11, 2019", 3 pgs.
"Chinese Application Serial No. 201480083051.3, Office Action dated Jul. 10, 2020", (W/ English Translation), 9 pgs.
"Chinese Application Serial No. 201480083051.3, Office Action dated Oct. 30, 2019", (W/ English Translation), 19 pgs.
"Chinese Application Serial No. 201480083051.3, Response filed Mar. 2, 2020 to Office Action dated Oct. 30, 2019", (W/ English Translation of Claims), 17 pgs.
"Chinese Application Serial No. 201480083051.3, Response filed Sep. 4, 2020 to Office Action dated Jul. 10, 2020", (W/ English Translation of Claims), 13 pgs.

* cited by examiner

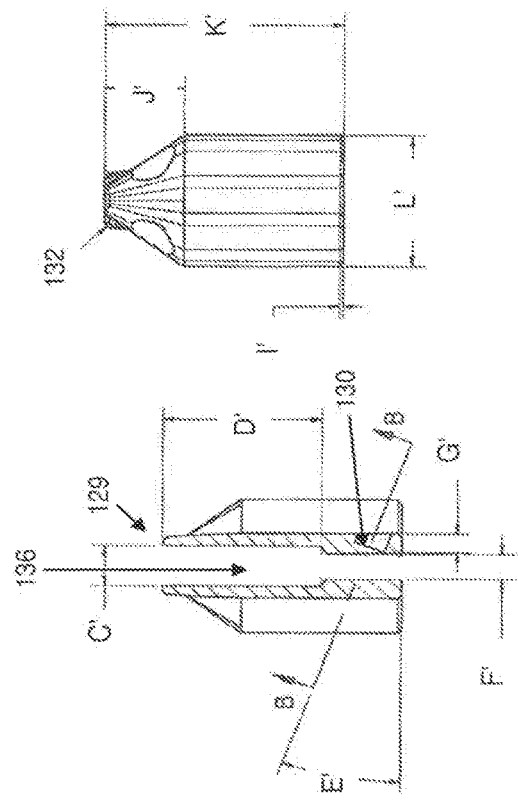
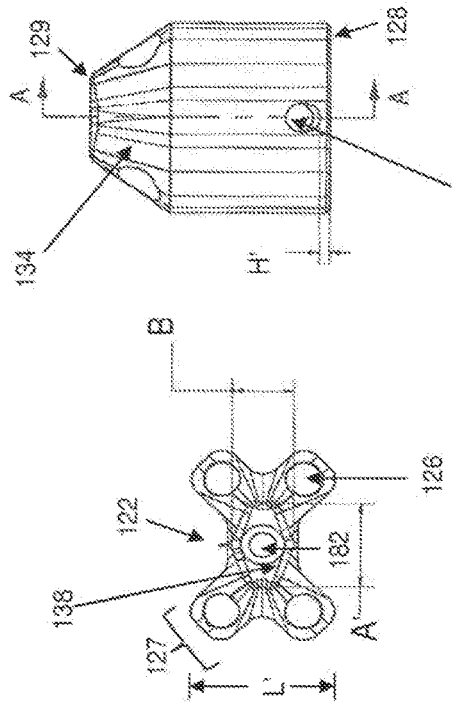
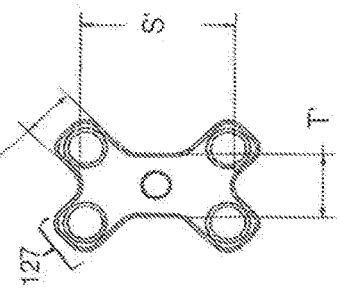
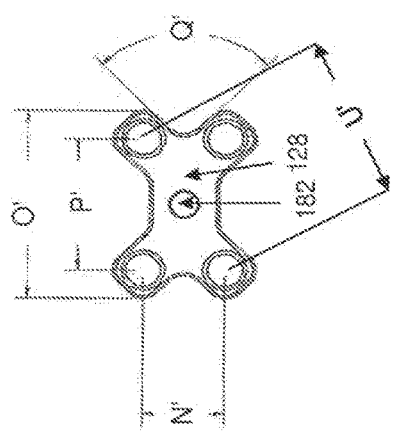
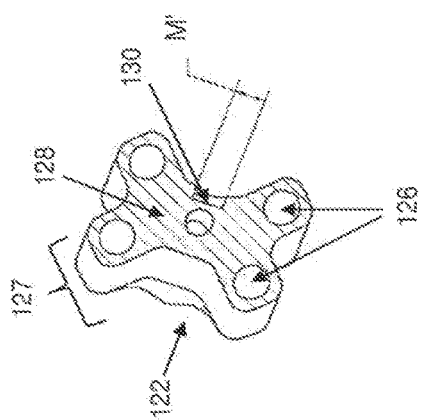

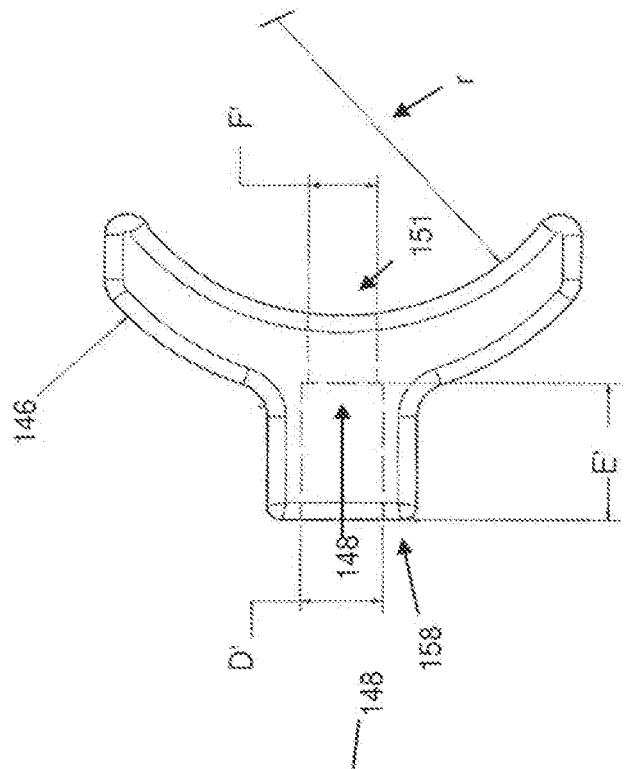
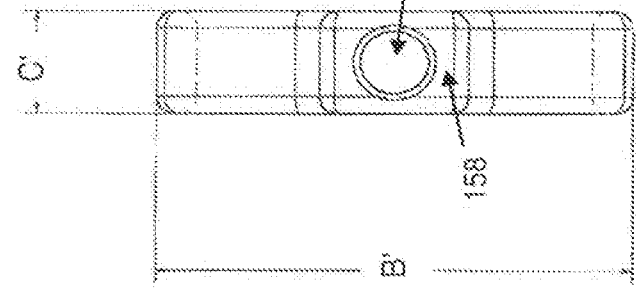
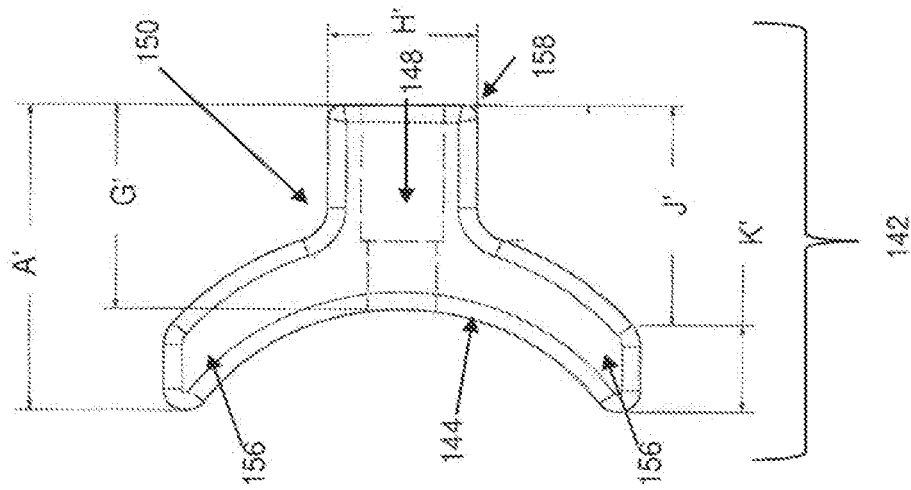

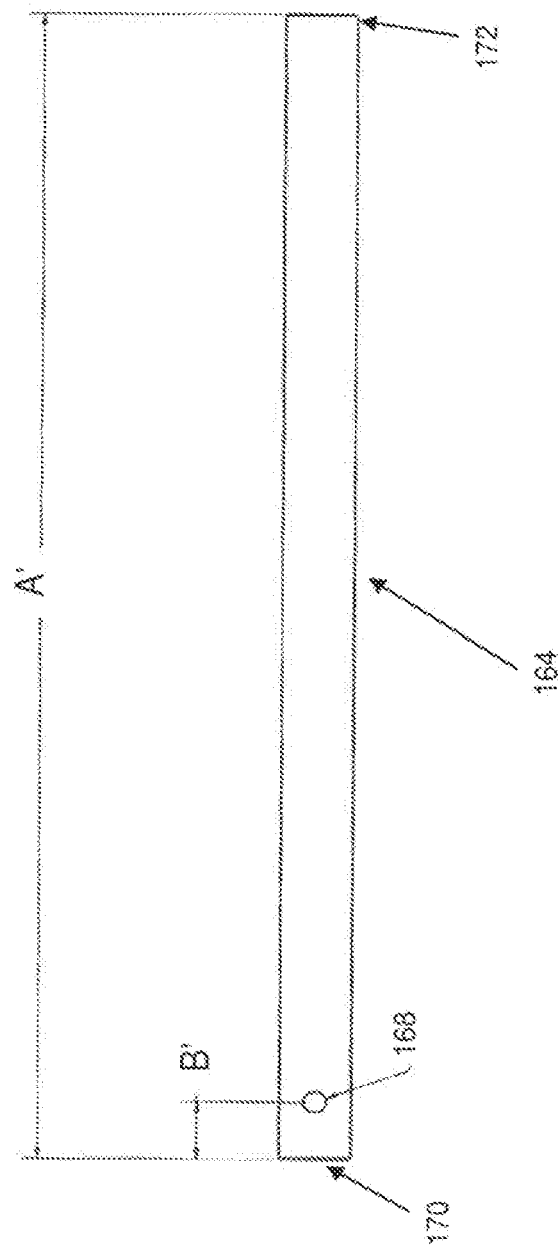

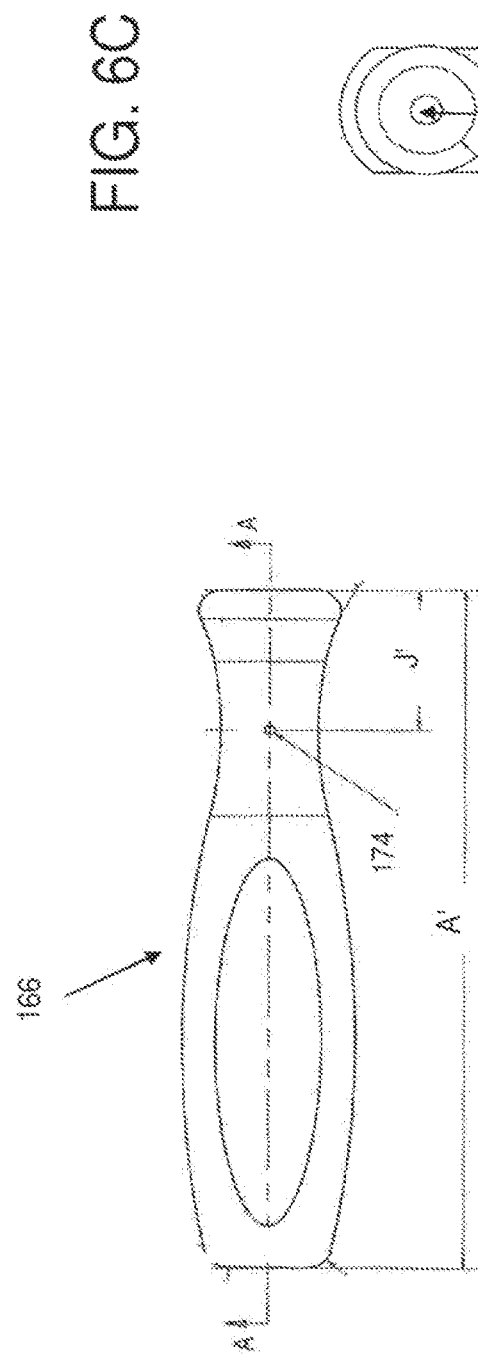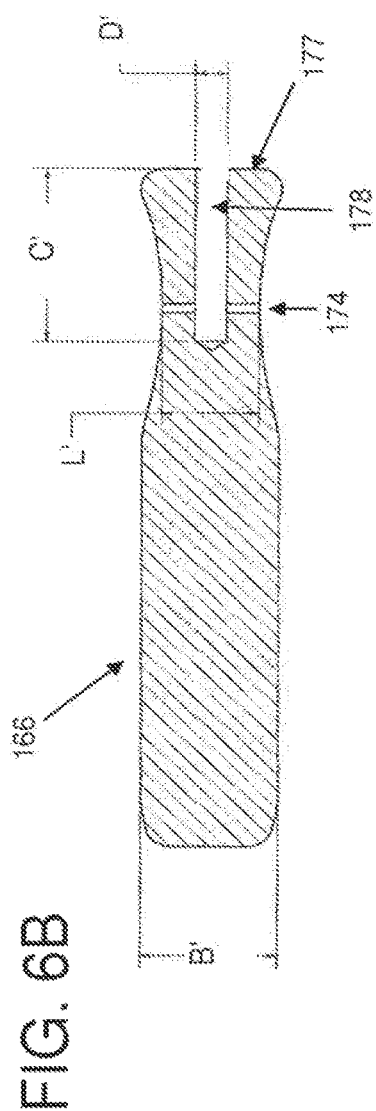

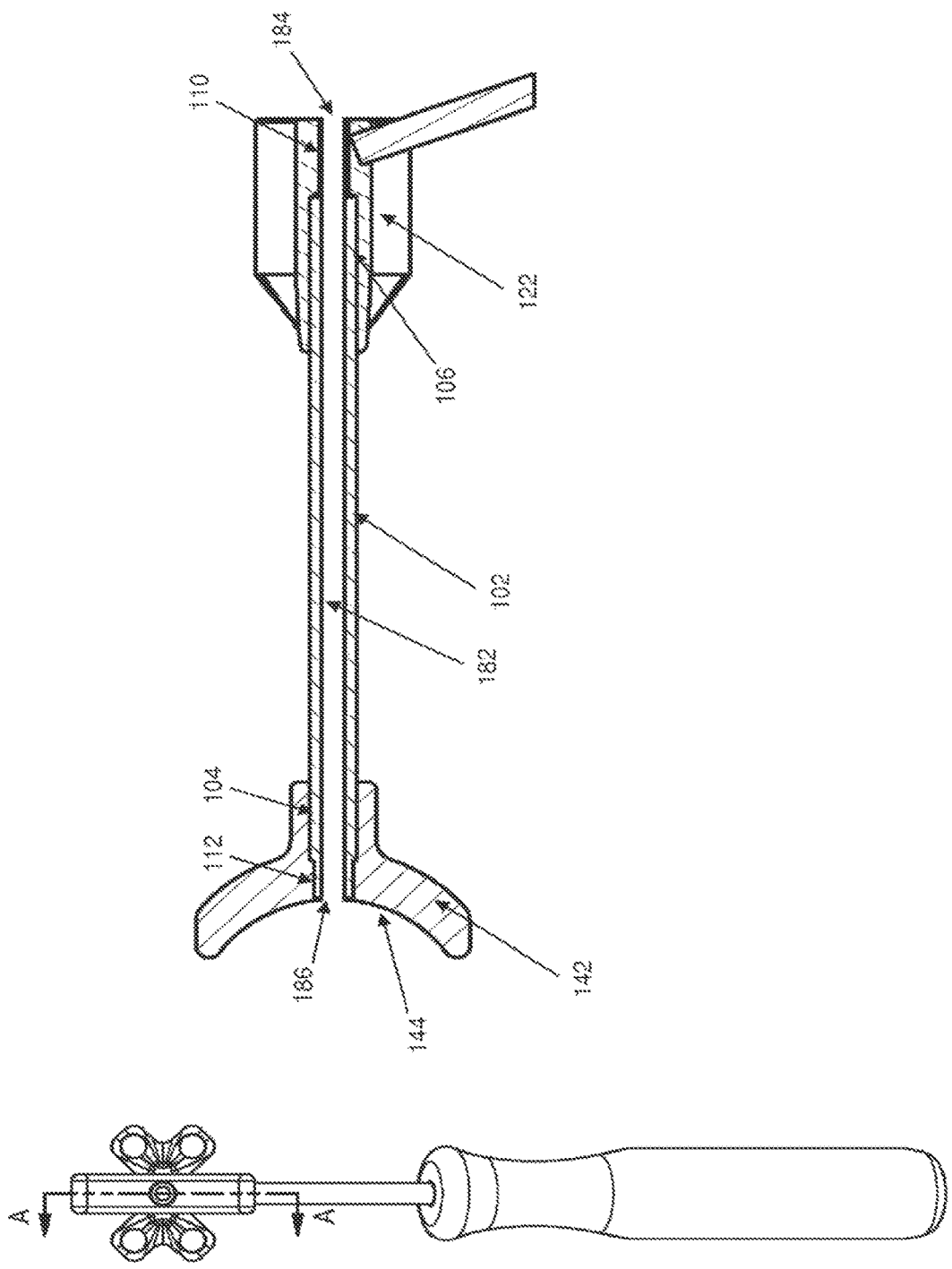

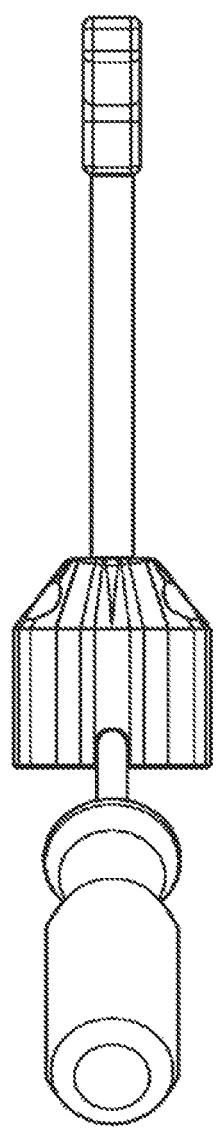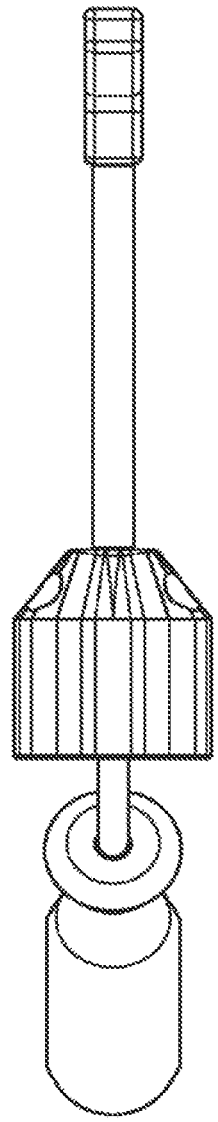
FIG. 8A
FIG. 8B

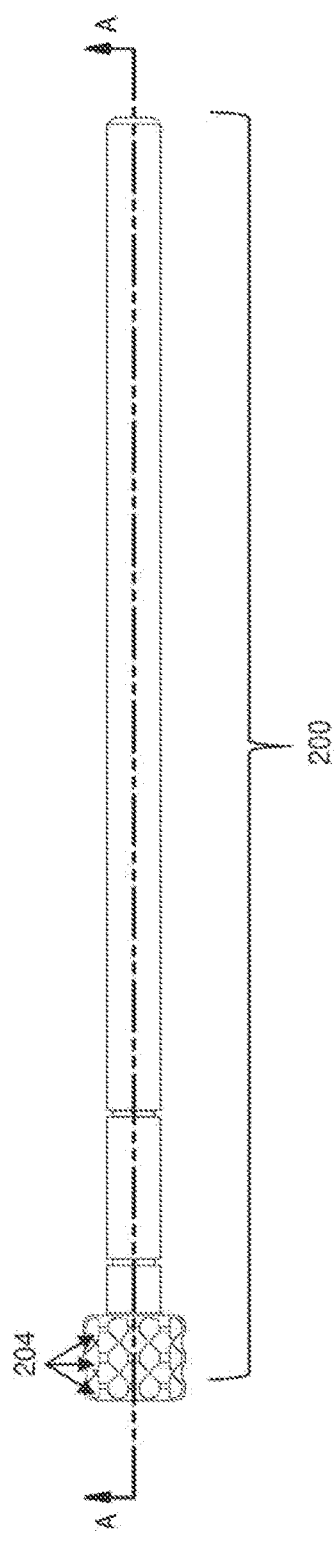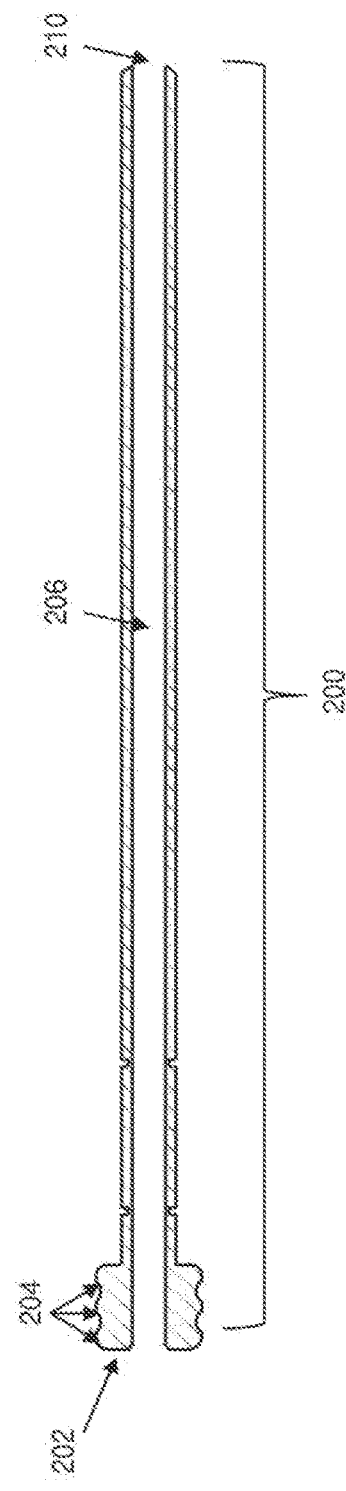
FIG. 10A
FIG. 10B

BONE DRILL GUIDES AND METHODS OF USE THEREOF

FIELD OF THE INVENTION

The invention relates to devices, in particular, bone drill guides, methods of use thereof, and kits for the treatment of bone defects.

BACKGROUND OF THE INVENTION

Fixation tools and devices, which are available in a wide variety of different shapes and sizes, have long been used in the repair of bone defects, such as bone fractures. An operator typically sets the bone to be repaired in the proper position and then uses the fixation tools and devices to secure the bone in that position for healing.

A fixation device, such as a bone plate or rod, can be secured to the bone by a fixation tool, such as a bone screw. Alternatively, a bone screw can be used by itself to repair a bone defect. To install these fixation devices, an operator will typically insert guide wires or similar devices into the bone that serve as guides for drilling, reaming, screw-tapping, and/or to aid in the installation of the fixation device(s) into the bone. An advantage of this method is that the placement of the guide wire and, accordingly, the future site of the drilled bore hole, can be confirmed, e.g., with X-rays, prior to drilling. Guide wires also provide stability and guidance during drilling or the insertion of devices, such as bone screws, into bone.

Installation of guide wires is often a free-hand procedure, which may be aided by X-rays taken in anterior-posterior and lateral planes before and after placement of the wire. This procedure requires considerable technical skill and often involves one or more attempts before appropriate positioning is achieved. The frequent difficulty in inserting and positioning guide wires is compounded by the slippery environment of surgical operations and the tendency of the narrow guide wires to wobble and bend as they are inserted into position in the bone. For many procedures, multiple guide wires are inserted into a damaged bone, preferably in a mutually parallel relationship. The distance and alignment between these devices within the bone may be critical for a successful operation.

In the past, bone drill guides designed to assist with positioning of guide wires have been plagued by slippage issues and difficulty when used with X-rays, both of which can extend the time of surgery, which is adverse to the patient and expensive. Operator errors including installing a guide wire into the bone at an incorrect site or at an incorrect orientation relative to other hardware can necessitate insertion of additional guide wires to correct the error. These errors can damage an already-defective bone, leading to bone fragility, an increase in bone damage, and poor healing.

Thus, there remains a need for a bone drill guide that addresses slippage issues and can ensure correct spatial orientation of hardware or devices used for fracture fixation.

SUMMARY OF THE INVENTION

In general, the invention features bone drill guides, sleeves, kits, and methods of use thereof for insertion of hardware into bone and the treatment of bone defects.

Accordingly, in a first aspect, the invention features a bone drill guide that includes a) a shaft having a proximal end and a distal end; b) an arcuate element attached to the distal end of the shaft, wherein the arcuate element is sized for seating on bone; c) a guide base attached to the proximal end of the shaft, wherein the guide base includes at least two peripheral guide bores, wherein each of the peripheral guide bores is positioned about the shaft; and d) an interior channel extending through the guide base, the shaft and the arcuate element.

In some embodiments, the shaft has a length of about 100 mm to about 300 mm, e.g., about 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or a value in a range spanning any of the preceding values.

In several embodiments, the arcuate element has a concave face with an arc length of about 15 mm to about 60 mm, e.g., 15 mm, 20 mm, 25 mm, 30 mm, 35 mm, 40 mm, 45 mm, 50 mm, 55 mm, 60 mm, or a value in a range spanning any of the preceding values. In some embodiments, the arc length is about 39.37 mm. In several embodiments, the arcuate element has a concave face with a central angle of about 108°.

In some embodiments of the first aspect of the invention, each of the peripheral guide bores has a diameter of about 2 mm to about 7 mm, e.g., about 2 mm, 3 mm, 4 mm, 5 mm, 6 mm, or 7 mm, or a value in a range spanning any of the preceding values.

In some embodiments, the interior channel has a diameter of about 2 mm to about 7 mm, e.g., about 2 mm, 3 mm, 4 mm, 5 mm, 6 mm, or 7 mm, or a value in a range spanning any of the preceding values. In some embodiments, the interior channel has a length of about 100 mm to about 300 mm, e.g., about 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or a value in a range spanning any of the preceding values.

In several embodiments of the first aspect of the invention, each of the peripheral guide bores has a central point and at least two of the peripheral guide bores are positioned from about 10 mm to about 35 mm apart (e.g., about 10 mm, 15 mm, 20 mm, 25 mm, 30 mm, or 35 mm apart) as measured from the central points of the peripheral guide bores. In several embodiments, the interior channel has a central point and the central point is positioned from about 10 mm to about 20 mm from the central point of at least two of the peripheral guide bores. In some embodiments, the longitudinal axis of each of the peripheral guide bores is substantially parallel to the longitudinal axis of the interior channel.

In certain embodiments of the first aspect of the invention, the guide includes two or more of the following characteristics: a) the shaft has a length of about 100 mm to about 300 mm; and/or b) the arcuate element has concave face with an arc length of about 15 mm to about 60 mm; and/or c) the peripheral guide bore has a diameter of about 2 mm to about 7 mm; and/or d) the interior channel has a diameter of about 2 mm to about 7 mm; and/or e) the interior channel has a length of about 100 mm to about 300 mm; and/or f) the peripheral guide bores each have a central point, wherein peripheral guide bores are positioned from about 10 mm to about 35 mm apart as measured from their central points; and/or g) the interior channel has a central point and is positioned from about 10 mm to about 20 mm from the central point of one or more of the peripheral guide bores; and/or h) the peripheral guide bores are substantially parallel to the interior channel. In some embodiments, the guide includes each of the characteristics a) through h).

In some embodiments of the first aspect of the invention, the guide base contains two peripheral guide bores. In certain embodiments, the central points of the peripheral bore guides are about 13.1 mm apart and the central point of each peripheral bore guide is about 13.2 mm from the central point of the interior channel. In other embodiments, the guide base includes three peripheral guide bores.

In yet other embodiments of the first aspect of the invention, the guide base includes four peripheral guide bores. In some embodiments, the peripheral guide bores are positioned radially about the interior channel. In certain embodiments, the central point of each of the peripheral guide bores is positioned from about 10 mm to about 20 mm, e.g., about 10 mm, 11 mm, 12 mm, 13 mm, 14 mm, 15 mm, 16 mm, 17 mm, 18 mm, 19 mm, 20 mm, or a value in a range spanning any of the preceding values, from the central point of the interior channel. In some embodiments, the central points of a first and a second peripheral guide bore are about 26.4 mm apart, wherein the central points of a third and a fourth peripheral guide bore are about 26.4 mm apart, wherein the central points of the first and third and of the second and fourth peripheral guide bores are about 13.1 mm apart, wherein the central point of each of the peripheral guide bores is about 13.2 mm from the central point of the interior channel, wherein the central point of the interior channel is about midway between the first and second and between the third and fourth peripheral bore guides. In some embodiments, the guide base includes more than four peripheral guide bores.

In several embodiments of the first aspect of the invention, the guide further includes at least two sleeves capable of being slidably inserted into the peripheral guide bores of the guide base, wherein each sleeve includes a channel. In certain embodiments, the guide further includes four sleeves for insertion into four peripheral guide bores. In some embodiments, the sleeve channel of the sleeve has a diameter of about 4.2 mm to about 4.3 mm and a length from about 143.7 mm to about 144 mm.

In several embodiments of the first aspect of the invention, the guide further includes a handle. In some embodiments, the handle includes a handle shaft connected to the guide base and a handle grip. In certain embodiments, the handle shaft is between about 70 mm to about 110 mm long. e.g., about 70 mm, 75 mm, 80 mm, 85 mm, 90 mm, 95 mm, 100 mm, 105 mm, or 110 mm, or a value in a range spanning any of the preceding values. In certain embodiments, the handle grip is between about 90 mm to about 150 mm long, e.g., about 90 mm, 100 mm, 110 mm, 120 mm, 130 mm, 140 mm, 150 mm, or a value in a range spanning any of the preceding values. In some embodiments, the handle is removable from the guide base. In some embodiments, the angle of the handle relative to the guide base is adjustable.

In any of the preceding embodiments, the arcuate element or the guide base can be detachably attached to the shaft. In any of the preceding embodiments, the interior channel and the peripheral guide bores can be sized for slidable insertion of hardware therethrough. In some embodiments, the hardware is selected from the group consisting of guide wires, guide pins, sleeves, and drill bits. In any of the preceding embodiments, the guide base can have a proximal end and a distal end, wherein the distal end is attached to the shaft, wherein the distal end of the guide base has a nose and/or a nose tip. In any of the preceding embodiments of the first aspect of the invention, the curvature or size of the arcuate element can be adjustable. In any of the preceding embodiments, the arcuate element can include one or more holes parallel to the longitudinal axis of the shaft, wherein preferably said arcuate element comprises 2 or more holes.

With reference to any bone drill guide dimensions described herein, larger or smaller guides or portions thereof that scale proportionally in some or all dimensions are also contemplated, as well as larger or smaller guides or portions thereof that do not scale proportionally. Generally, the dimensions of a guide or portion thereof to be used in a surgical procedure are selected in accordance with the size, shape, and/or curvature (e.g., convexity) of the bone or bones being treated.

In a second aspect, the invention features a method for insertion of hardware into a bone, the method including a) positioning the guide of the first aspect of the invention in proximity to the bone using the arcuate element; and b) inserting the hardware through the interior channel or through one of the peripheral guide bores of the guide and into the bone. In some embodiments, X-ray or fluoroscopy is used to align the guide or hardware with a position on the bone. In some embodiments, the hardware is selected from a group consisting of guide wires, guide pins, intramedullary nails, plate devices, external fixation pins, and drill bits. In some embodiments, the hardware is inserted into the bone through the interior channel.

In several embodiments of the second aspect of the invention, multiple pieces of hardware are inserted into the bone using the guide. In some embodiments, at least two pieces of hardware are inserted into the bone in a sequential manner. For example, a first piece of hardware can be inserted through the interior channel and into the bone and at least one subsequent piece of hardware can be inserted through a first peripheral guide bore and into the bone. In certain embodiments, the first and second pieces of hardware are guide wires. In some embodiments, a third guide wire is inserted into the bone through a second peripheral guide bore. In some embodiments, the distance between any two of the guide wires is from about 10 mm to about 35 mm, e.g., 10 mm, 15 mm, 20 mm, 25 mm, 30 mm, 35 mm, or a value in a range spanning any of the preceding values. In certain embodiments, the distance between any two of the guide wires is about 13.2 mm. In some embodiments, the guide wires are inserted from about 50 mm to about 130 mm, e.g., 50 mm, 60 mm, 70 mm, 80 mm, 90 mm, 100 mm, 110 mm, 120 mm, 130 mm, or a value spanning any of the preceding values, into the bone. In certain embodiments, each of the guide wires is inserted to substantially the same depth into the bone.

In certain embodiments of the second aspect of the invention, the method further includes removing the guide and overdrilling the guide wires using a cannulated drill bit. In some embodiments, one or more bone screws is inserted into the bone along the guide wires. In certain embodiments, the bone screws are cannulated and fenestrated. In further embodiments, a flowable medium is introduced into the bone screw. In other embodiments, the method includes removing the guide wires and introducing a flowable medium into the bone without inserting bone screws. In some embodiments, the flowable medium is a bone void filler, a bone cement, or a pharmaceutical agent.

In preferred embodiments of the second aspect of the invention, the bone screw is an InnoVision (Memphis, Tenn., USA) N-FORCE FIXATION SYSTEM™ bone screw, for example, InnoVision Catalog Number IN001-25-FS, IN001-30-FS, IN001-35-FS. IN001-40-FS. IN001-45-FS, IN001-50-FS, IN001-55-FS, IN001-60-FS, IN001-65-FS. IN001-70-FS, IN001-75-FS, IN006-25-FS, IN006-25-FS, IN006-30-FS. IN006-35-FS, IN006-40-FS, IN006-45-FS, IN006-

50-FS, IN006-55-FS, IN006-60-FS, IN006-65-FS, and/or a bone screw described in U.S. Pat. No. 8,574,273 and PCT/US2014/020678.

In any of the preceding embodiments of the second aspect of the invention, the method includes repair of a bone defect. In some embodiments, the bone defect includes a defect of the radius, ulna, fibula, clavicle, humerus, pelvis, femur, patella, tibia, talus, calcaneus, navicular, cuneiforms, metatarsals, metacarpals, phalanges, scapula, ankle, mandible, or vertebra. In certain embodiments, the bone defect is a fracture. In still further embodiments, the bone is the femur and the defect is a fracture of the neck of the femur.

In a third aspect, the invention features a kit including any one or more, or all, of the following: a) the guide of the first aspect of the invention; b) at least two sleeves, wherein the kit optionally includes one or more of a depth gauge, a guide wire, a drill bit, a bone screw, a self-hardening bone cement powder, and instructions for using the kit. In some embodiments, the kit includes the guide of the first aspect of the invention and at least two sleeves. In certain embodiments, the curvature or size of the arcuate element of the guide is adjustable. In some embodiments, the arcuate element or the guide base is detachably attached to the shaft of the guide.

Definitions

As used herein, the term "about" means±10% of the recited value.

By "biocompatible" is meant that the material does not elicit a substantial detrimental response (e.g., an immune response) in the host. It should be appreciated that a foreign object introduced into a living body may induce an immune reaction that will have negative effects on the host. As used herein, the term "biocompatible" is intended to include those materials that may cause some inflammation but does not rise to the level of pathogenesis.

The term "bioresorbable" is meant the ability of a material to be resorbed by the body in vivo. The resorption process involves elimination of the original bioresorbable implant materials through the action of body fluids, enzymes, or cells. "Strongly bioresorbable" means that at least 80% of the total mass of material implanted in vive is resorbed within one year.

By "bone defect" is meant any bone deficient region, such as a void, gap, recess, or other discontinuity in a bone. A bone defect can be artificially or naturally established, and can occur, for example, due to disease or trauma. Thus, a bone defect can occur as a consequence of pathologic or inflammatory diseases, formation and/or removal of a bone tumor, a surgical intervention, a congenital defect, or a bone fracture, and the like. For example, in the case of certain diseases, such as bone tumors, the bone defect may be artificially established due to removal of the tumor tissue. The bone screws of the invention can be applied, for example, in the repair of periodontal defects, in craniofacial or maxillofacial surgery or reconstruction, in hand surgery, in joint reconstruction, in fracture repair, in orthopedic surgical procedures, and in spinal surgery (e.g., spinal fusion and vertebroplasty). The term "bone defect" is also intended to include anatomical sites where augmentation to a bony feature is desired by the patient in the absence of disease or trauma, such as in elective cosmetic surgery. Thus, the "defect" can be one that is subjectively perceived by the patient, and where augmentation of the bone deficient region is desired.

By "bone fill material" or "infill material" is meant any material for infilling a bone that includes an in-situ hardenable material, including, e.g., a flowable medium. The fill material also can include other "fillers," such as filaments, microspheres, powders, granular elements, flakes, chips, tubules and the like, autograft or allograft materials, as well as other chemicals, pharmacological agents, or other bioactive agents.

By "central point" is meant the geometric center of a channel or bore. In the present invention this concept is used to describe the relative geometric position of elements but is not a physical component of the invention.

By "circumferential augmentation" is meant that a flowable medium, e.g., bone cement, encompasses all or a portion of the linear distance around the circumference of a bone screw along all or a portion of its length (e.g., when the bone screw has been inserted into a bone), thereby improving one or more biomechanical properties of the bone screw (e.g., fixation strength and/or pullout strength). Typically cannulated and fenestrated bone screws are used to obtain this pattern of flowable medium infill. If multiple cannulated and fenestrated bone screws are inserted in the bone, circumferential augmentation of the flowable medium can lead to formation of an "internal buttress" formed out of the flowable medium that encompasses each of the inserted screws. This is also referred to as an internal "plate" on the inside of the bone, which serves as the functional equivalent of a metal plate on the outside of the bone but is formed from bone cement inside the bone. This internal plate or buttress can reduce or obviate the need for external supports such as metal bone plates on the outside of the bone.

By "curvature." as used herein, is meant the shape of a curved element. For example, an arcuate element may have a curvature that can be described by three parameters: a radius, a central angle, and an arc length, which have their conventional mathematical definitions as used herein. The arc length L (see FIG. 34A) of an arc of a circle with radius r and subtending an angle θ (measured in radians) with the circle center (i.e., the central angle) equals Br (see FIG. 34A). For illustration purposes, a diagram indicating the radius, arc length, and central angle of a concave face of an arcuate element is shown in FIG. 34B. When a device or part thereof is said to have a "radius" or a "central angle." these terms are used to describe the geometric parameters rather than physical components of the invention.

By "flowable medium" is meant, generally, a formulation of a resorbable or non-resorbable biocompatible agent, e.g., a polymer, such as a thermoset polymer or a thermoplastic polymer, e.g., PMMA (polymethylmethacrylate), a bone void filler material, a cement, or a pharmaceutical agent. In particular, the flowable medium may be a resorbable calcium phosphate or calcium sulphate cement, which is typically self-hardening and, once hardened, may allow for the gradual replacement of the cement with bone. Both resorbable and non-resorbable biocompatible agents, such as bone cements, have been used successfully in the treatment of bone defects.

Examples of calcium phosphate bone cements that can be used with the bone screws are described in, e.g., U.S. Pat. Nos. 5,783,217, 6,027,742, 6,214,368, 6,287,341, 6,331, 312, 6,541,037, 6,953,594, 6,972,130, 7,150,879, 7,318,841, and 7,517,539, each of which is incorporated herein by reference, and includes commercially available cements such as BETA-BSM™ injectable paste and CARRIGEN® porous bone substitute material (Etex Corporation, Cambridge, Mass.).

By "guide wire" is meant devices which can be inserted into bone and which serve as guides for the insertion of subsequent devices or hardware into or along the bone.

Guide wires can be used in the treatment of bone defects. As used herein, the term guide wire encompasses threaded and non-threaded guide wires, guide-pins, K-wires, Kirschner wires, Steinmann pins, and other similar devices known in the art.

By "operator" is meant any individual who uses the bone drill guides of the invention. An operator can include, for example, physicians, surgeons, orthopedic doctors, veterinarians, nurses, technicians, etc.

By "osteoplasty" is meant any procedure in which bone fill material and/or a flowable medium is delivered to bone (e.g., into the interior of a bone).

By "procedure" is meant any operation, surgery, or related event in which devices or hardware are inserted into bone.

By "treating" or "treatment" is meant the medical management of a patient with the intent that an amelioration, repair, or prevention of an injury or disease, pathological condition, or disorder associated with a bone defect will result. This term includes active treatment, that is, treatment directed specifically toward improvement of the injury or disease, pathological condition, or disorder, and also includes causal treatment, that is, treatment directed toward removal of the cause of the injury or disease, pathological condition, or disorder. In addition, this term includes palliative treatment, that is, treatment designed for the relief of symptoms rather than the curing of the injury or disease, pathological condition, or disorder; preventive treatment, that is, treatment directed to prevention of the injury or disease, pathological condition, or disorder; and supportive treatment, that is, treatment employed to supplement another specific therapy directed toward the improvement of the injury or disease, pathological condition, or disorder.

Other features and advantages of the invention will be apparent from the following detailed description, and from the claims.

BRIEF DESCRIPTION OF THE DRAWINGS

FIG. 3A is a front view of the distal end of a guide base of a bone drill guide.

FIG. 3B is a bottom view of the guide base of FIG. 3A.

FIG. 3C is a sectional view along line A-A of the guide base of FIG. 3B.

FIG. 3D is a side view of the guide base of FIG. 3A.

FIG. 3E is an elevation view of the guide base of FIG. 3A.

FIG. 3F is a back view of the proximal end of the guide base of FIG. 3A.

FIG. 3G is a back view of the proximal end of the guide base of FIG. 3A rotated 90°.

FIG. 4A is a left side view of an arcuate element.

FIG. 4B is a back view of the arcuate element of FIG. 4A.

FIG. 4C is a right side view of an arcuate element.

FIG. 5A is a side view of a handle shaft of a bone drill guide.

FIG. 5B is a top view of the handle shaft of FIG. 5A.

FIG. 6A is a right side view of a handle grip of a bone drill guide; the left side view is identical.

FIG. 6B is a sectional view along line A-A of the handle grip of FIG. 6A.

FIG. 6C is a top view of a handle grip of the bone drill guide.

FIG. 7A is a front view of a bone drill guide.

FIG. 7B is a sectional view along line A-A of the top portion of the bone drill guide of FIG. 7A showing an interior channel that runs from the guide base through the arcuate element.

FIG. 8A is a bottom view of a bone drill guide.

FIG. 8B is a top view of a bone drill guide.

FIG. 10A is a side view of a sleeve.

FIG. 10B is a sectional view along line A-A of the sleeve of FIG. 10A.

FIG. 35A is a back view of a bone drill guide having a single peripheral guide bore shown in the upper left hand corner. FIG. 35B is a back view of a bone drill guide having peripheral guide bores shown in the upper left and right hand corners. FIG. 35C is a back view of a bone drill guide having a single peripheral guide bore shown in the upper right hand corner. FIG. 35D is a back view of a bone drill guide having a single peripheral guide bore shown in the lower left hand corner. FIG. 35E is a back view of a bone drill guide having peripheral guide bores shown in the lower left and right hand corners. FIG. 35F is a back view of a bone drill guide having a single peripheral guide bore shown in the lower right hand corner.

DETAILED DESCRIPTION OF THE INVENTION

The invention features bone drill guides, sleeves, kits, and methods of use thereof for insertion of hardware into bone and the treatment of bone defects.

Bone Drill Guides

A bone drill guide of the invention allows for firm seating of the guide against a bone, while also allowing for angulation, translation, and rotation, which enables accurate insertion of hardware into the bone at desired locations and orientations. Furthermore, multiple pieces of hardware can be inserted into a bone at precise positions and orientations relative to one another using the bone drill guide. The bone drill guides are also designed for convenient use with radiographic visualization. The bone drill guides are designed in particular for insertion of guide wires into a bone, especially for fixation of bone fractures using compression. These guide wires can be used in conjunction with other devices or hardware known in the art, non-limiting examples of which include drill bits, bone screws, bone plates, bone nails, and bone pins.

The following descriptions of the embodiments of bone drill guides of the invention and methods of use thereof are merely exemplary in nature and are in no way intended to limit the invention, its application, or its uses. Moreover, while the present invention is described in detail with reference to several different bone drill guides of the invention, it will be appreciated by those skilled in the art that the present invention is not limited by the forms and materials specifically described, but may also include related forms and materials.

There now follows a description of particular embodiments of the invention.

Structure

Figure 1B:
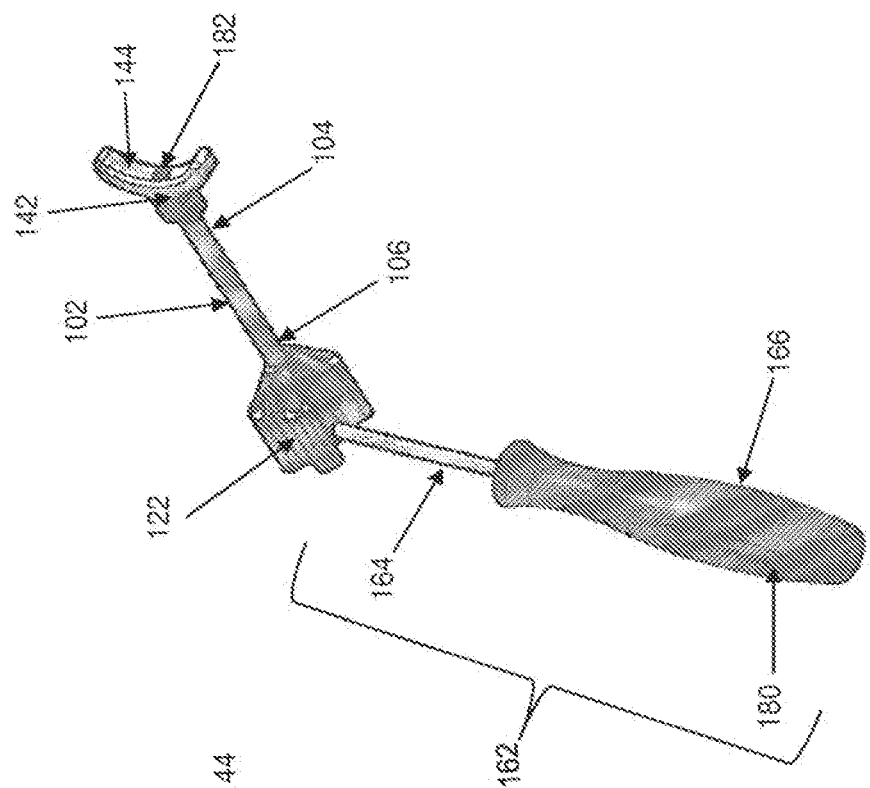
FIG. 1A is a right side elevation view and FIG. 1B is a perspective view of a schematic representation of a bone drill guide of the invention.
Figure 1A:
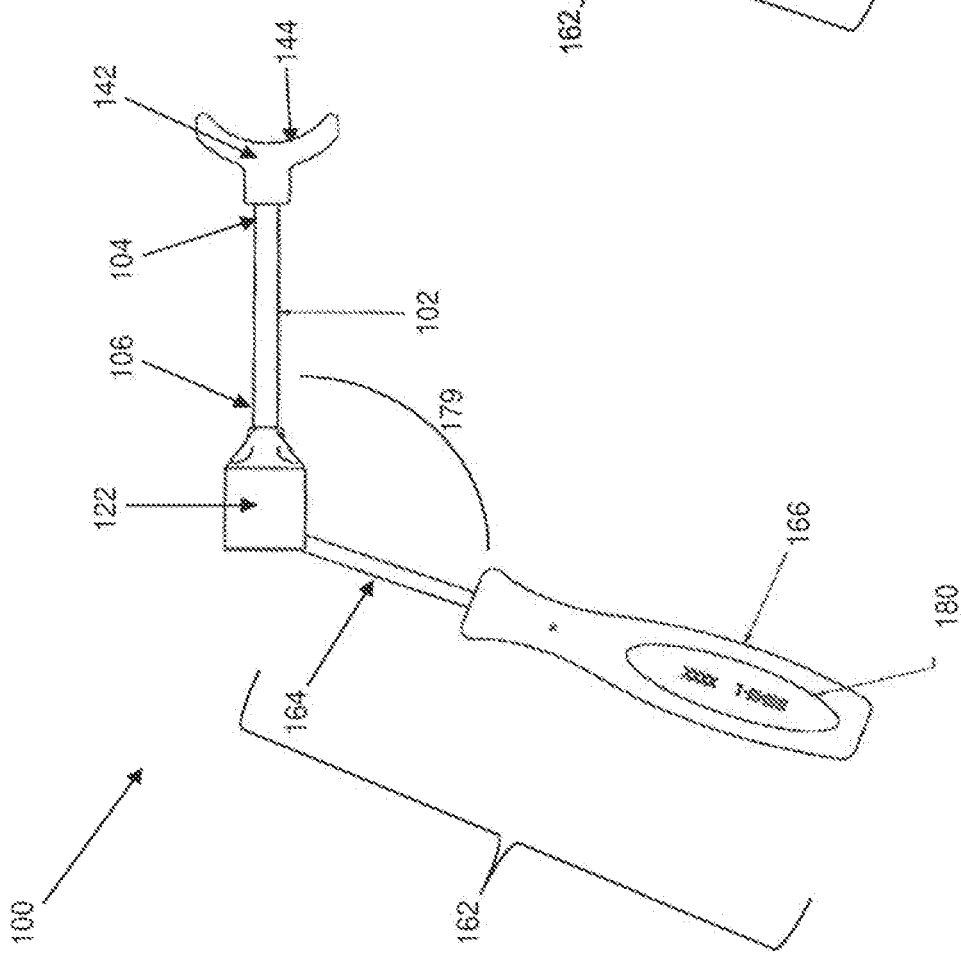

Referring to FIGS. 1A and 1B, bone drill guide 100 includes shaft 102 with proximal end 106 and distal end 104. Attached at proximal end 106 of shaft 102 is guide base 122, while arcuate element 142 is attached at distal end 104 of shaft 102. In some embodiments, shaft 102 is detachably connected to guide base 122, for example by a compression fitting, threaded fitting, or a locking mechanism. In other embodiments, shaft 102 is fixably connected to guide base 122, for example by welding or other connections known in the art. In some embodiments, arcuate element 142 is detachably connected to shaft 102, for example by a compression fitting, threaded fitting, or a locking mechanism. In other embodiments, arcuate element 142 is fixably attached to shaft 102, for example by welding or other connections known in the art. In preferred embodiments, drill guide 100 has a one shaft 102. In alternate configurations, arcuate element 142 may be attached to guide base 122 by multiple. e.g., 2, 3, 4, or 5 shafts 102, which may each have an interior channel 182. Arcuate element 142 has concave face 144. Attached to guide base 122 is handle portion 162, which includes handle shaft 164 that terminates with handle grip 166. In some embodiments, handle portion 162 is detachably connected to guide base 122, for example by a compression fitting (e.g., compression fitting with pinning), threaded fitting, or a locking mechanism. In other embodiments, handle portion 162 is fixably connected to guide base 122, for example by welding or other connections known in the art. In other embodiments, handle portion 162 is rotatably attached to guide base 122, for example by a hinge or a ball-and-socket joint, such that angle 179 between handle portion 162 and guide base 122 can be adjusted. In further embodiments, handle portion 162 can be locked in place following rotational adjustment. In some embodiments handle grip 166 has face 180 that includes indicia, such as a product name. In some embodiments, shaft 102 is welded to arcuate element 142 and guide base 122, handle shaft 164 is welded to guide base 122, and handle grip 166 is compressed and pinned to handle shaft 164. In other embodiments, shaft 102 is welded to arcuate element 142 and guide base 122, handle shaft 164 is welded to guide base 122, and handle grip 166 is press fit to handle shaft 164.

Interior channel 182 extends through guide base 122, shaft 102, and arcuate element 142. Interior channel 182 may have a length in the range of about 100 mm to about 350 mm, e.g. about 100 mm, 105 mm, 110 mm, 115 mm, 120 mm, 125 mm, 130 mm, 140 mm, 150 mm, 155 mm, 160 mm, 165 mm, 170 mm, 180 mm, 190 mm, 200 mm, 220 mm, 240 mm, 260 mm, 280 mm, 300 mm, 320 mm, 340 mm, 350 mm, or a value in a range spanning any of the preceding values. In a preferred embodiment interior channel 182 has a length of about 127 mm. In several embodiments, interior channel 182 is sized for insertion of guide wires or similar devices. Interior channel 182 may have a diameter in the range from about 2 mm to about 40 mm, e.g., about 2 mm, 3 mm, 4 mm, 5 mm, 6 mm, 7 mm, 8 mm, 10 mm, 15 mm, 20 mm, 25 mm, 30 mm, 35 mm, 40 mm, or a value in a range spanning any of the preceding values, and preferably about 3.4 mm.

Figure 2A:
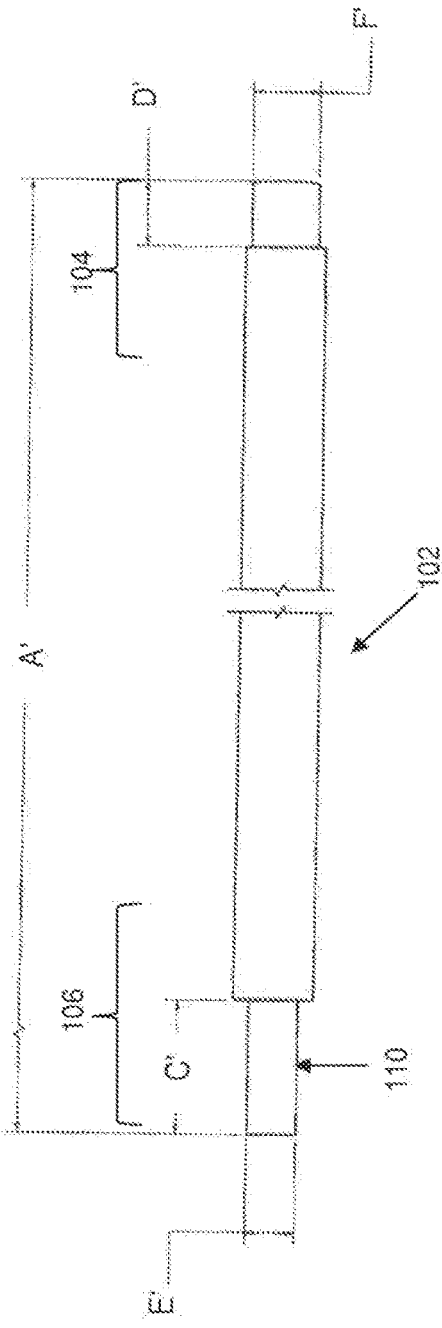
FIG. 2A is a top view of a shaft of a bone drill guide of the invention.
Figure 2B:
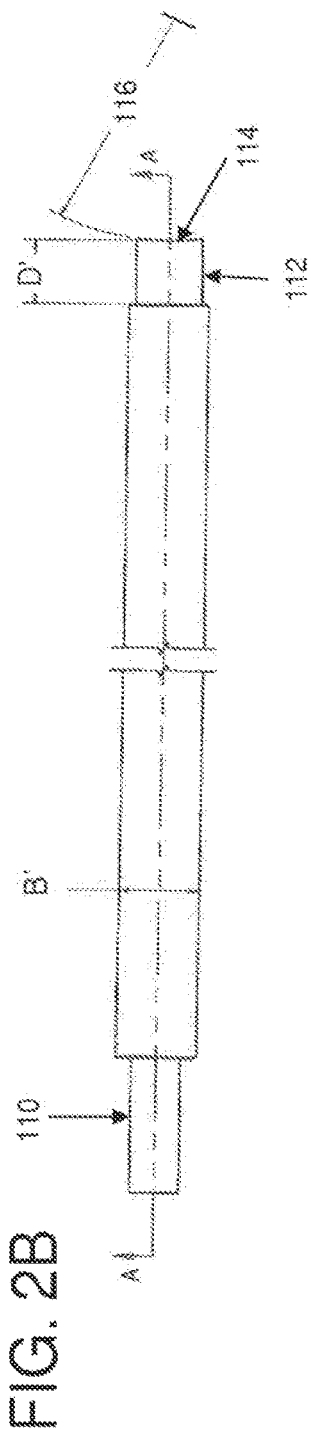
FIG. 2B is a side view of the shaft of FIG. 2A.
Figure 2C:
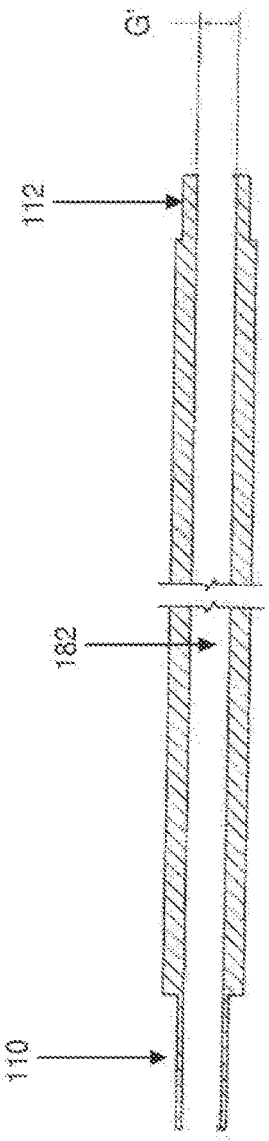
FIG. 2C is a sectional view along line A-A of the shaft of FIG. 2B.

Referring to FIGS. 2A-2C, shaft 102 has proximal 106 and distal 104 ends and includes interior channel 182. Shaft 102 may have a length A' (see FIG. 2A) in the range of about 100 mm to about 350 mm, e.g., about 100 mm, 105 mm, 110 mm, 115 mm, 120 mm, 125 mm, 130 mm, 140 mm, 150 mm, 160 mm, 180 mm, 190 mm, 200 mm, 220 mm, 240 mm, 260 mm, 280 mm, 300 mm, 320 mm, 340 mm, 350 mm, or a value in a range spanning any of the preceding values, and preferably about 127 mm. Shaft 102 may have an outer diameter B' (see FIG. 2B) in the range of about 2 mm to about 20 mm, e.g., about 2 mm, 4 mm, 6 mm, 8 mm, 10 mm, 12 mm, 14 mm, 16 mm, 18 mm, 20 mm, or a value in a range spanning any of the preceding values, and preferably about 7 mm. Proximal end 106 is sized for insertion into distal end 129 of guide base 122 at acceptor 136 (see FIG. 3C; insertion occurs in the direction of the arrow). Distal end 104 is sized for insertion into proximal end 158 of arcuate element 142 at acceptor 148 (see FIG. 4A; insertion occurs in the direction of the arrow). In some embodiments, shaft 102 can include proximal 110 and distal 112 insets. Proximal inset 110 may have a length C' (see FIG. 2A) in the range of about 10 mm to about 20 mm, e.g. about 10 mm, 12 mm, 14 mm, 16 mm, 18 mm, 20 mm, or a value in a range spanning any of the preceding values, preferably about 12.7 mm. Proximal inset 110 may have an outer diameter E' (see FIG. 2A) in the range of about 3 mm to about 6 mm, e.g., about 3 mm, 4 mm, 5 mm, 6 mm, or a value in a range spanning any of the preceding values, and preferably about 4.3 mm. Distal inset 112 may have a length D' (see FIGS. 2A and 2B) in the range of about 2 mm to about 10 mm, e.g. 2 mm, 4 mm, 6 mm, 8 mm, 10 mm, or a value in a range spanning any of the preceding values, preferably about 6.2 mm. Distal inset 112 may have an outer diameter F' (see FIG. 2A) with a length in the range of about 3 mm to about 8 mm, e.g., about 3 mm, 4 mm, 5 mm, 6 mm, 7 mm, 8 mm, or a value in a range spanning any of the preceding values, preferably about 5.8 mm. In some embodiments, distal inset 112 includes concave end 114. The curvature of concave end 114 may have a radius 116 (see FIG. 2B) that substantially matches the radius r of concave face 144 of arcuate element 142 (see FIGS. 4A and 34B) in the range of about 15 mm to about 60 mm. e.g., about 15 mm, 20 mm, 25 mm, 30 mm, 35 mm, 40 mm, 45 mm, 50 mm, 55 mm, 60 mm, or a value in a range spanning any of the preceding values, and preferably about 20.8 mm, such that the surfaces are flush when shaft 102 is fitted into arcuate element 142 at acceptor 148.

Referring to FIGS. 3A-3G, guide base 122 has proximal end 128 and distal end 129. Multiple peripheral guide bores 126 surround interior channel 182. Guide base 122 may have a length K' (see FIG. 3D) in the proximal to distal direction in the range of about 20 mm to about 80 mm, e.g., 20 mm, 25 mm, 30 mm, 35 mm, 40 mm, 45 mm, 50 mm, 60 mm, 70 mm, 80 mm, or a value in a range spanning any of the preceding values, and preferably about 38.1 mm. Guide base 122 may have a width O' (see FIG. 3F) in the range of about 20 mm to about 60 mm, e.g., 20 mm, 25 mm, 30 mm, 35 mm, 40 mm, 45 mm, 50 mm, 55 mm, 60 mm, or a value in a range spanning any of the preceding values, and preferably about 32.9 mm. Guide base 122 may have a height L' (see FIGS. 3A and 3D) in the range of about 10 mm to about 40 mm, e.g., 10 mm, 15 mm, 20 mm, 25 mm, 30 mm, 35 mm, 40 mm, or a value in a range spanning any of the preceding values, and preferably about 23 mm. In some embodiments, proximal end 128 may have proximal end chamfer I' (see FIG. 3D) along its edge, which may have a depth of about 0.3 mm to about 0.6 mm, e.g., 0.3 mm, 0.4 mm, 0.5 mm, or 0.6 mm, and preferably about 0.5 mm. Proximal end chamfer I' may have an angle of about 35° to about 55°, e.g., about 35°, 45°, 55°, or a value in a range spanning any of the preceding values, and preferably about 45° relative to proximal end 128 of guide base 122.

Referring to FIG. 3C, in some embodiments, acceptor 136 is sized to accept proximal end 106 of shaft 102 (see FIGS. 2A and 2B). Acceptor 136 can have proximal and distal regions, which in some embodiments may have different inner diameters and/or lengths. For instance, acceptor 136 at distal end 129 of guide base 122 can have an inner diameter C' (see FIG. 3C) in a range of about 4 mm to about 10 mm, e.g., 4 mm, 5 mm, 6 mm, 7 mm, 8 mm, 9 mm, 10 mm, or a value in a range spanning any of the preceding values, and preferably about 7 mm. This region of acceptor 136 at distal end 129 can have a length D' (see FIG. 3C) in a range of about 15 mm to about 35 mm, e.g., 15 mm, 20 mm, 25 mm, 30 mm, 35 mm, or a value in a range spanning any of the preceding values, and preferably about 25.4 mm. Acceptor 136 at proximal end 128 can be sized to accept proximal inset 110 of shaft 102 (see FIG. 2A), and may have an inner diameter F' (see FIG. 3C) in a range of about 2 mm to about 6 mm, e.g., 2 mm, 3 mm, 4 mm, 5 mm, 6 mm, or a value in a range spanning any of the preceding values, and preferably about 4.3 mm.

Referring to FIGS. 3A-3G and 35A-35F, guide base 122 may have between 1 and 10 peripheral guide bores 126, e.g., 1, 2, 3, 4, 5, 6, 7, 8, 9, or 10 peripheral guide bores 126. In a preferred embodiment, guide base 122 has 4 peripheral guide bores 126. Peripheral guide bore 126 may have a diameter in the range of about 2 mm to about 42 mm, e.g., about 2 mm, 3 mm, 4 mm, 5 mm, 6 mm, 7 mm, 8 mm, 10 mm, 12 mm, 14 mm, 16 mm, 18 mm 20 mm, 25 mm, 30 mm, 35 mm, 40 mm, 42 mm, or a value in a range spanning any of the preceding values. In a preferred embodiment, peripheral guide bore 126 has a diameter of 5.7 mm. In some embodiments, peripheral guide bore 126 can be disposed in guide bore wing 127. In some embodiments, each peripheral guide bore 126 is disposed in its own wing 127, that is, the number of peripheral guide bores 126 is the same as the number of wings 127. In preferred embodiments, guide base 122 has 4 wings 127. Wings 127 can have a width R' (see FIG. 3G) in the range of about 5 mm to about 45 mm, e.g., about 5 mm, 7 mm, 9 mm, 11 mm, 12 mm, 14 mm, 16 mm, 18 mm, 20 mm, 25 mm, 30 mm, 35 mm, 40 mm, 45 mm, or a value in a range spanning any of the preceding values, and preferably about 8.8 mm. Angle Q' (see FIG. 3F) between wings 127 on one side of a guide base 122 can be in the range of about 45° to about 120°, e.g., 45°, 55°, 65°, 75°, 80°, 90°, 100°, 110°, or 120°, and preferably about 90°. In preferred embodiments, the position of wings 127 on guide base 122 confers a substantially cruciform or X-wing shape to guide base 122 when viewed from the front or back (e.g., see FIGS. 3A, 3F, 3G). In these embodiments, guide base 122 can have a minimal width S' (see FIG. 3G) in the range of about 15 mm to about 35 mm, e.g., 15 mm, 20 mm, 25 mm, 30 mm, 35 mm, or a value in a range spanning any of the preceding values, and preferably about 25 mm. In these embodiments, guide base 122 can also have a minimal height T (see FIG. 3G) in the range of about 6 mm to about 18 mm, e.g., 6 mm, 8 mm, 10 mm, 12 mm, 14 mm, 16 mm, 18 mm, or a value in a range spanning any of the preceding values, and preferably about 11.1 mm.

Referring to FIGS. 3B, 3C, and 3E, in some embodiments, guide base 122 has acceptor bore 130 that is sized to accept handle shaft 164 (see FIG. 5A). Acceptor bore 130 can have a diameter M' (see FIG. 3E) in the range of about 3 mm to about 8 mm, e.g., 3 mm, 4 mm, 5 mm, 6 mm, 7 mm, 8 mm, or a value in a range spanning any of the preceding values, and preferably about 5.1 mm. Acceptor bore 130 can be disposed at least a distance H' (see FIG. 3B) from the edge of proximal end 128 in the range of about 0.5 mm to about 2.5 mm, e.g., 0.5 mm, 1 mm, 1.5 mm, 2 mm, or 2.5 mm, or a value in a range spanning any of the preceding values, and preferably about 1.5 mm. In some embodiments, handle shaft 164 (see FIG. 5A) is fixably connected to acceptor bore 130, e.g., by welding or by other connections known in the art. In other embodiments, handle shaft 164 (see FIG. 5A) is detachably connected to acceptor bore 130, for example by a compression fitting, threaded fitting, or by a locking mechanism. In still other embodiments, handle shaft 164 (see FIG. 5A) can by rotatably connected to guide base 122, for example by a hinge or a ball-and-socket joint, to allow for an adjustable angle between guide base 122 and handle shaft 164 (see FIG. 5A). In some embodiments, acceptor bore 130 is disposed at an angle E' (see FIG. 3C) relative to proximal end 128 in the range from about 5° to about 40°, e.g., 5°, 10°, 15°, 20°, 25°, 30°, 35°, 40°, or a value in a range spanning any of the preceding values, and preferably 20°. Referring to FIGS. 3A-3G and FIG. 12, distal end 129 of guide base 122 includes nose 134 and nose tip 138. Nose 134 can have a length J' (see FIG. 3D) in the range of about 8 mm to about 18 mm, e.g., 8 mm, 10 mm, 12 mm, 14 mm, 16 mm, 18, or a value in a range spanning any of the preceding values, and preferably about 12.7 mm. Nose tip 138 can have a width A' (see FIG. 3A) in a range of about 10 mm to about 20 mm, e.g., 10 mm, 11 mm, 12 mm, 13 mm, 14 mm, 15 mm, 16 mm, 17 mm, 18 mm, 19 mm, 20 mm, or a value in a range spanning any of the preceding values, and preferably about 14.6 mm. Nose tip 138 can have a height B' (see FIG. 3A) in a range of about 7 mm to about 14 mm, e.g., 7 mm, 8 mm, 9 mm, 10 mm, 11 mm, 12 mm, 13 mm, 14 mm, or a value in a range spanning any of the preceding values, and preferably about 9.9 mm. In some embodiments, nose tip 138 has chamfer 132.

The central point of a first peripheral guide bore 126 can be positioned in the range of about 10 mm to about 35 mm apart from the central point of a second peripheral guide bore 126, e.g., 10 mm, 15 mm, 20 mm, 30 mm, 35 mm apart, or a value in a range spanning any of the preceding values (e.g., in a distance corresponding to N'. P', or U', see FIG. 3F). In a preferred embodiment, the central points of any two peripheral guide bores are about 13 mm to about 26 mm apart. The central points of each peripheral guide bore 126 can be positioned in a range of about 10 mm to about 20 mm from the central point of interior channel 182, e.g., 10 mm, 11 mm, 12 mm, 13 mm, 14 mm, 15 mm, 16 mm, 17 mm, 18 mm, 19 mm, 20 mm, or a value in a range spanning any of the preceding values. In a preferred embodiment, the central point of one or more peripheral guide bores 126 is about 13.2 mm from the central point of interior channel 182. In a preferred embodiment, a bone drill guide, which can be used to insert devices such as guide wires into a bone (e.g., a human femur), includes guide base 122 having four peripheral guide bores 126 positioned around interior channel 182 (see, e.g., FIG. 3F), in which the pair of peripheral guide bores 126 above or below interior channel 182 (as oriented in FIG. 3F) have a distance P' (see FIG. 3F) between their central points in the range of about 15 mm to about 30 mm, e.g., 15 mm, 20 mm, 25 mm, 30 mm, or a value in a range spanning any of the preceding values, and preferably about 23 mm. In this embodiment, the pair of peripheral guide bores 126 to the left or right of interior channel 182 (as oriented in FIG. 3F) have a distance between their central points N' (see FIG. 3F) in the range of about 8 mm to about 20 mm apart, e.g., 8 mm, 10 mm, 12 mm, 14 mm, 16 mm, 18 mm, 20 mm, or a value in a range spanning any of the preceding values, and preferably about 13.1 mm.

Referring to FIGS. 4A-4C and FIG. 34B, arcuate element 142 has proximal 158 and distal 151 ends. Arcuate element 142 has concave face 144 and convex face 146. Concave face 144 has a curvature that allows for firm seating against one or more type(s) of bone. For example, concave face 144 can have an arc length L (see FIG. 34B), which is in a geometric relationship with radius r and central angle θ (see FIGS. 4C and 34B). Radius r can be in the range of about 15 mm to about 60 mm, e.g., about 15 mm, 20 mm, 25 mm, 30 mm, 35 mm, 40 mm, 45 mm, 50 mm, 55 mm, 60 mm, or a value in a range spanning any of the preceding values, and preferably about 20.8 mm. Central angle θ (see FIG. 34B) can be in the range of about 45° to about 15°, e.g., about 45°, 50°, 55°, 60°, 65°, 70°, 75°, 80°, 85°, 90°, 95°, 10°. 105°. 106°, 107°, 108°, 109°, 110°, 115°, 120°, 125°, 130°, 135°, 140°, 145° 150°, or a value in a range spanning any of the preceding values, and preferably about 108°. Arc length L (see FIG. 34B) can be in the range of about 15 mm to about 60 mm, e.g., 15 mm, 20 mm, 25 mm, 30 mm, 35 mm, 40 mm, 45 mm, 50 mm, 55 mm, 60 mm, or a value in a range spanning any of the preceding values, and preferably about 39.37 mm.

Figure 34B:
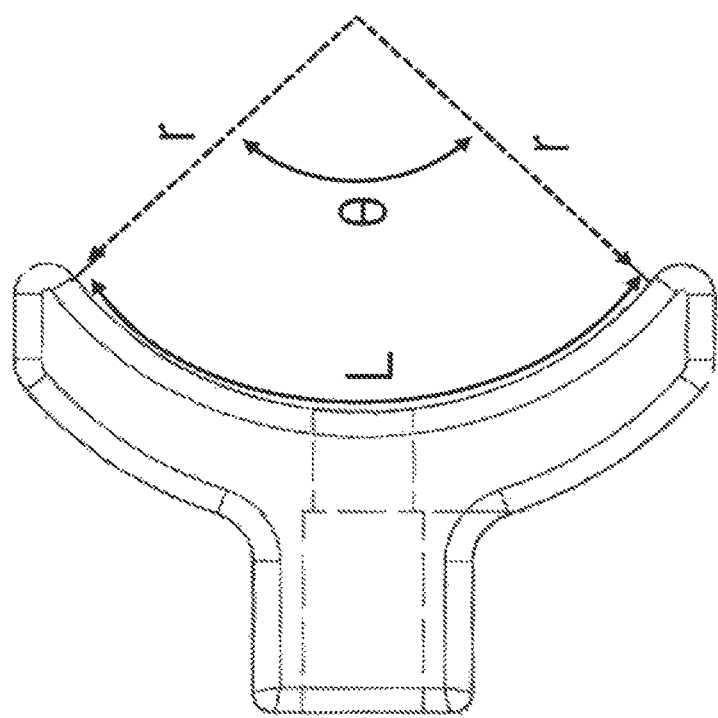
FIG. 34B is a right side view of the arcuate element of FIG. 4C with a diagram illustrating the radius (r), angle (θ), and arc length (L) of the concave face of the arcuate element. In this embodiment the concave face has a fixed radius.
Figure 34A:
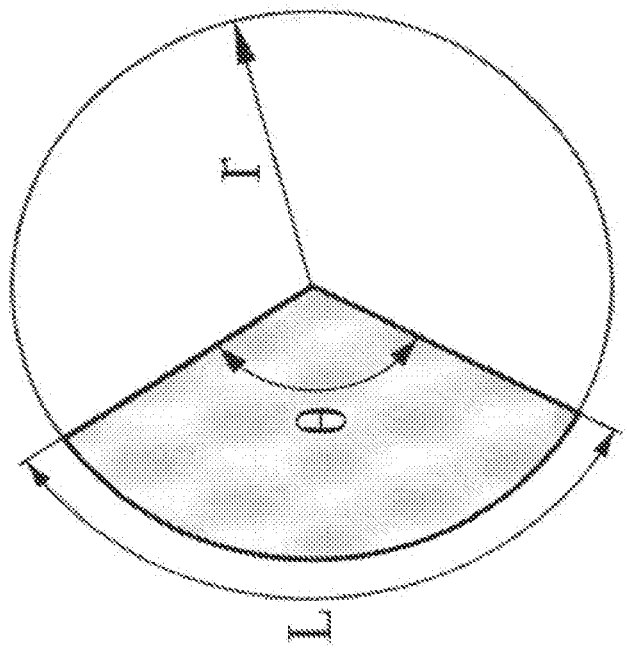
FIG. 34A is a diagram illustrating the radius (r), angle (θ), and arc length (L) of an arc of a circle.
Figure 35:
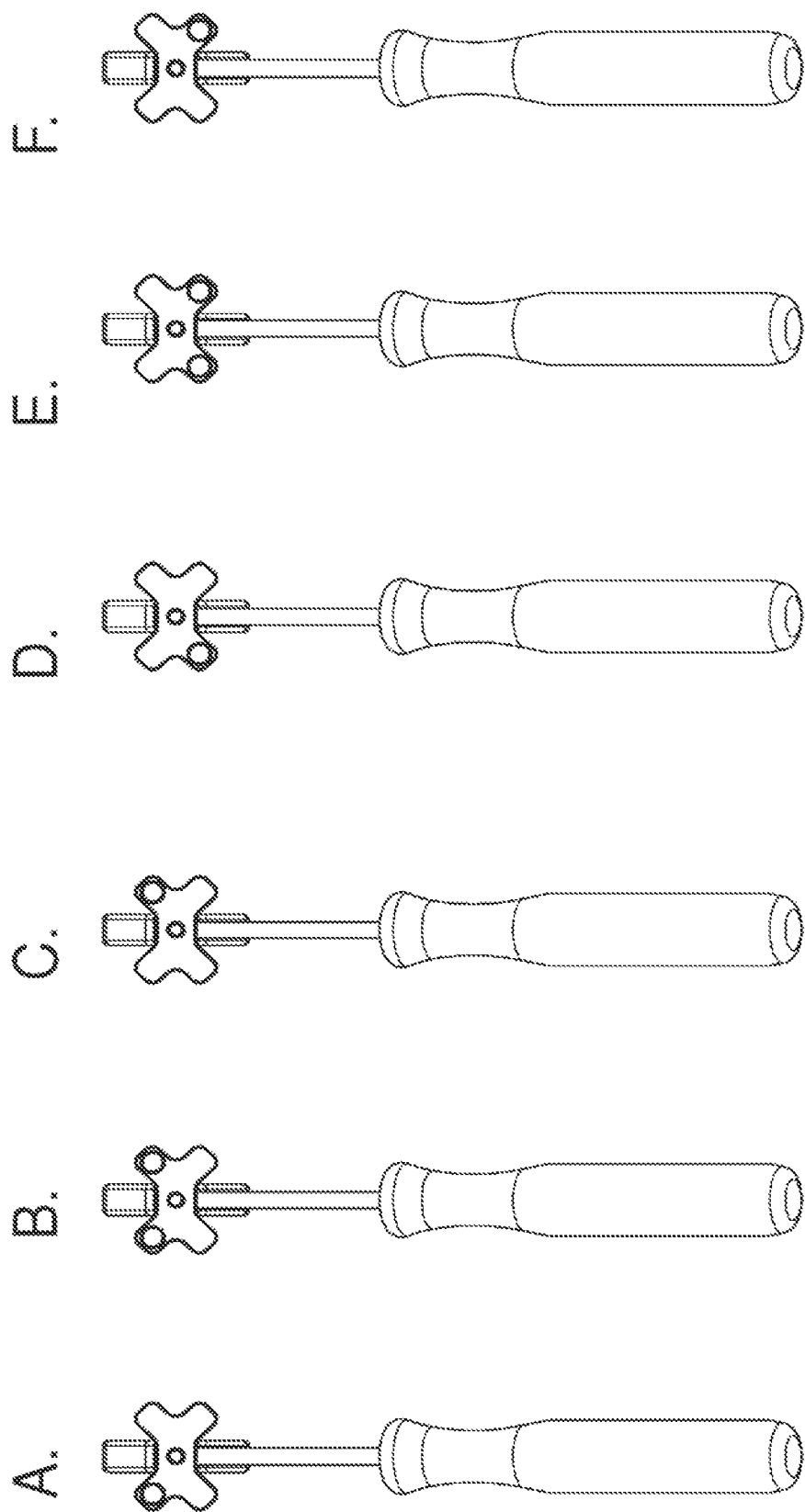
FIGS. 35A-35F are back views of bone drill guides with different numbers and arrangements of peripheral guide bores within the guide base.

It is to be understood that in some embodiments, concave face 144 has a substantially uniform radius r, such that concave face 144 can be considered as an arc of a circle with an arc length L (see FIG. 34B). In other embodiments, concave face 144 may have a variable radius at different points, which can confer different shapes to concave face 144, for example oval or ovoid shapes. In some embodiments, radius r of concave face 144 is fixed, for example because arcuate element 142 is provided as a solid assembly. In other embodiments, radius r of concave face 144 is adjustable. In some embodiments, concave face 144 may have, e.g., a hinge and/or a locking ratchet, which in certain embodiments may be actuatable by a lever included, e.g., on handle grip 166, manually at arcuate element 142, or by other means. In other embodiments, radius r of concave face 144 can be adjusted by hand. In other embodiments, arcuate element 142 may have knurling or other surface structure(s) on all or a portion of concave face 144 that can increase grip (i.e., traction) of bone drill guide 100 against a bone. In some embodiments, a gripping or textured material is included along all or a portion of concave face 144 or provided as an additional layer.

Referring to FIGS. 4A-4C, arcuate element 142 has a height B' (see FIG. 4B) that may be defined as a function of the curvature of concave face 144, and may be in the range of about 15 mm to about 60 mm, e.g. 15 mm, 20 mm, 25 mm, 30 mm, 35 mm, 40 mm, 45 mm, 50 mm, 55 mm, 60 mm, or a value in a range spanning any of the preceding values, and preferably about 40.6 mm. Arcuate element 142 may have a width C' (see FIG. 4B) in the range of about 5 mm to about 20 mm, e.g., 5 mm, 6 mm, 7 mm, 8 mm, 9 mm, 10 mm, 11 mm, 12 mm, 15 mm, 20 mm, or a value in a range spanning any of the preceding values, and preferably about 9.5 mm. Arcuate element may have tips 156, which may have widths K' (see FIG. 4A) in the range of about 4 mm to about 12 mm, e.g., 4 mm, 6 mm, 8 mm, 10 mm, 12 mm, or a value in a range spanning any of the preceding values, and preferably about 6.4 mm. Tip 156 may be located at least a distance J' (see FIG. 4A) from proximal end 158 of arcuate element 142. Distance J' may be in the range of 12 mm to about 28 mm, e.g., 12 mm, 14 mm, 16 mm, 18 mm, 20 mm, 24 mm, 26 mm, 28 mm, or a value in a range spanning any of the preceding values, and preferably about 20.4 mm.

Referring to FIGS. 4A-4C, in some embodiments, arcuate element 142, which has proximal end 158 and distal end 151, has acceptor 148 that is sized to accept distal end 104 of shaft 102 (see FIGS. 2A-2C). Acceptor 148 can have proximal and distal regions, which in some embodiments may have different inner diameters and/or lengths. For instance, acceptor 148 at distal end 151 of arcuate element 142 may have an inner diameter F' (see FIG. 4C) in the range of about 3 mm to about 9 mm, e.g., 3 mm, 5 mm, 7 mm, or 9 mm, or a value in a range spanning any of the preceding values, and preferably 5.8 mm. Acceptor 148 at proximal end 158 of arcuate element 142 may have an inner diameter D' in the range of about 4 mm to about 10 mm, e.g., 4 mm, 6 mm, 8 mm, 10 mm, or a value in a range spanning any of the preceding values, and preferably about 7 mm. The region of acceptor 148 at proximal end 158 of arcuate element 142 may have a length E' (see FIG. 4C) in the range of about 8 mm to about 16 mm, e.g., 8 mm, 10 mm, 12 mm, 14 mm, 16 mm, or a value in a range spanning any of the preceding values, and preferably about 12.7 mm. Acceptor 148 may have a total length in the proximal-distal direction G' (see FIG. 4A) in the range of about 10 mm to about 40 mm, e.g., 10 mm, 15 mm, 20 mm, 25 mm, 30 mm, 35 mm, 40 mm, or a value in a range spanning any of the preceding values, and preferably about 19.1 mm. Arcuate element 142 may have a height H' (see FIG. 4A) at proximal end 158 in the range from about 8 mm to about 16 mm, e.g., 8 mm, 10 mm, 12 mm, 14 mm, 16 mm, or a value in a range spanning any of the preceding values, and preferably about 12.7 mm.

Figure 36B:
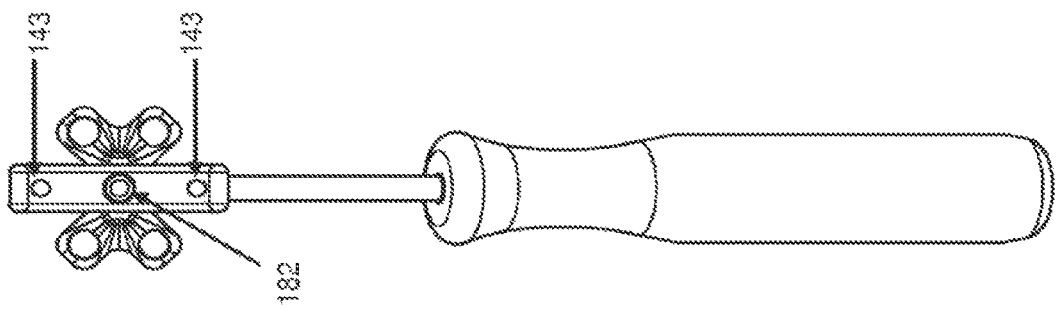
FIG. 36B is a front view of the bone drill guide of FIG. 36A.
Figure 36A:
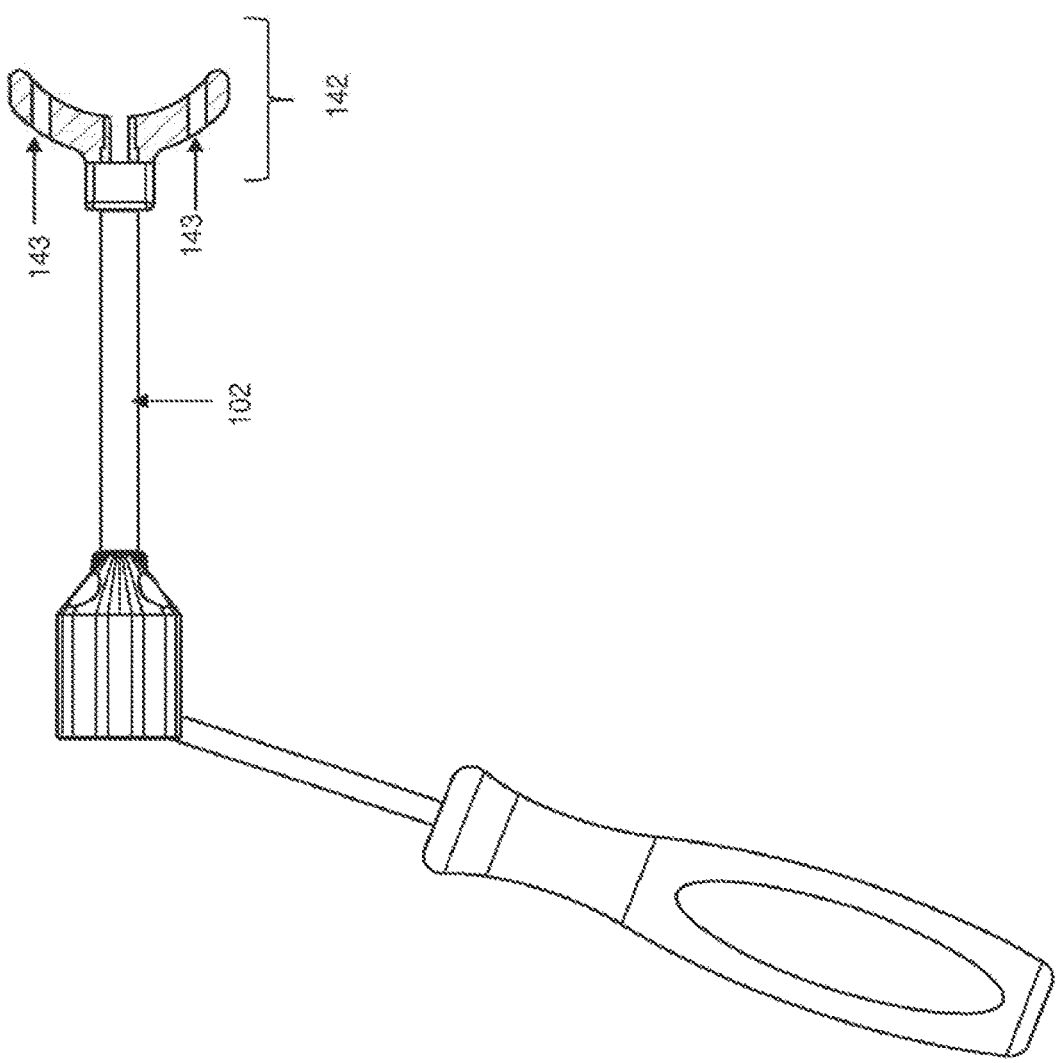
FIG. 36A is a right side view of a bone drill guide that includes two pin holes in the arcuate element. The arcuate element is shown in a partial sectional view for ease of illustrating the positioning of the pin holes within the arcuate element.

Referring to FIGS. 36A and 36B, in some embodiments, arcuate element 142 may have between 1 and 8 pin holes 143, e.g., 1, 2, 3, 4, 5, 6, 7, or 8 pin holes 143, and preferably 2 pin holes 143. In some embodiments, pin hole(s) 143 are substantially parallel to the longitudinal axis of shaft 102 and interior channel 182, as shown in FIGS. 36A and 36B. In other embodiments, pin hole(s) 143 may be non-parallel relative to the longitudinal axis of shaft 102 and interior channel 182, for example, pin hole(s) 143 may be aligned with the radius r (see FIG. 34B) of arcuate element 142. Pin hole(s) 143 may have an inner diameter in the range of about 2 mm to about 18 mm, e.g., 2 mm, 4 mm, 6 mm, 8 mm, 10 mm, 12 mm, 14 mm, 16 mm, 18 mm, or a value in a range spanning any of the preceding values, and preferably about 3.4 mm. Pin hole(s) 143 may be positioned above, below, or preferably both above and below shaft 102, as oriented in FIG. 36A. In some embodiments, the central points of pin hole(s) 143 are medially disposed in arcuate element 142. In some embodiments, the central points of pin hole(s) 143 are aligned with the central point of interior channel 182. In some embodiments, the central points of pin hole(s) 143 may be positioned between about 10 mm to about 30 mm, e.g., 10 mm, 14 mm, 16 mm, 20 mm, 24 mm, 28 mm, or 30 mm from the central point of interior channel 182.

Referring to FIGS. 5A and 5B, handle shaft 164 has distal 172 and proximal 170 ends (see FIG. 6A). Distal end 172 is sized for insertion into acceptor bore 130 of guide base 122 (FIGS. 3B-3C). Handle shaft 164 can have a length A' (see FIG. 5A) in the range of about 70 mm to about 110 mm, e.g., 70 mm, 75 mm, 80 mm, 85 mm, 90 mm, 95 mm, 100 mm, 105 mm, 110 mm, or a value in a range spanning any of the preceding values, and preferably about 89 mm. Handle shaft 164 can have a diameter in the range of about 2 mm to about 10 mm, e.g., 2 mm, 3 mm, 4 mm, 5 mm, 6 mm, 7 mm, 8 mm, 9 mm, 10 mm, or a value in a range spanning any of the preceding values, and preferably about 5.1 mm. In some embodiments, handle shaft 164 can include dowel pin hole 168 for securing to handle grip 166 (see FIG. 6B). Handle shaft dowel pin hole 168 can have a diameter in a range from about 1 mm to about 3 mm, e.g., 1 mm, 2 mm, 3 mm, or a value in a range spanning any of the preceding values, and preferably 1.6 mm. Handle shaft dowel pin hole 168, if present, can be disposed a distance B' (see FIG. 5A) from proximal end 170 of handle shaft 164 in the range of about 2 mm to about 6 mm, e.g. 2 mm, 4 mm, 6 mm, or a value in a range spanning any of the preceding values, and preferably about 4.4 mm.

Referring to FIGS. 6A-6C, handle grip 166 may have a length A' (see FIG. 6A) in the range of about 90 mm to about 150 mm, e.g., 90 mm, 100 mm, 110 mm, 120 mm, 130 mm, 140 mm, 150 mm, or a value in a range spanning any of the preceding values, and preferably about 119.3 mm. Handle grip 166 may have a diameter at its widest point B' (see FIG. 6B) in the range of about 15 mm to about 50 mm, e.g., 15 mm, 20 mm, 25 mm, 30 mm, 35 mm, 40 mm, 45 mm, 50 mm, or a value in a range spanning any of the preceding values, and preferably about 28 mm. Handle grip 166 may have a diameter at its narrowest point L' (see FIG. 6B) in the range of about 10 mm to about 20 mm, e.g., 10 mm, 12 mm, 14 mm, 16 mm, 18 mm, 20 mm, or a value in a range spanning any of the preceding values, and preferably about 15.7 mm. In some embodiments, handle grip 166 has handle shaft acceptor 178 into which proximal end 170 of handle shaft (FIG. 5A) can be inserted. Handle shaft acceptor 178 may have a length C' (see FIG. 6B) in the range of about 20 mm to about 40 mm, e.g., 20 mm, 25 mm, 30 mm, 35 mm, 40 mm, or a value in a range spanning any of the preceding values, and preferably about 30.5 mm. Handle shaft acceptor 178 can have an inner diameter D' (see FIG. 6B) in the range of about 3 mm to about 8 mm, e.g., 3 mm, 5 mm, 6 mm, 8 mm, or a value in a range spanning any of the preceding values, and preferably about 5 mm. In other embodiments, a screw or other fastener can be used to secure handle grip 166 to handle shaft 164. In some embodiments, handle grip 166 is press fit to handle shaft 164. In other embodiments, handle grip 166 is fixably attached to handle shaft 164, for example by welding, adhesives, or other connections known in the art. In other embodiments, handle shaft 164 is provided as a unitary body with handle grip 166. In some embodiments, handle grip 166 is pinned to handle shaft 164, and handle grip 166 has dowel pin hole 174. Dowel pin hole 174 can be located a distance J' (see FIG. 6A) from distal end 177 of handle grip 166. Distance J' can be in the range of about 16 mm to about 32 mm, e.g., 16 mm, 20 mm, 24 mm, 28 mm, 32 mm, or a value in a range spanning any of the preceding values, and preferably about 23.3 mm. In some embodiments, when dowel pin hole 174 is aligned with dowel pin hole 168 of handle shaft 164 (see FIG. 5A), a dowel pin can be inserted therethrough in order to secure handle grip 166 to handle shaft 164 (see FIG. 5A). The dowel pin can be fixably (e.g., with glue, adhesives, etc.) or removably inserted. Handle grip 166 may have knurling or textured elements, or have additional textured materials added, or designs in order to facilitate comfortable and steady grip to prevent or minimize slippage of the handle in the operator(s) hand(s).

Referring to FIGS. 7A-7B, interior channel 182 passes through guide base 122, shaft 102, and arcuate element 142. Interior channel 182 is sized for slidable insertion of guide-wires and other devices. For example, a guide wire can be inserted into proximal opening 184 of interior channel 182 and can exit through distal opening 186 into a bone. In some embodiments, interior channel 182 is sized for slidable insertion of a 5.5 mm drill guide. For example, a 5.5 mm drill guide can be inserted into proximal opening 184 of interior channel 182. In some embodiments, guide base 122, shaft 102, and arcuate element 142 are provided as subassemblies that can be fixably (e.g., by welding or other connections known in the art) or removably (e.g., by compression fitting, threaded fitting, etc.) joined as shown, for example, in FIG. 7B. For instance, distal end 104 of shaft 102 can be fitted into acceptor 148 (see FIG. 4A, insertion is in the direction of the arrow) of arcuate element 142. In some embodiments, distal inset 112 of shaft 102 is located in the distal region of acceptor 148 of arcuate element 142, such that concave end 114 (see FIG. 2B) of shaft 102 is flush with concave face 144 of arcuate element 142. Proximal end 106 of shaft 102 can be fitted into acceptor 136 of guide base 122 (see FIG. 3C, insertion is in the direction of the arrow). In some embodiments, proximal inset 110 of shaft 102 is located in the proximal region of acceptor 136 of guide base 122, such that the end of proximal inset 110 is flush with proximal end 128 of guide base 122. In other embodiments, guide base 122, shaft 102, and arcuate element 142 are provided as a unitary body with interior channel 182 passing through each element which can be formed, e.g., by molding, casting, three-dimensional (3D) printing, machining, or other approaches known in the art.

Figure 9B:
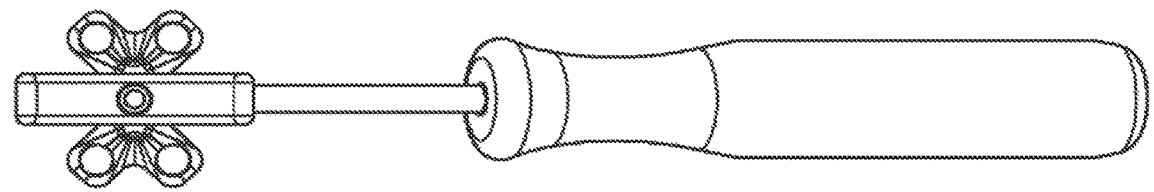
FIG. 9B is a front view of a bone drill guide of FIG. 9A.
Figure 9A:
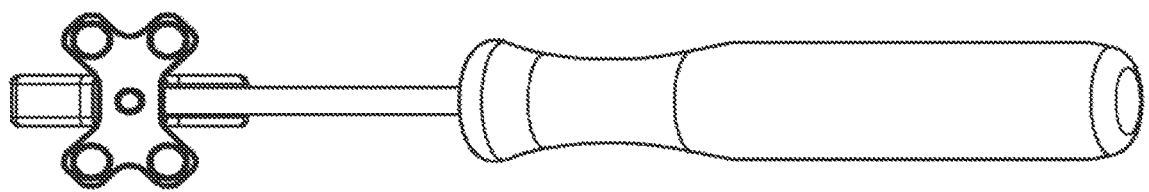
FIG. 9A is a back view of a bone drill guide.
Figure 11B:
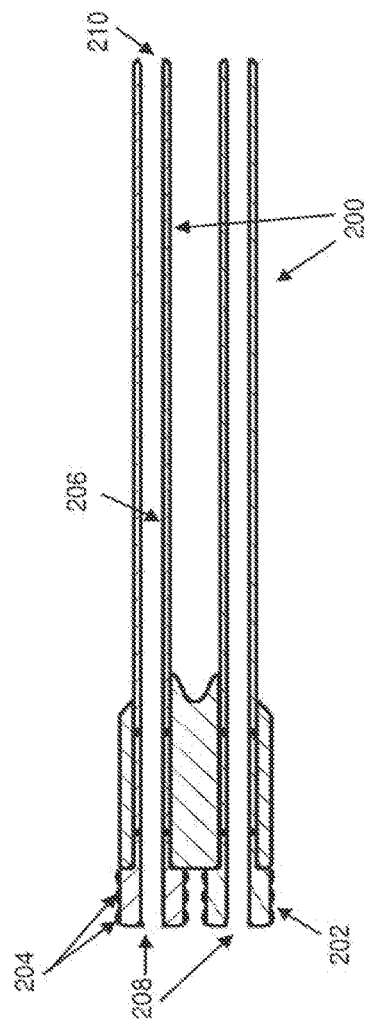
FIG. 11B is a sectional view along line A-A of the guide base and sleeves of FIG. 11A.
Figure 11A:
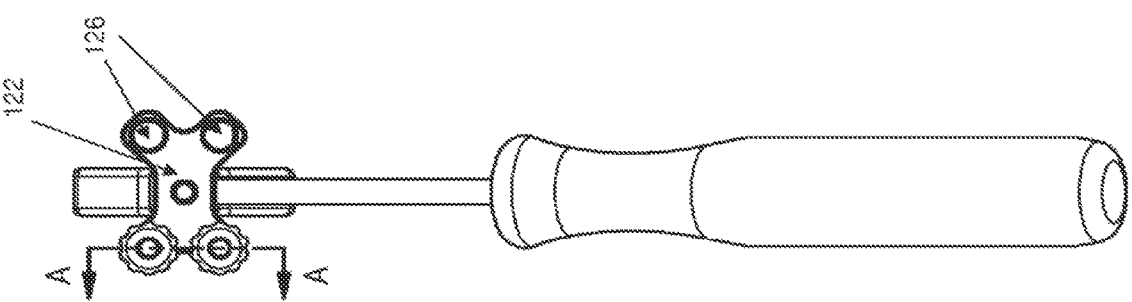
FIG. 11A is a back view of a bone drill guide showing two sleeves inserted into the upper and lower peripheral guide bores on the left side of the guide.
Figure 12:
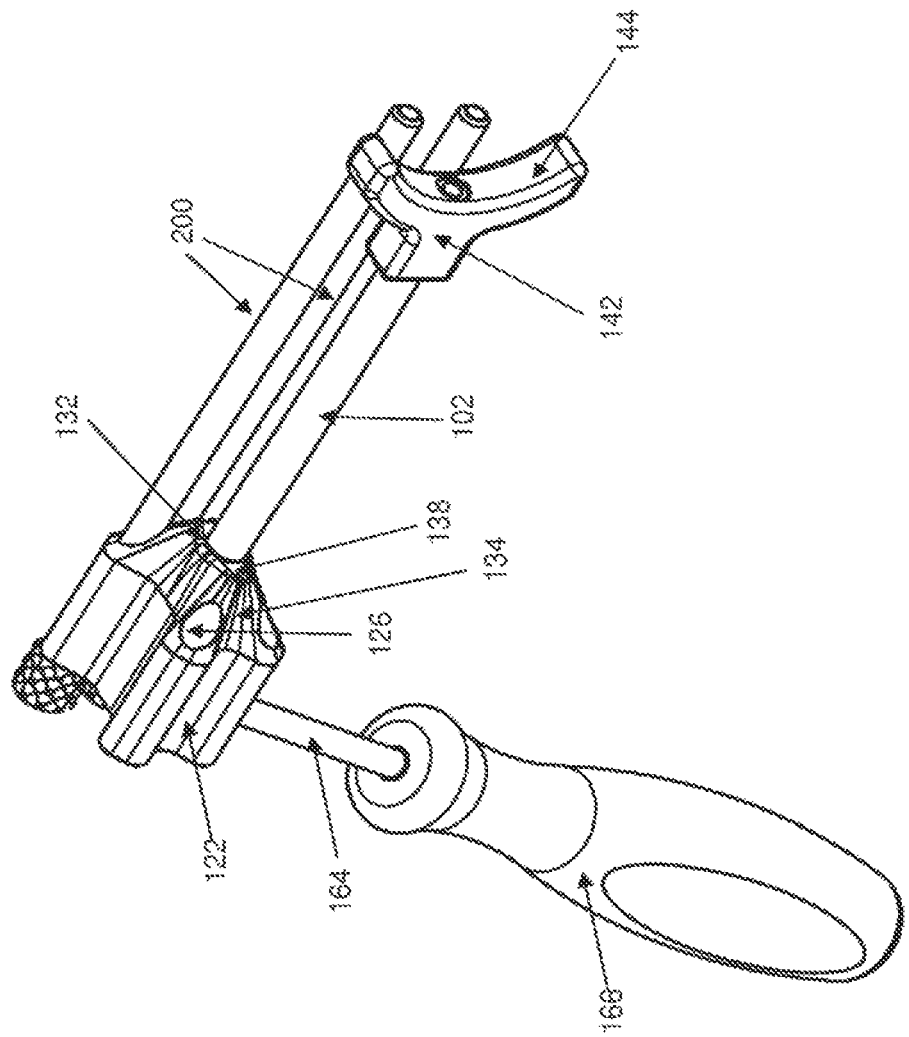
FIG. 12 is a perspective view of the bone drill guide of FIG. 11A.
Figure 13:
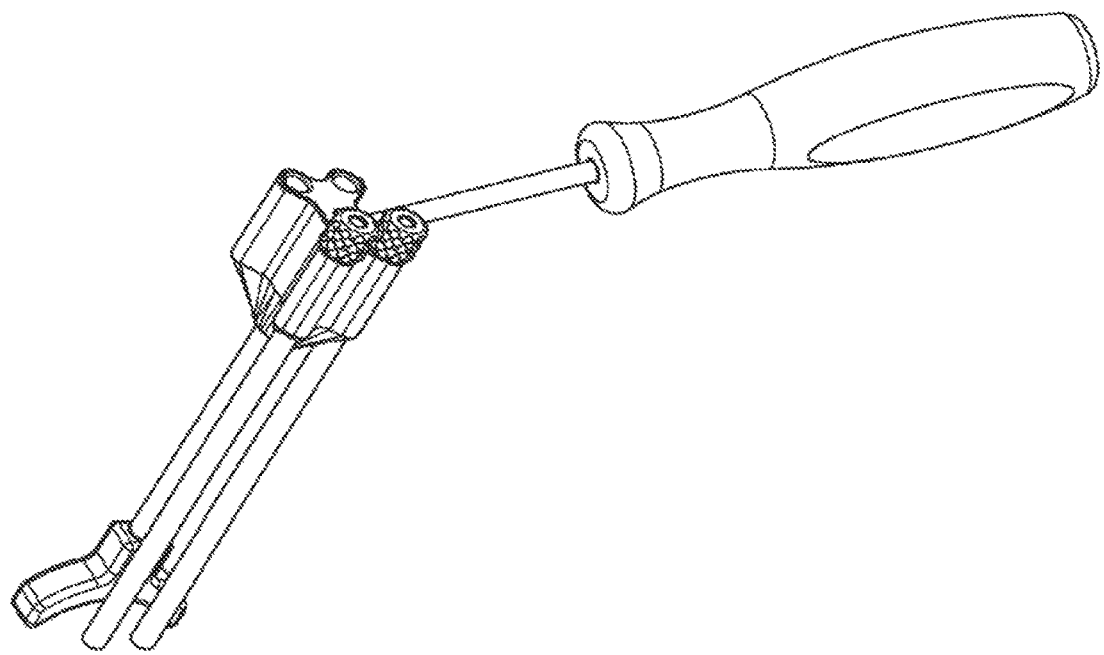
FIG. 13 is a perspective view of the bone drill guide of FIG. 11A.
Figure 14:
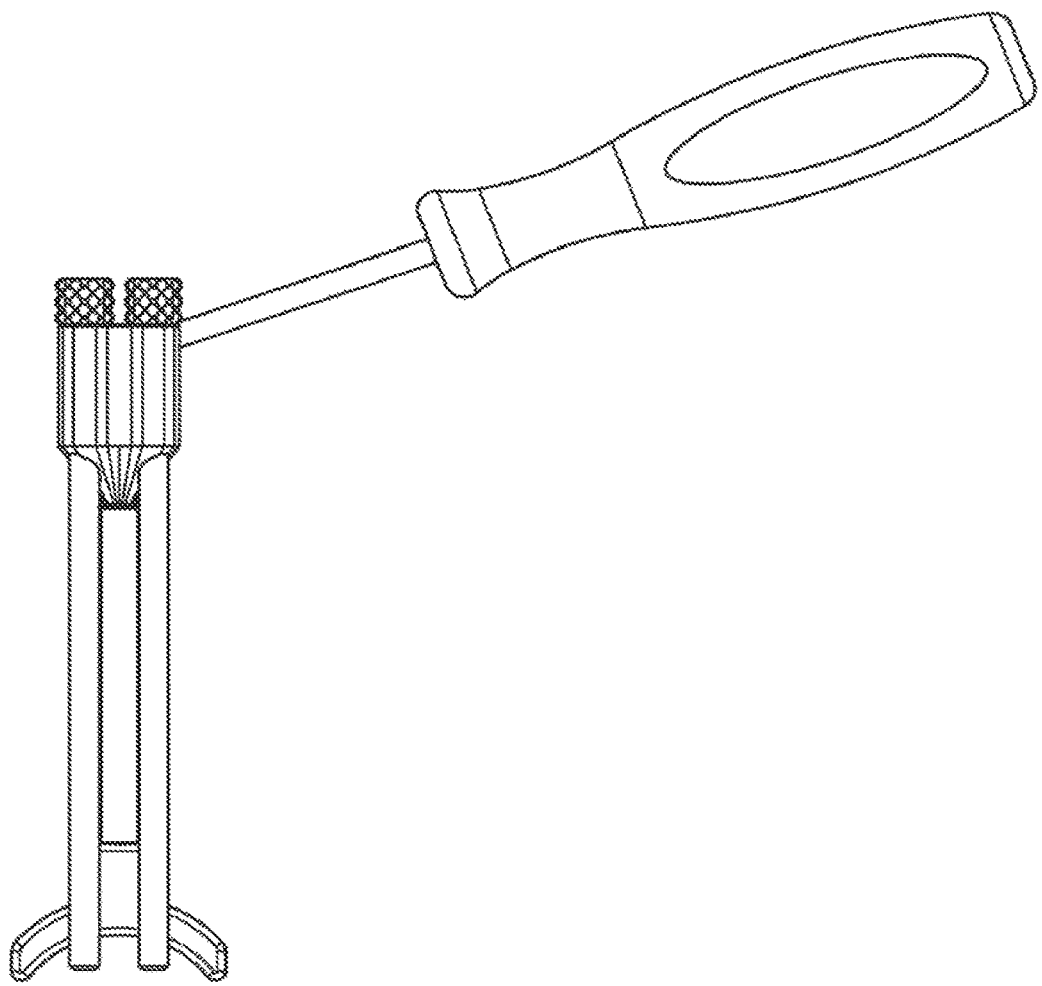
FIG. 14 is a left side elevation view of the bone drill guide of FIG. 11A.
Figure 15:
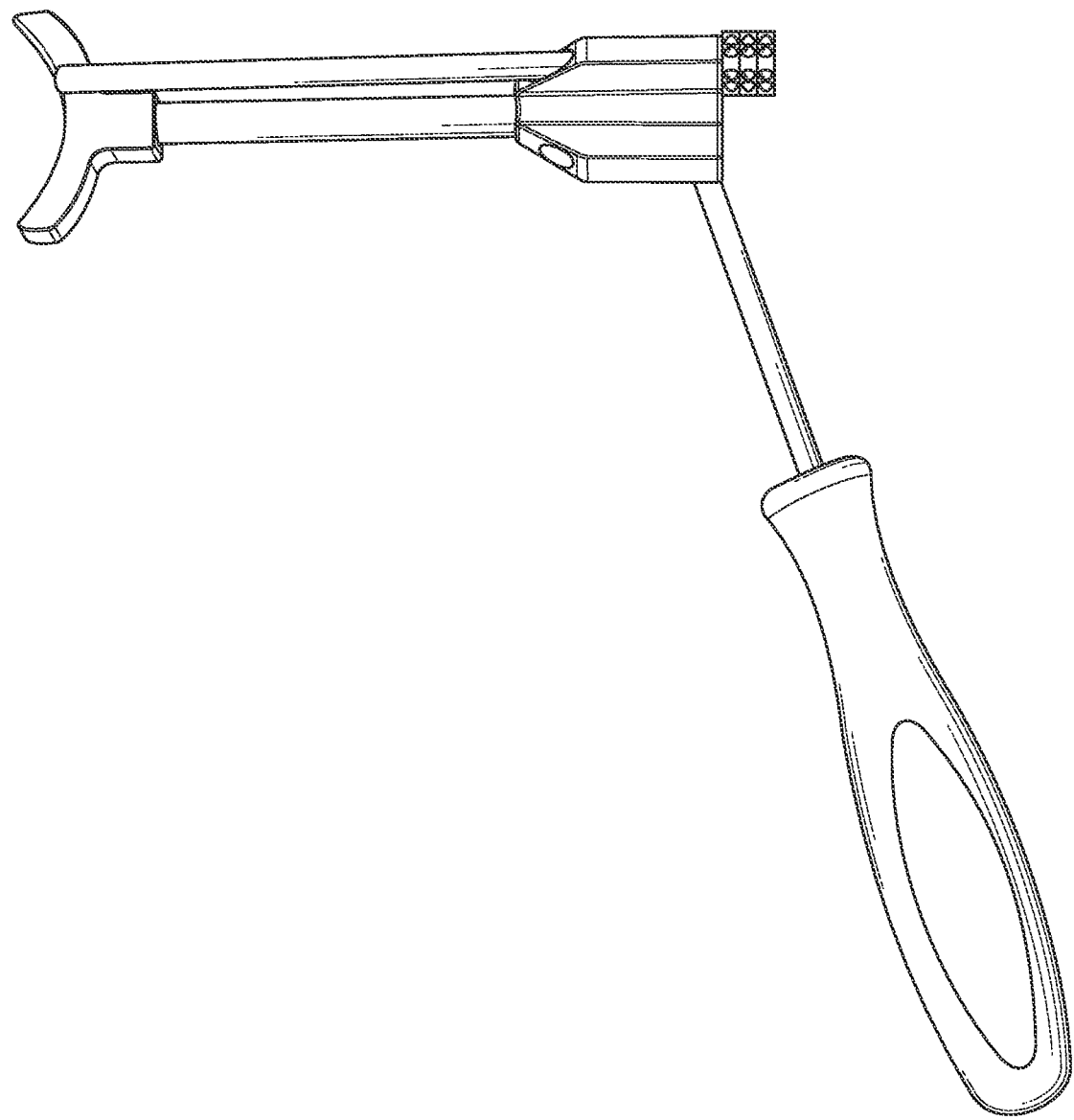
FIG. 15 is a photograph showing a left side view a bone drill guide showing a single sleeve inserted into the upper left peripheral guide bore.
Figure 16:
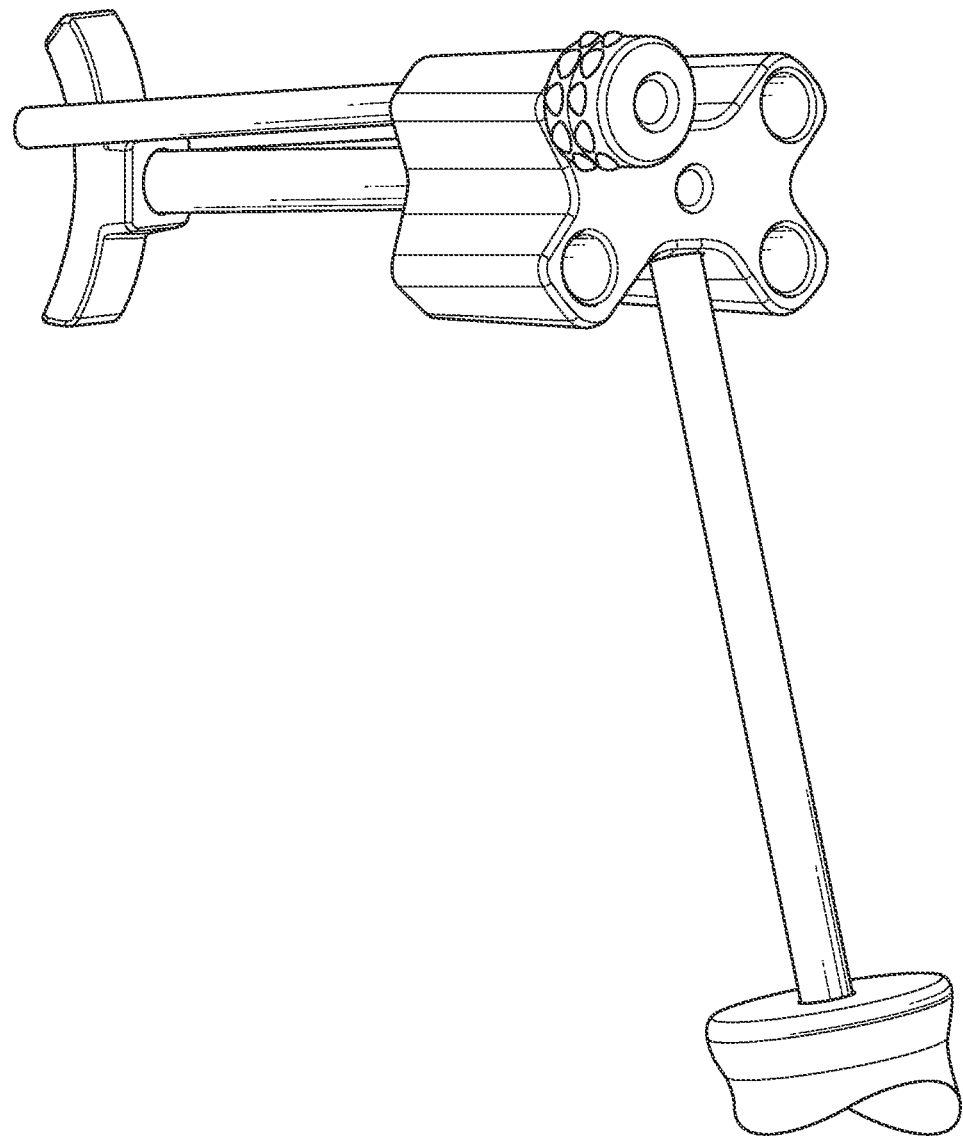
FIG. 16 is a photograph showing a perspective view of the bone drill guide of FIG. 15.

FIGS. 8A and 8B show bottom and top views, respectively, of bone drill guide 100. FIGS. 9A and 9B show back and front views, respectively, of bone drill guide 100.

Functional Design

The length of a bone drill guide of the invention may be varied by increasing or decreasing the length of shaft 102, guide base 122, and/or arcuate element base 150 (see FIG. 1A). For example, length A' (see FIG. 2A) of shaft 102, length K' (see FIG. 3D) of guide base 122, or length A' (see FIG. 4A) can be varied singly or in combination. The dimensions of other elements can be scaled proportionally, e.g., length C' (see FIG. 2A) of proximal inset 110 of shaft 102 or length A' (see FIG. 2A) of shaft 102 can be scaled to account for changes in the length K' of guide base 122. The length of the device could be modified to accommodate use of bone drill guide 100 with differently-sized bones, for differently-sized operators, or to accommodate different devices such as guide wires, guide pins, drill bits, etc.

Guide base 122 is amenable to modification in order to change the number and/or location of peripheral guide bore(s) 126 in relation to interior channel 182. See, e.g., FIGS. 35A-35F for exemplary modifications of the guide base with different numbers (e.g., 1 or 2) and positioning of peripheral guide bores 126. For example, the distance between the central points of peripheral guide bores 126 in relation to each other or in relation to interior channel 182 can be varied depending on the size or dimensions of a given bone. Another exemplary modification is to increase or decrease the distance between the central points of peripheral guide bore(s) 126 in relation to interior channel 182. These modifications can involve further modifications to guide base 122 itself, including, e.g., modifications to its width O' (see FIG. 3F) or height L' (see FIG. 3D), the position of guide wing(s) 127, etc. For example, the width R' (see FIG. 3G) of guide wing(s) 127 can be changed in order to accommodate more than one peripheral guide bore 126. In some embodiments, guide base 122 can be modified to accommodate use of bone drill guide 100 with differently-sized bones, to accommodate different devices, for example guide wires, guide pins, drill bits, sleeves, measuring devices, etc. In some embodiments, guide base 122 may be designed to facilitate removal from bone drill guide 100, for example, to allow a first guide base 122 of bone drill guide 100 to be replaced with a second guide base 122 with a different number and/or spatial arrangement of peripheral guide bores 126.

Arcuate element 142 can be modified to change how the device seats against bone. The shape of arcuate element 142 can be varied to optimize how bone drill guide 100 seats against bone(s). For example, the curvature of concave face 144 of arcuate element 142 can be varied based on population data on the average or median dimensions of the desired bone, for example by varying radius r, arc length L, or central angle θ of concave face 144 (see FIG. 34B). The curvature of arcuate element 142 can be designed to engage any identifiable convex surface on a bone. For example, the curvature of arcuate element 142 can be designed to engage the calcaneus, tibia, femur, pelvis, humerus, radius and ulna, scapula, tarsals, phalanges, and metatarsals. Bones can have different shapes along their lengths or widths. For example, the body of the femur is substantially cylindrical, with a curved lower extremity at its distal part that articulates with the tibia and patella, and a proximal region that includes the greater trochanter as well as the neck and head. Accordingly, the bone drill guides of the invention can be designed with arcuate elements capable of interfacing with specific anatomical features of bone. e.g., the greater trochanter of the femur. Arcuate element 142 can be designed to confer adjustability to the curvature of concave face 144, for example, using hinges, ratchets, or other mechanisms. Arcuate element 142 can be designed for interchangeability, such that it can be removed from bone drill guide 100, for example, and replaced with a different arcuate element 142 having a different curvature or size. It is to be understood that the bone drill guides can also be modified to engage against any identifiable concave surfaces on a bone. In these embodiments, the position of concave face 144 and convex face 146 of arcuate element 142 may be reversed such that convex face 146 contacts the bone. The curvature of arcuate element 142 in these embodiments may also be adjustable as described above. Arcuate element 142 may also be designed to engage against any identifiable substantially flat surface on a bone. The dimensions of handle 162, including handle shaft 164 and handle grip 166, can by modified to change the ergonomics of the device, for comfort, for increased grip, etc. For example, the material of the grip can be changed, or grooves sized to accommodate different fingers can be added. Other elements of handle 162 can also be modified, for example, length A' (see FIG. 5A) of handle shaft 164 can be varied in order to change the position of guide base 122 in relation to the handle.

Sleeves

Structure

Referring to FIGS. 10A-10B, 11A-11B, 12, 13, and 14, sleeve 200 can be slidably inserted into a peripheral guide bore 126 of guide base 122. In certain embodiments, guide base 122 can accommodate several sleeves 200, each of which can be inserted into an individual peripheral guide bore 126. Proximal end 202 of sleeve 200 can abut proximal end 128 (see FIG. 3E) of guide base 122. Proximal end 202 of sleeve 200 can have knurls 204, which can aid in gripping sleeve 200. Channel 206 passes through proximal end 202 and distal end 210 of sleeve 200, and is sized for slidable insertion of hardware or devices including guide wires. For example, channel 206 of sleeve 200 can be sized to accommodate guide wires or pins for 2.0 mm bone screws or implants to a range of 18 mm for hip nail guidance. Channel 206 of sleeve 200 can have an inner diameter in the range of about 1 mm to about 40 mm, e.g., 1 mm, 2 mm, 3 mm, 4 mm, 5 mm, 6 mm, 8 mm, 10 mm, 12 mm, 14 mm, 16 mm, 18 mm, 20 mm, 25 mm, 30 mm, 35 mm, 40 mm, or a value in a range spanning any of the preceding values, and preferably about 4.2 mm. Sleeve 200 can have a length in the range of about 80 mm to about 220 mm, e.g., 80 mm, 100 mm, 110 mm, 120 mm, 130 mm, 140 mm, 150 mm, 160 mm, 170 mm, 180 mm, 190 mm, 200 mm, 220 mm, or a value in a range spanning any of the preceding values, and preferably about 144 mm.

Operation

The bone drill guides of the invention can be used in orthopedic surgery and provide several advantages as compared to prior known bone drill guides. In particular, the bone drill guides allow for firm seating against a bone while still allowing translational and rotational movement during the determination of the appropriate or correct position for insertion of hardware into the bone, making it significantly easier to correctly position the bone drill guides of the present invention compared to prior known drill guides. In several embodiments the bone drill guide is capable of being seated firmly against a bone. Prior known drill guides seat poorly against bones, and often slip off of bone, especially when angulation or translation of the guide is required. Arcuate element 142 of the present drill guide allows for firm seating against a bone during a surgical procedure, while still allowing for translational and rotational movement of the bone drill guide along the bone, if necessary. This reduces the likelihood of unwanted slippage in the slippery environment of a surgical operation while the operator is determining the appropriate location to insert guide wires or other hardware, and allows for ease of adjustment during the operation. Once an appropriate position has been determined and obtained, which may be facilitated by the use of X-rays, firm seating of the drill guide against the bone allows for secure insertion of guide wires and/or other devices into the bone.

Arcuate element 142 is one feature that especially allows for this firm but adjustable seating against bone. In several embodiments of the invention, concave face 144 of the arcuate element 142 is specifically sized to fit snugly against the bone into which an operator desires to insert one or more devices. In preferred embodiments, the curvature of the concave face substantially matches the curvature of the bone in such a manner that arcuate element 142 does not easily slip off the bone.

In some embodiments, concave face 144 has a fixed curvature that allows it to firmly seat against one type of bone. In certain embodiments, concave face 144 has a fixed curvature that allows it to firmly seat against several different types of bone (e.g., 2, 3, 4, 5, 6, or more different types of bone), allowing bone drill guide 100 to be used in procedures on different bones, for example, for inserting hardware into different bones in separate procedures or into several different bones during the course of a single procedure.

In certain embodiments, arcuate element 142 is removable from the drill guide, allowing an operator to customize the bone drill guide 100 with multiple arcuate elements 142 of different sizes or shapes selected for a particular patient, or for inserting guide wires, drill bits, or other hardware into multiple different types of bone. In other embodiments, concave face 144 has a curvature that can be adjusted to allow it to firmly seat against several different types of bone, thereby allowing an operator to use the drill guide on multiple bone types during a single procedure without changing the arcuate element.

In one mode of operation, an operator can seat the bone drill guide of the invention against a bone by grasping handle grip 166 by hand and guiding the attached bone drill guide to a desired region of the bone. The operator can position concave face 144 of arcuate element 142 on the bone and, by applying force, can keep arcuate element 142 at that position on the bone. The design of arcuate element 142 allows the use of less force to keep the bone drill guide seated compared to prior known drill guides which lack this feature. To change the position of the guide element, an operator can grasp handle 162 by holding handle grip 166 while keeping concave face 144 juxtaposed against the bone, followed by moving the bone drill guide in a desired direction. The bone drill guide position can be translated along the longitudinal axis of a bone by directing handle 162 in a manner that will cause sliding of arcuate element 142 along the bone. Angulation can be achieved, for example, by pulling up or pushing down on handle 162, while keeping concave face 144 in the same position along the longitudinal axis of the bone. The bone drill guides of the invention can be grasped with one or two hands of the operator. In preferred embodiments, the operator uses one hand to keep the bone drill guide at a desired position while using another hand to perform other tasks, including inserting guide wires or other devices or hardware into interior channel 182 or through a sleeve 200 placed inside a peripheral guide bore 126, or operating a rotational driver e.g., a drill or a screwdriver. In other aspects, one operator may hold the bone drill guide at a desired position while another operator performs other tasks, including inserting guide wires or other devices or hardware into interior channel 182 or through a sleeve 200 placed inside a peripheral guide bore 126, or operating a rotational driver e.g., a drill or a screwdriver.

Once an operator has positioned a bone drill guide of the invention at a desired location, the operator can insert devices into a bone through interior channel 182, peripheral guide bores 126, or sleeves 200 that have been slidably inserted into peripheral guide bores 126. In several embodiments, a guide wire is placed first through interior channel 182, followed by subsequent guide wires being inserted through one or more sleeves 200 placed in peripheral guide bores 126.

Many paired bones on either side of the sagittal plane of the body are substantially mirror images of one another. For example, the left femur is substantially a mirror image of the right femur. In several embodiments, a bone drill guide of the invention can be used to insert hardware into a bone on either anatomical side of the body, e.g., without requiring any changes or modifications to the bone drill guide. For example, an operator can position a drill guide of the invention against a defective bone, and then make use of peripheral guide bores 126 that are designed for the appropriate anatomical side of the body (e.g., the left or right side) on which the defective bone resides. In some embodiments, an operator can select from several groupings of peripheral guide bores 126 that are designed to be used on either the left or right anatomical side using knowledge of anatomy to insert guide wires or other devices into a bone.

Insertion of guide wires into the appropriate or correct position in the bone is typically monitored, for example, by X-ray or fluoroscopy. Due to the difficulty of inserting guide wires or other hardware into a correct or appropriate position using prior known bone drill guides, this process often is one of the longest steps in a given operation. This is undesirable because the time a subject is exposed to X-rays should be minimized in order to prevent excessive or unnecessary exposure to harmful radiation. It is also undesirable economically, e.g., due to the high cost of operating room time. The bone drill guides of the invention can be used with X-rays or similar imaging approaches. When used with a lateral X-ray view, interior channel 182 and/or peripheral guide bores 126 of bone drill guide 100 can function as sights to aid an operator in positioning bone drill guide 100 at a correct or desirable location. This feature, along with the bone drill guides' firm but adjustable seating against bone, significantly reduces the amount of time needed to accurately position the bone drill guide and hardware. Positioning the bone drill guides of the invention at a correct or desirable site and orientation in relation to a bone in conjunction with X-rays can be performed within approximately 1 min, whereas this step can take up to 15 min using prior known bone drill guides. In preferred embodiments, the cross-section of the bone drill guide allows for unimpeded visualization of the femoral head in the lateral radiographic view. In prior known bone drill guides, the cross-section of the guide blocks this radiographic view, making precision placement difficult.

In some embodiments, the bone drill guides of the invention feature one or more pin hole(s) 143 in arcuate element 142. This feature facilitates proper guide wire positioning and drilling into the bone and aids in stabilization of the bone drill guide on the bone (e.g., the femur). In some embodiments, a device (e.g., a guide wire or pin) may be inserted through one or more pin hole(s) 143 into soft tissues (e.g., under the vastus intermedius and along the surface of the femoral neck into the femoral head). The guide wire may be inserted through pin hole(s) 143 in the direction of the arrows in FIG. 36A. In other embodiments, pin hole(s) 143 may be used to aid in positioning of the bone drill guide along the bone without insertion of a device, for example, by allowing for visual determination of positioning of the bone drill guide on a bone.

Often, multiple pieces of hardware are inserted into a bone during a procedure. The bone drill guides of the present invention are designed to allow for sequential insertion of multiple pieces of hardware into a bone at defined relative positions and orientations. The design of guide base 122, in particular the positioning of peripheral guide bore(s) 126 relative to interior channel 182, allows for the insertion of hardware at positions and orientations that have been designed specifically for use with a wide variety of bones and procedures. In several embodiments, the bone drill guide is configured so that peripheral guide bores are oriented such that, during use, the devices or hardware inserted into the bone have a mutually parallel relationship relative to each other (e.g., two bone screws can be inserted into bone using the bone drill guide shown in FIG. 9A at the top left and right peripheral guide bores). In other embodiments, the bone drill guide is configured so that peripheral bore guides are oriented such that, during use, devices or hardware inserted into the bone have non-parallel angular relationships relative to each other. Guide base 122 of bone drill guide 100 is designed so that it can accommodate a desired number of guide wires or other hardware at one time through individual peripheral guide bore(s) 126 and/or sleeves 200 inserted into the peripheral guide bores 126. Once an initial guide wire has been inserted into the bone, peripheral guide bore(s) 126 of bone drill guide 100 allow an operator to insert subsequent guide wire(s) at constrained, pre-determined position(s) into the bone relative to the initial guide wire, substantially eliminating much of the guess-work that accompanies current procedures.

In particularly preferred embodiments, the positioning of peripheral guide bore(s) 126 in relation to interior channel 182 of bone drill guide 100 is designed to allow placement of multiple cannulated and fenestrated bone screws into the bone in a manner that is optimized for insertion of flowable media including bone cement into the defective bone. For example, in a procedure to repair a defect (e.g., a fracture) of the femoral neck, the spacing and positioning of peripheral guide bore(s) 126 can ensure that, for example, washers (e.g., compression and inset washers) that are placed beneath the head of bone screw(s), if used during a surgical procedure, do not overlap and that the bone screws are aligned (see, e.g., FIGS. 17-33). Cannulated and fenestrated bone screws and other devices that can be used with the present invention are described, e.g., in U.S. Pat. No. 8,574,273 and PCT/US2014/020678, both of which are incorporated herein by reference in their entirety. A desired number of cannulated and fenestrated bone screws can be introduced into the bone, for example, 1, 2, 3, 4, 5, 6, 7, or more bone screws using the bone drill guide of the invention. In preferred embodiments, 2 or 3 cannulated and fenestrated bone screws can be introduced into a bone at relative positions that are defined by bone drill guide 100. This orientation can be designed to allow for substantially circumferential augmentation of the bone screw(s) by extrusion of a flowable medium (e.g., a calcium phosphate bone cement) that can be injected through the bone screw(s) into the bone. When bone cement is used, this can create a favorable internal buttress after hardening that greatly strengthens the structural integrity of the defective bone (see FIG. 32 showing circumferential augmentation of the bone screw). The bone screws can be used with other devices known in the art, for example, metal bone plates, which can be attached to the exterior of the bone to provide support (e.g., bone plates for the lateral cortex on the periosteal surface of the femur). In some embodiments, the internal buttress formed by the bone cement due to the positioning and arrangement governed by bone drill guide 100 enables use of smaller bone plates than would otherwise be necessary. In other embodiments, the internal buttress obviates the need for any external devices, such as a bone plate.

Kits

The invention also features a kit that includes one or more of i) a bone drill guide of the invention and ii) a sleeve of the invention. The kit may, optionally, include one or more guide wires, bone screws (e.g., the bone screws of U.S. Pat. No. 8,574,273 or PCT/US2014/020678, the entirety of which are incorporated herein by reference), an injection device (e.g., a syringe), a powder of a flowable medium (e.g., a self-hardening bone cement powder), a drill bit(s), and a physiologically acceptable fluid for hydrating the bone cement powder. The flowable medium may be provided in the form of a powder that may be hydrated with a pharmaceutically acceptable fluid (e.g., water, serum, or saline) prior to use, or in a ready to use form (e.g., a paste, putty, or slurry). The kit may be packed with other devices, for example, those described in U.S. Pat. No. 8,574,273 and PCT/US2014/020678 (e.g., the screws, manifold, etc.). The kit may optionally provide additional or extra components of the bone drill guide, including one or more additional arcuate elements designed for different bones, shafts of different lengths, guide bores with different numbers or arrangements of peripheral guide bores, or different sized or shaped handle shafts or handle grips. For example, the kit may include a first arcuate element 142 having radius r of 20.8 mm, and a second arcuate element 142 having radius r of 15 mm. In other embodiments, the kit may include a series of arcuate elements 142 having different lengths, widths, heights, and/or curvatures. In other embodiments, the kit may include a first shaft 102 having a length of 127 mm and a second shaft 102 having a length of 100 mm. In other embodiments, the kit may include a series of shafts 102 having different lengths. In other embodiments, the kit may include a first guide base 122 having 4 peripheral guide bores 126, and a second guide base 122 having 8 peripheral guide bores 126. In other embodiments, the kit may include a series of guide bases 122 that each have different numbers or arrangements of peripheral guide bores 126. Other components that may be optionally included in the kit include, for example, measuring devices (e.g., guide wire depth gages), rotational drivers, etc. The kit may further include instructions for use of the bone drill guide and other constituents of the kit to treat a bone defect (e.g., subarticular fracture, a defect of the spine or vertebra, or a defect of the radius, ulna, fibula, clavicle, humerus, pelvis, femur, patella tibia, talus, calcaneus, navicular, cuneiforms, metatarsals, metacarpals, phalanges, scapula, ankle, or mandible).

Methods of Treatment Using a Bone Drill Guide of the Invention

The bone drill guides of the invention may be used to treat a bone defect in a patient in need thereof. For example, the bone drill guides can be used in any surgical procedure in which accurate placement of an implant (e.g., a device such as a guide wire, pin, screw, or other implant) within bone that involves a central axis of alignment with a concave or convex surface is important for performance or desired by an operator, including but not limited to total hip arthroplasty (THA) cup placement, bilateral alignment of spinal pedical implants, and fracture repair in skeletal tissue. In particular, a bone drill guide, when used with guide wires, bone screws, drill bits, components for internal fixation (e.g., intramedullary nails, plate devices, and external fixation pins) and/or other devices, can be used to provide fixation (e.g., compressive fixation) in a patient (e.g., a fracture requiring compression).

Particular bone defects that may be treated using the bone drill guides of the invention include, e.g., any bone deficient region, such as a void, gap, recess, or other discontinuity in a bone. The bone defect may be due to, for example, disease or trauma. The bone drill guides of the invention can be applied, for example, in the repair of periodontal defects, in craniofacial or maxillofacial surgery or reconstruction, in hand surgery, in joint reconstruction, in fracture repair, in orthopedic surgical procedures, and in spinal surgery (e.g., spinal fusion and vertebroplasty). The bone drill guides of the invention may also be used, for example, in osteosynthesis to internally stabilize and/or join bones, e.g., fractured (broken) bones, using e.g., bone screws, which can be used in conjunction with other mechanical devices, such as washers, metal plates, pins, rods, or wires. For example, the bone drill guides of the invention can be used with a guide wire to be used as a guide for drill bits and bone screws to provide fixation (e.g., compressive fixation) of bone defects and bone fractures. In particular, the bone drill guides are useful for the treatment of defects or breaks in large bones. Non-limiting examples of bone fractures include, e.g., stable fractures, transverse fractures, oblique fractures, spiral fractures, comminuted fractures and open and displaced fractures. Exemplary large bones that may require fracture fixation include, e.g., the femur (e.g., a fracture of the femoral neck), tibia, fibula, humerus, ulna, radius, $7^{th}$ and $8^{th}$ ribs, innominate bone (hip bone) and sternum.

The method of treating a patient having a bone defect (e.g., subarticular fracture, a defect of the spine or vertebra, or a defect of the radius, ulna, fibula, clavicle, humerus, pelvis, femur (e.g., a fracture of the femoral neck), patella, tibia, talus, calcaneus, navicular, cuneiforms, metatarsals, metacarpals, phalanges, scapula, ankle, teeth, or mandible) can include the following: a) positioning bone drill guide 100 in proximity to the bone defect; b) inserting a guide wire into the bone at a desired position in proximity to the bone defect, preferably through interior channel 182 of bone drill guide 100; c) optionally inserting additional guide wires into the bone through peripheral guide bore(s) 126 of bone drill guide 100. Guide wires may be inserted, for example, to a depth of about 50 mm to about 130 mm into the bone, e.g., 50 mm, 60 mm, 70 mm, 80 mm, 90 mm, 100 mm, 110 mm, 120 mm, or 130 mm. Subsequent optional steps that can be performed when using bone screws include d) overdrilling one or more guide wires with a drill bit; e) positioning one or more bone screw(s) using the guide wire(s) as a guide so that it contacts the intraosseous space of a bone, and/or, in the treatment of a fracture, spans the fracture line); f) removing the guide wire; and g) introducing a flowable medium (e.g., a bone void filler material, a cement, or a pharmaceutical agent), such as by use of a manifold (e.g., as described in U.S. Pat. No. 8,574,273 or PCT/US2014/020678), into the interior channel of the bone screw, allowing the flowable medium to be extruded through the delivery channels of the bone screw (e.g., the flowable medium is extruded through substantially all or a plurality of the delivery channels, e.g., in substantially equal volumes), and allowing the flowable medium to harden, thereby fixing the bone screw in place. In preferred embodiments, the bone screw is an InnoVision (Memphis, Tenn., USA) N-FORCE FIXATION SYSTEM™ bone screw, for example, InnoVision Catalog Number IN001-25-FS, IN001-30-FS, IN001-35-FS, IN001-40-FS, IN001-45-FS, IN001-50-FS, IN001-55-FS, IN001-60-FS, IN001-65-FS, IN001-70-FS, IN001-75-FS, IN006-25-FS, IN006-25-FS, IN006-30-FS, IN006-35-FS, IN006-40-FS, IN006-45-FS, IN006-50-FS, IN006-55-FS. IN006-60-FS, IN006-65-FS, and/or a bone screw described in U.S. Pat. No. 8,574,273 and PCT/US2014/020678. In less-preferred embodiments, a flowable medium (e.g., bone cement) can be used without a bone screw, for example, by inserting the flowable medium into a hole drilled into the bone using the bone drill guide of the invention. The bone drill guide of the invention may be used, e.g., for maxillomandibular or craniofacial fixation, temporary fixation for repairing a bone defect in a staged reconstruction, glenoid or humeral fixation, patellar fixation, or spine fixation.

In some methods of treatment, pin holes 143 in arcuate element 142 are used to facilitate proper guide wire positioning and drilling and to aid in stabilization of the bone drill guide on the bone (e.g., the femur). In this method, a guide wire or pin is inserted through pin hole 143 (e.g., in the direction of the arrows in FIG. 36A) into soft tissues (e.g., under the vastus intermedius and along the surface of the femoral neck into the femoral head) to allow correct anteversion/retroversion sighting and to properly translate the bone drill guide in the superior and inferior position in reference to the longitudinal aspect of the femoral shaft and femoral neck. In addition to increasing the efficiency of the procedure, this step helps to avoid superior or inferior mispositioning of the bone drill guide and thereby helps to avoid malpositioning the device or implant in the bone, for example, to avoid too superior or inferior placement of the device in the femur.

For vertebral fixation, the bone drill guide may be used to insert guide wires to serve as guides for bone screws, which may be placed within a pedicle, used to anchor an interbody device, used to anchor spinal fusion plates and spacer replacement, used in an osteoporotic vertebra, or positioned in proximity to the spinous processes of adjacent vertebrae.

The method of treatment using a bone drill guide of the invention may also include the insertion of a rod, pin, nail, or bone plate in proximity to the bone defect. One or more of these devices may be used in conjunction with a bone screw or separate from a bone screw.

When the method is performed to provide compressive fixation using bone screws, the method may include, prior to optional step e), i) positioning a washer over the proximal end of the bone screw (near the screw head), ii) inserting the distal end of the bone screw into the bone so that it passes through the fracture line, and iii) tightening the bone screw such that the distal threads of the bone screw provide compressive force that pulls the bone screw head (and the washer) against the surface of the patient's bone.

EXAMPLES

The following examples are to illustrate the invention. They are not meant to limit the invention in any way.

Figure 17:
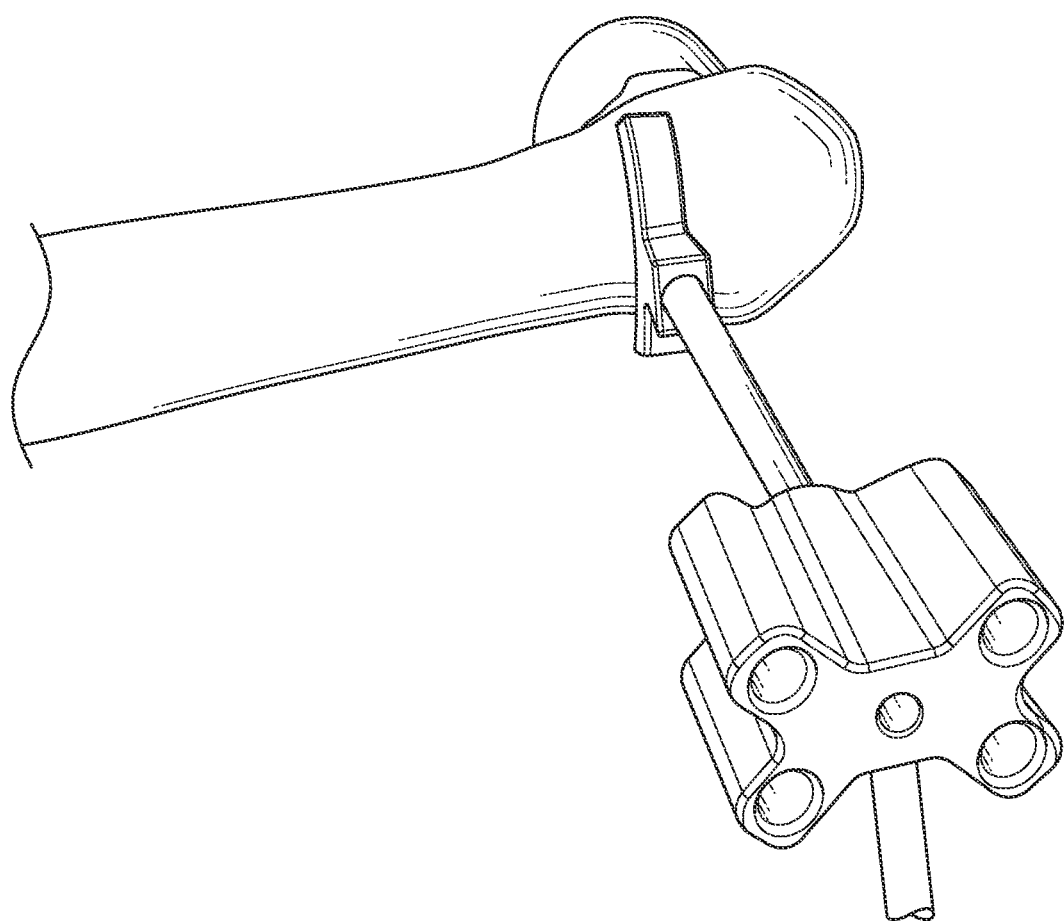
FIG. 17 is a graphic image showing a perspective view of a bone drill guide with its arcuate element contacting the proximal end of a human femur in preparation for insertion of guide wires through the neck of the femur.

Example 1: Use of a Bone Drill Guide of the Invention to Repair a Fracture or Other Bone Defect The bone drill guides of the invention are useful in the repair of a fracture of the femoral neck. As shown in FIG. 17, the bone drill guide is applied to the lateral convex proximal femoral area that has a convexity that matches the curvature of the arcuate element of the bone drill guide. The bone drill guide is translated proximally or distally along the axis of the femur to identify the position to insert the inferior guide wire along the medial inferior calcar of the femoral neck. A trajectory is created by projecting a line in space with the aid of image intensifier radiographic views. The handle is rotated up or down at 90° to the plane of the longitudinal femoral shaft to align the correct anteversion of the femoral head neck axis using the lateral radiographic view of the true lateral of the hip.

Figure 18:
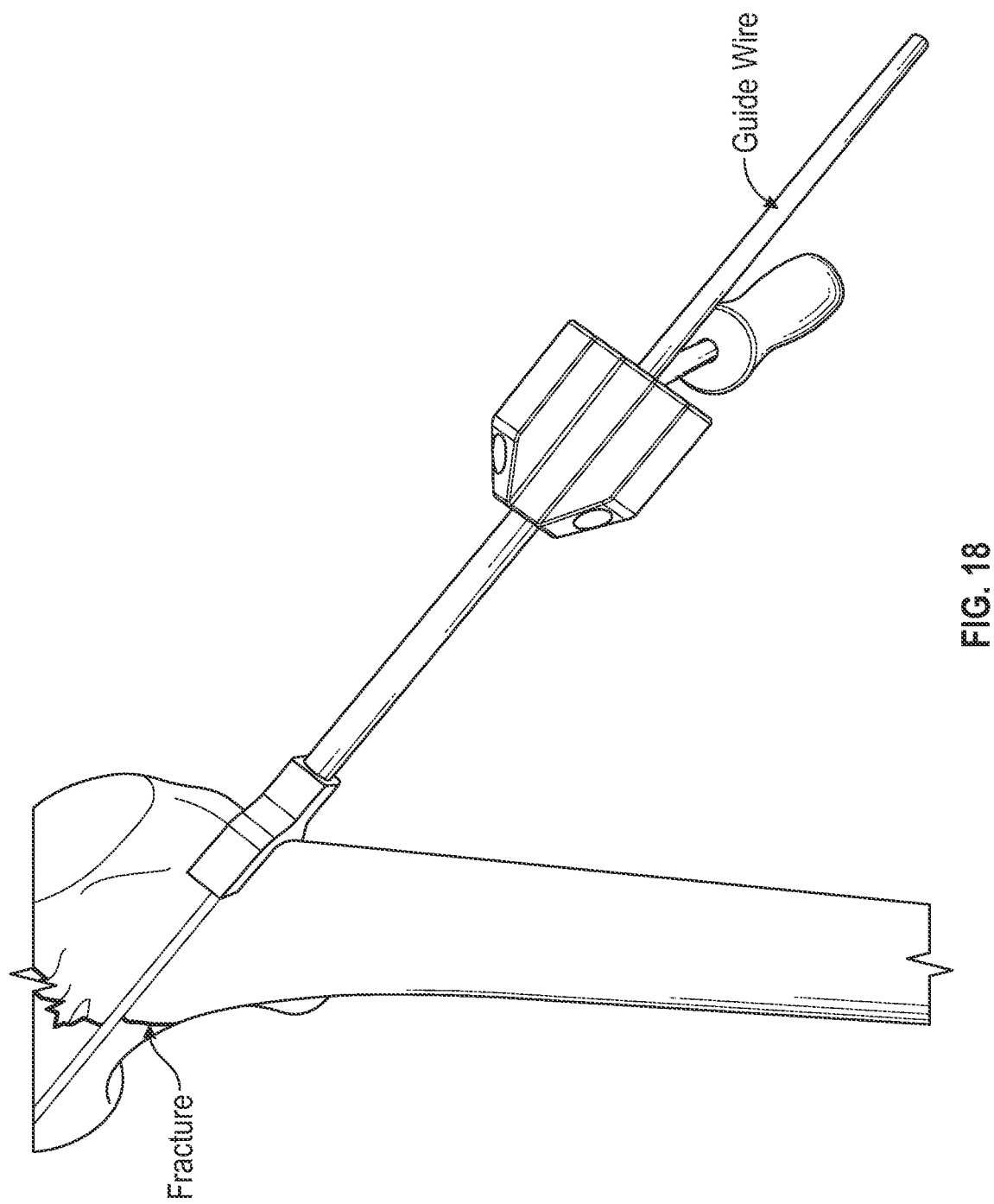
FIG. 18 is a graphic image showing a top view of the bone drill guide of FIG. 17 during insertion of a guide wire along interior channel of the shaft and through a fractured human femur. The femur is shown partially transparent for ease of illustration.

The inferior 3.2 mm guide wire is inserted into the interior channel of the bone drill guide and advanced to within about 10 mm of the articular surface of the femoral head (FIG. 18). The trajectory of the guide wire is maintained by applying slight pressure axially on the guide through the handle. The matching convexity of the lateral femur and concavity of the arcuate element of the bone drill guide provides stability during guide wire insertion into the femur.

Figure 19:
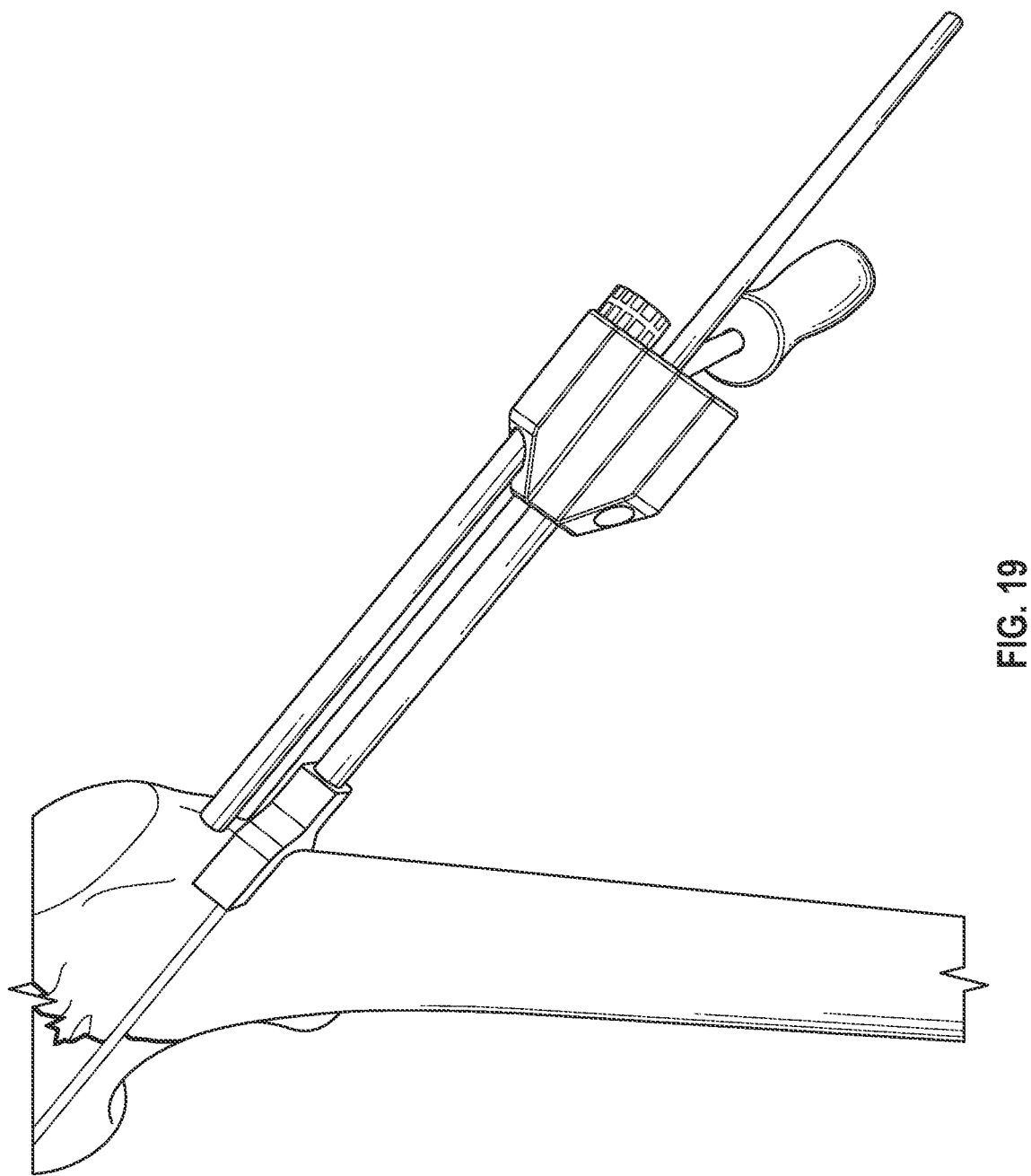
FIG. 19 is a graphic image showing a top view of the bone drill guide of FIG. 18 during insertion of a guide wire into the interior channel and through a fractured human femur. Two sleeves have been inserted into peripheral guide bores on the right side (upper and lower). The femur is shown partially transparent for ease of illustration.
Figure 20:
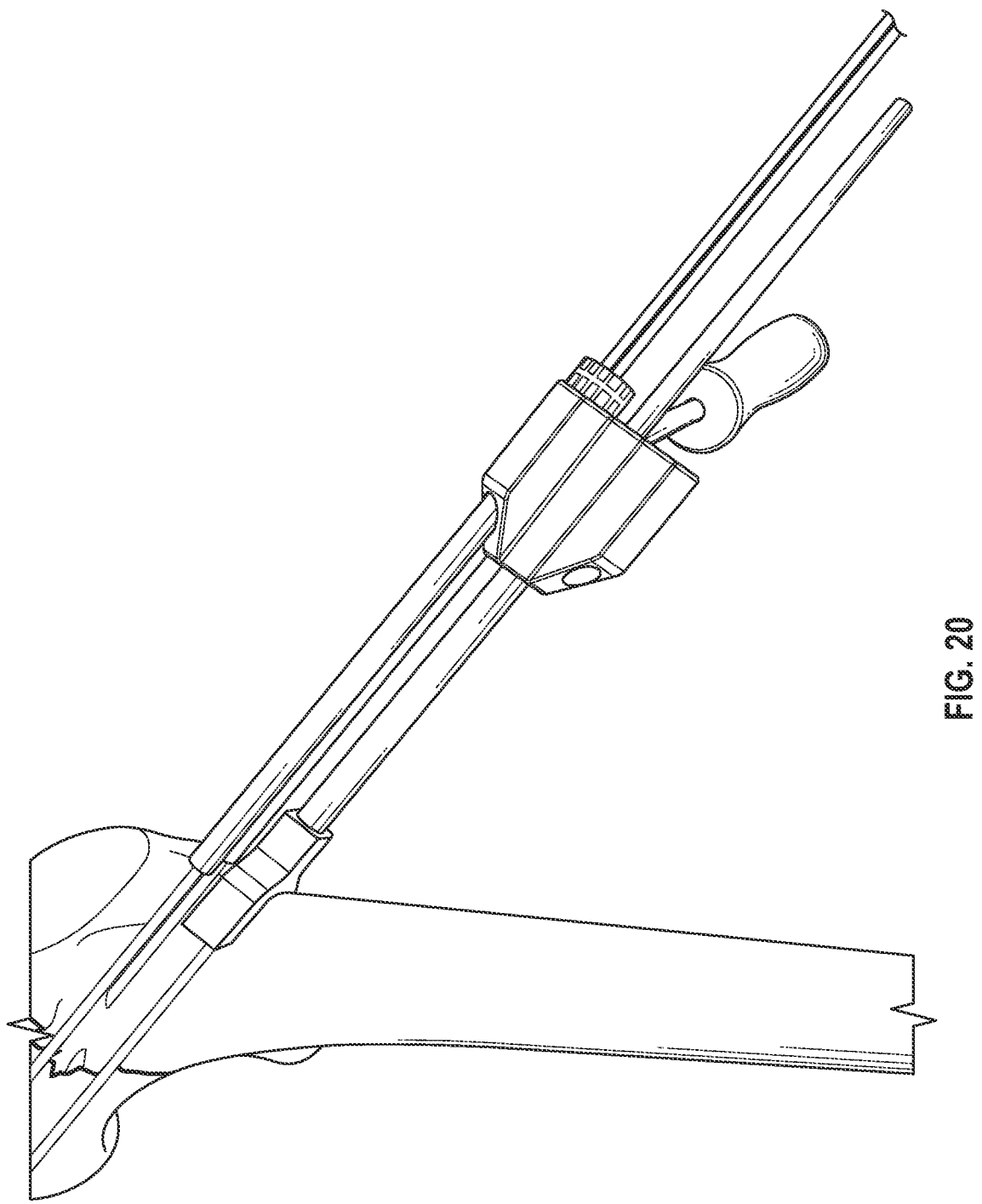
FIG. 20 is a graphic image showing a top view of the bone drill guide of FIG. 19 in which two guide wires have been inserted into upper and lower sleeves on the right side of the guide base and through a fractured human femur. The first guide wire is inserted through the interior channel of the bone drill guide. The second and third guide wires are inserted through the sleeves. The femur is shown partially transparent for ease of illustration.
Figure 21:
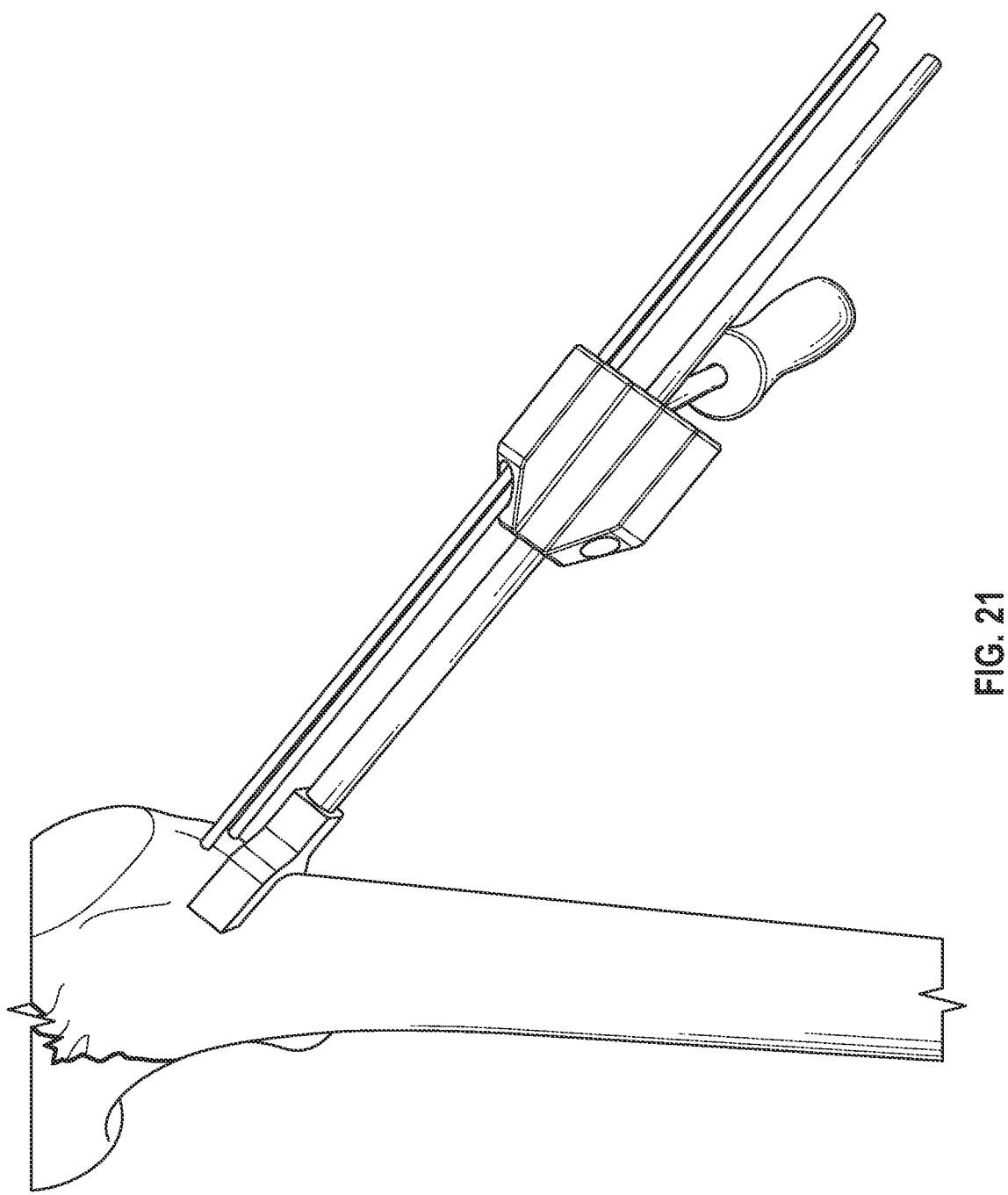
FIG. 21 is a graphic image showing a top view of the bone drill guide of FIG. 20 after the sleeves have been removed. Three guide wires are now inserted into the femur.

For repair of a femoral neck fracture on the left hip, a sleeve is inserted into the anterior superior peripheral guide bore of the bone drill guide (see FIG. 19) so that the guide wire that will subsequently be inserted into the femur through the sleeve will be on the cephalad direction from the reference 3.2 mm guide wire already inserted through the interior channel (FIG. 19). The second 3.2 mm guide wire is drilled into the femur through the superior sleeve inserted into the anterior superior peripheral guide bore of the drill guide (FIG. 20). Rotation of the handle allows the operator to choose the optimal anterior position to ensure containment of the guide wire within the femoral head as proximate to the anterior neck of the femur as possible, which allows for the 7.3 mm diameter of the bone screw that will be inserted in subsequent steps. Next, a second sleeve is inserted into the peripheral guide bore that is posterior to the anterior guide wire that was just inserted, and a third guide wire is drilled into the femur through the sleeve to create a collinear inverted triangle (V) for stability of the fracture (FIG. 20; the second sleeve is not visible in this view). FIG. 21 shows a view of all three guide wires inserted into the femur through the drill guide in a properly aligned and spaced position. The bone drill guide preselects a 60° spacing between bone screws that are inserted along the guide wires. This avoids overlap of implants (including washers) on the lateral cortex of the femur.

Figure 22:
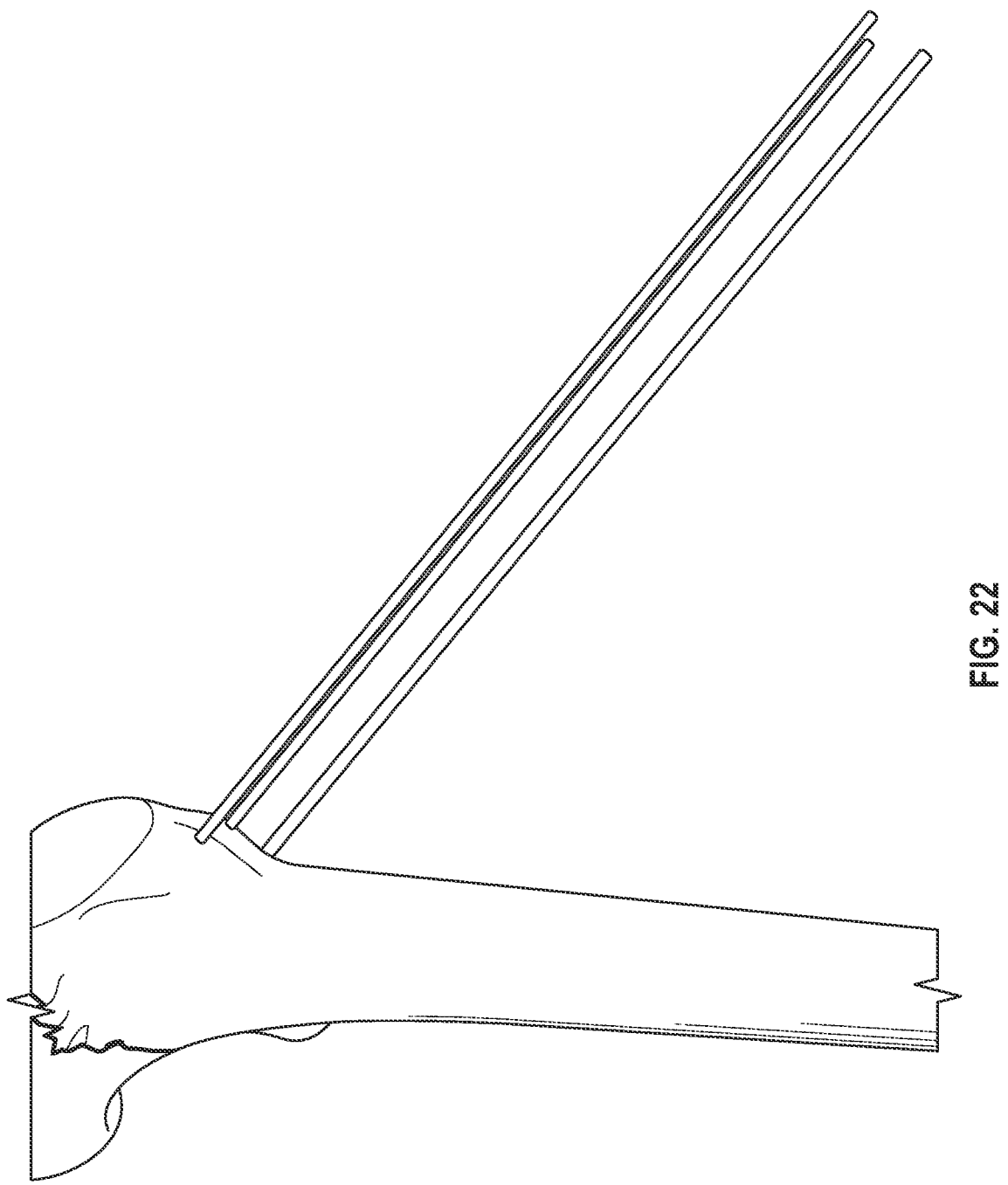
FIG. 22 is a graphic image subsequent to the image of FIG. 21, showing three guide wires inserted into a femur after removal of the bone drill guide.
Figure 23:
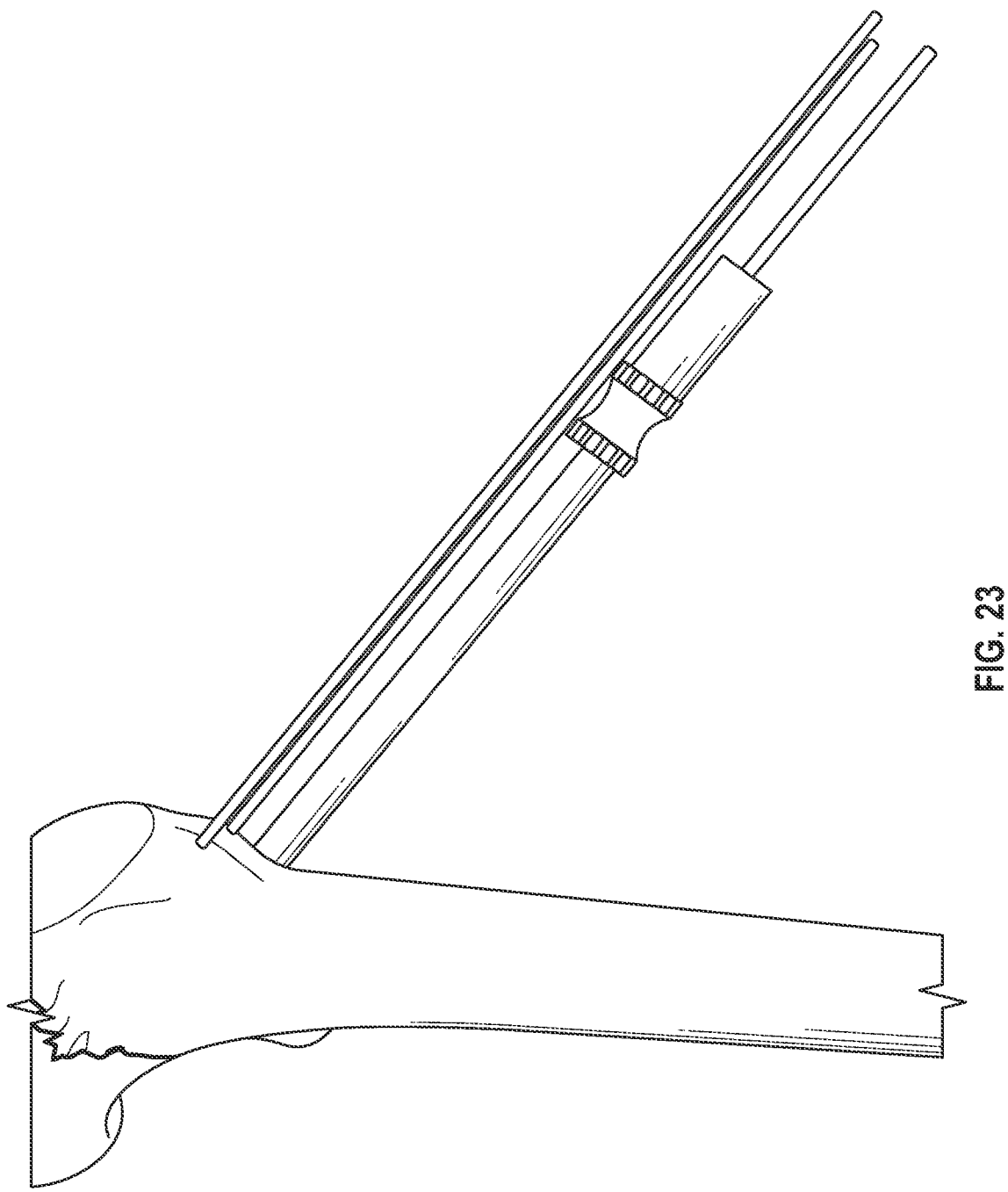
FIG. 23 is a graphic image showing measurement of the insertion depth of guide wires using a drill barrel and a measurement depth gage tool

The bone drill guide is removed (FIG. 22). A 5.5 mm drill guide is inserted over the inferior guide wire, and a depth gauge is attached to determine the length of the guide wire within the femur. This allows the selection of 7.3 mm bone screw of an appropriate length to match the measurement. The length of the two anterior guide wires within the femur can optionally be measured using the same method to select the length of the bone screws that will be inserted along those guide wires.

Figure 24:
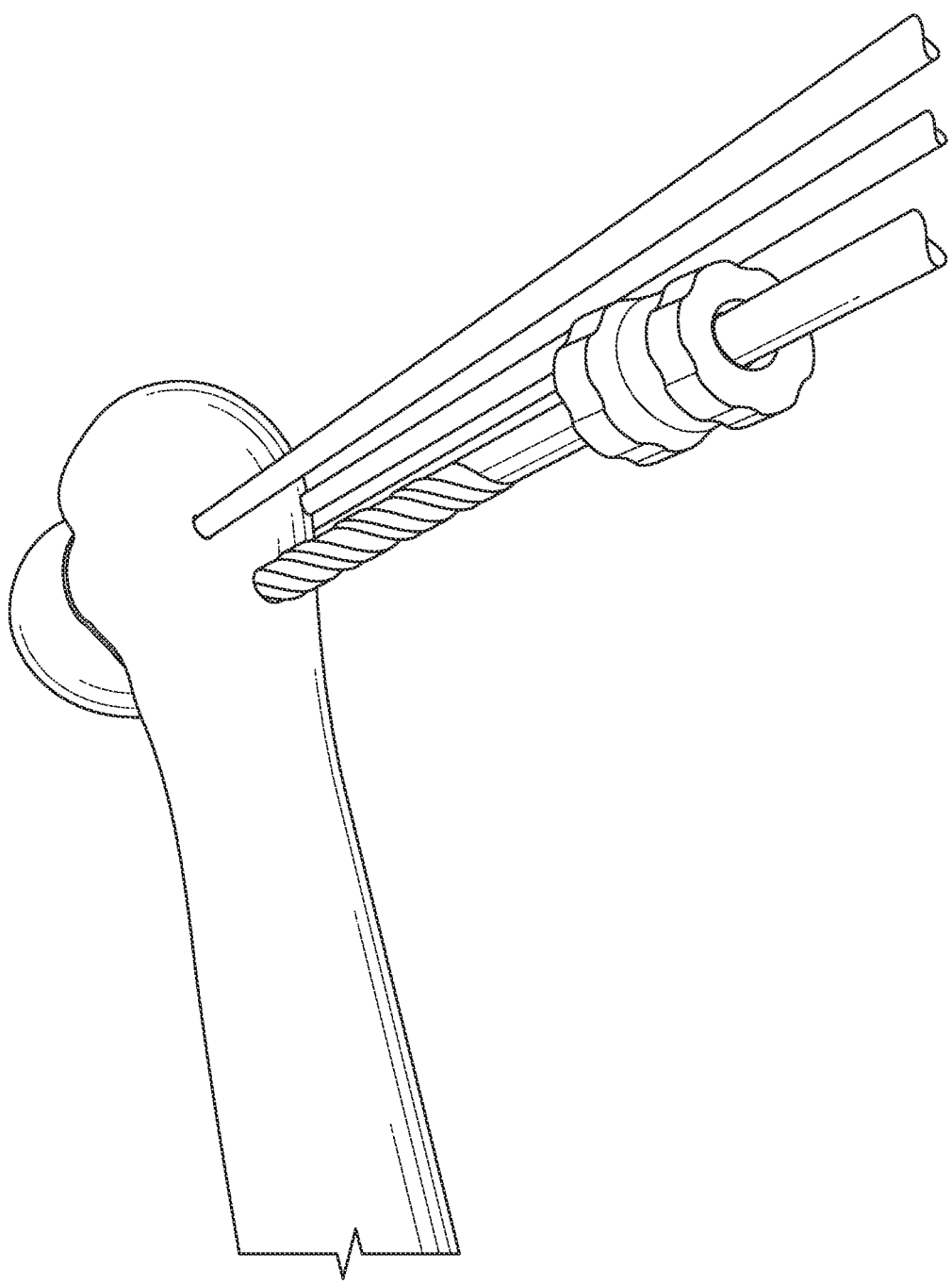
FIG. 24 is a graphic image showing the femur of FIG. 23 after insertion of a cannulated drill bit over one of the guide wires in order to overdrill the guide wire.
Figure 25:
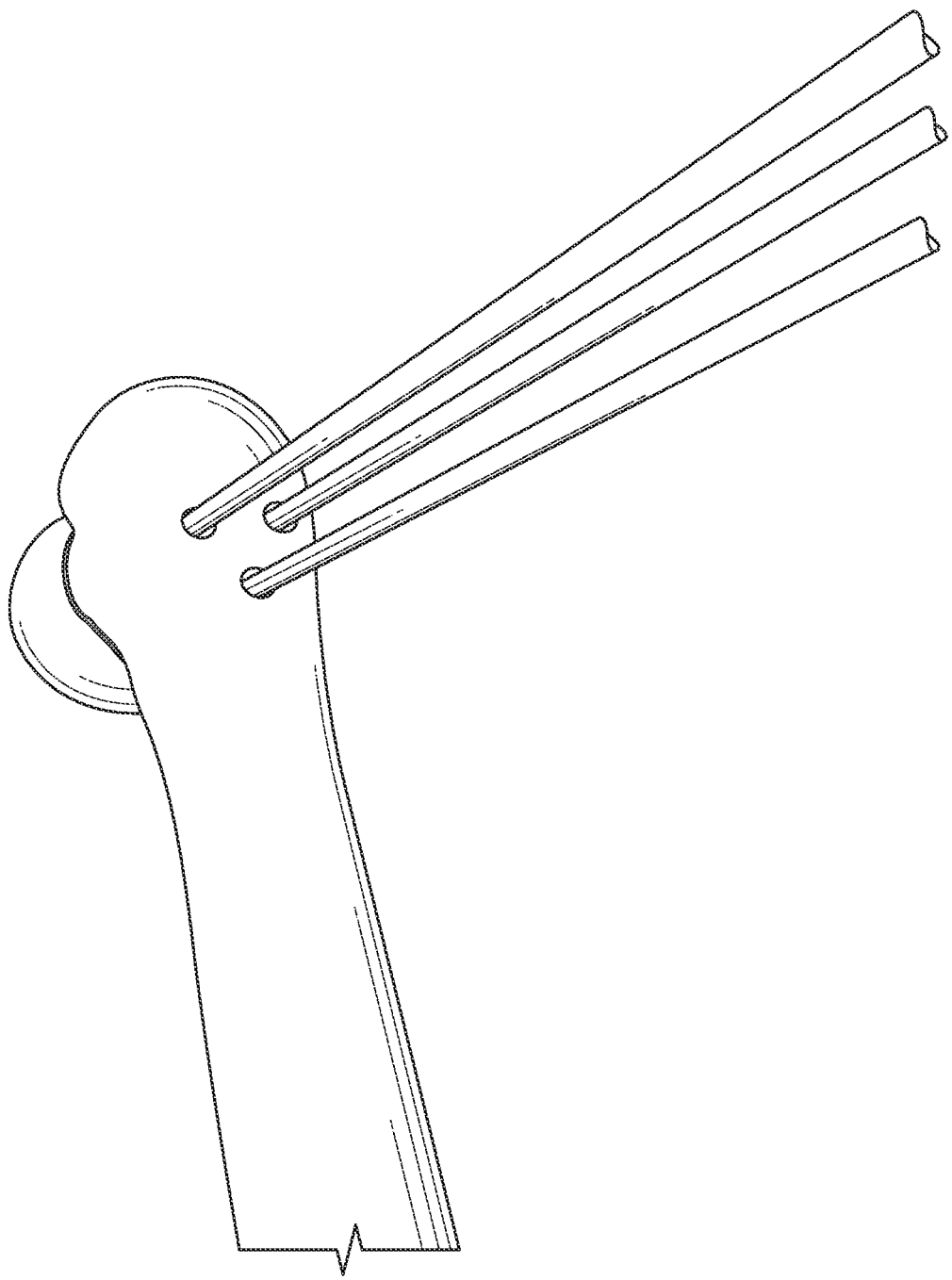
FIG. 25 is a graphic image showing the femur of FIG. 24 after overdrilling of all three inserted guide wires.

A cannulated drill bit is inserted through the 5.5 mm drill guide along the interior guide wire and the measured length of the pin is drilled, taking care not to overpenetrate into the femoral head or articular surface (FIG. 24). Optionally, all of the guide wires of the construct may be overdrilled using the same method if the femoral reduction is stable or provisionally fixed with other temporary devices (FIG. 25). Overdrilling of all three pins without provisional stabilization might induce a loss of reduction in an unstable fracture.

Figure 26:
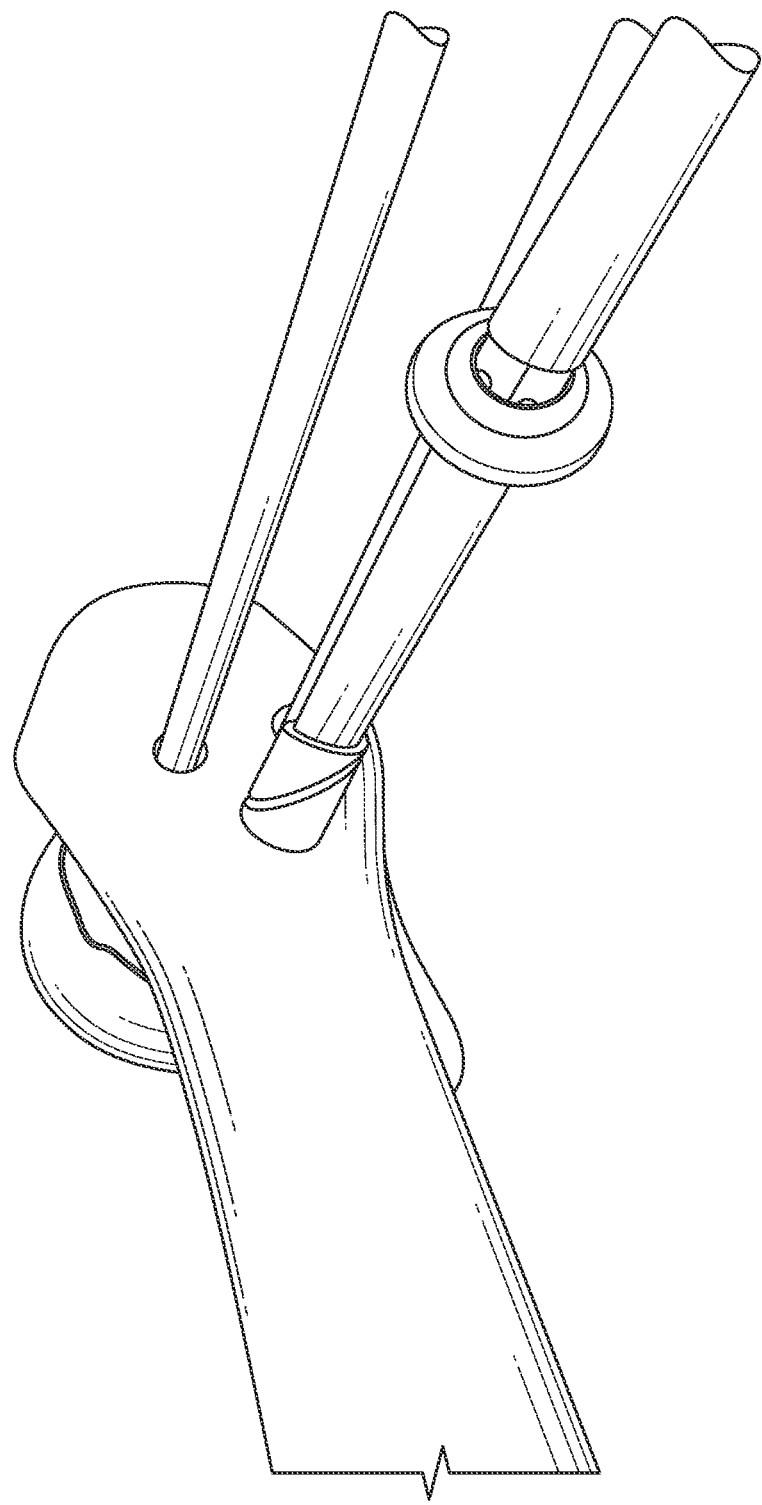
FIG. 26 is a graphic image showing the femur of FIG. 25 showing a rotational driver inserting a cannulated bone screw into the femur along an overdrilled guide wire.
Figure 27:
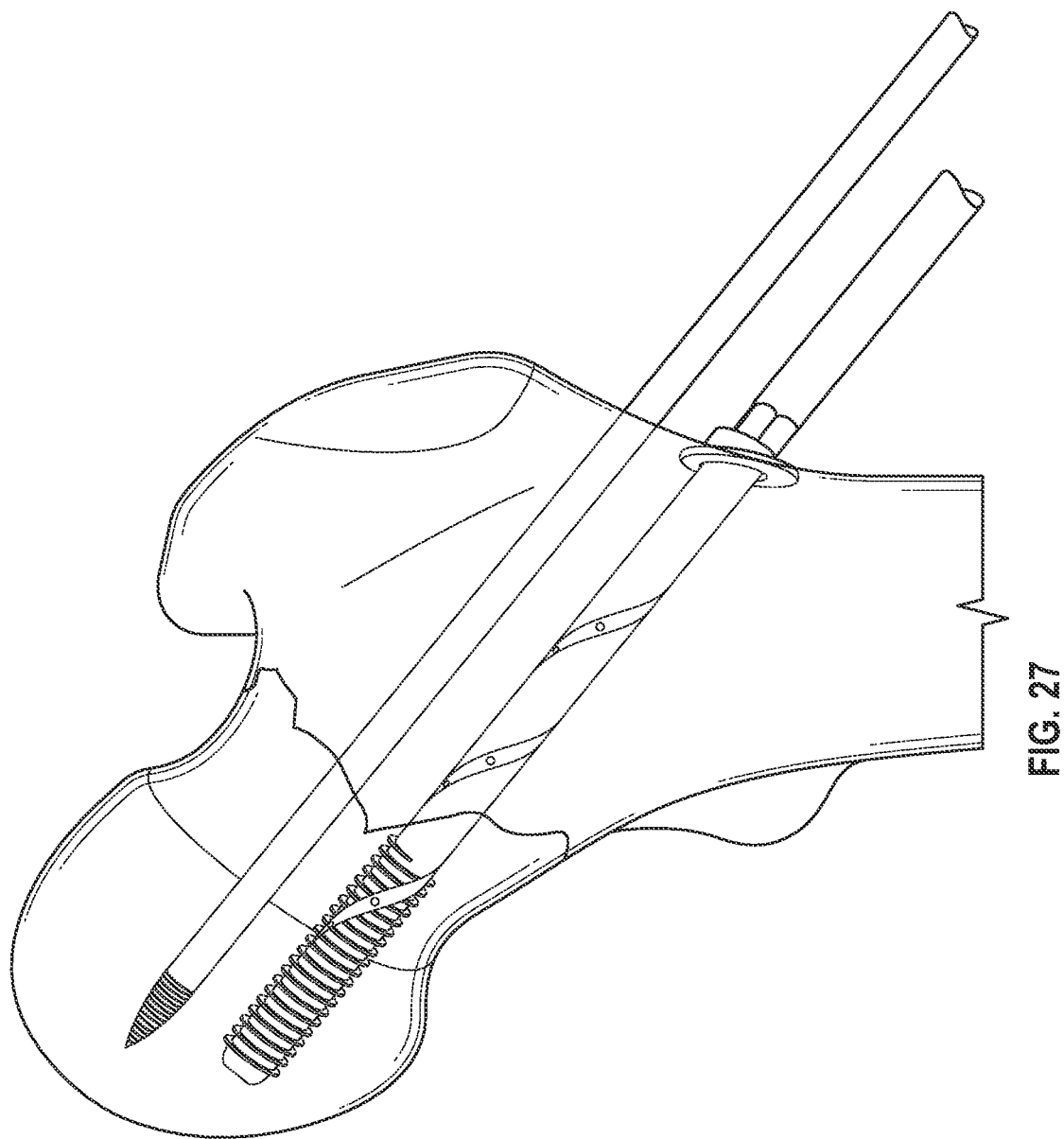
FIG. 27 is a graphic image showing a side view of the proximal femur of FIG. 26 after insertion of the cannulated bone screw. The femur is shown partially transparent for ease of illustrating the positioning of the cannulated bone screw and the guide wires.

A rotational driver (i.e., a cannulated screwdriver) is inserted into the screw head of a cannulated partially-threaded screw (i.e., a 7.3 mm N-FORCE FIXATION SYSTEM™ (InnoVision, Memphis, Tenn., USA) non-fenestrated screw) with an attached flat washer. The 7.3 mm cannulated partially-threaded screw is then inserted over the inferior guide wire (FIG. 26). The fracture is compressed manually by inserting the bone screw with the screwdriver. The inferior screw is a lag device and may induce compression to the fracture site for enhanced stability (FIG. 27).

Figure 28:
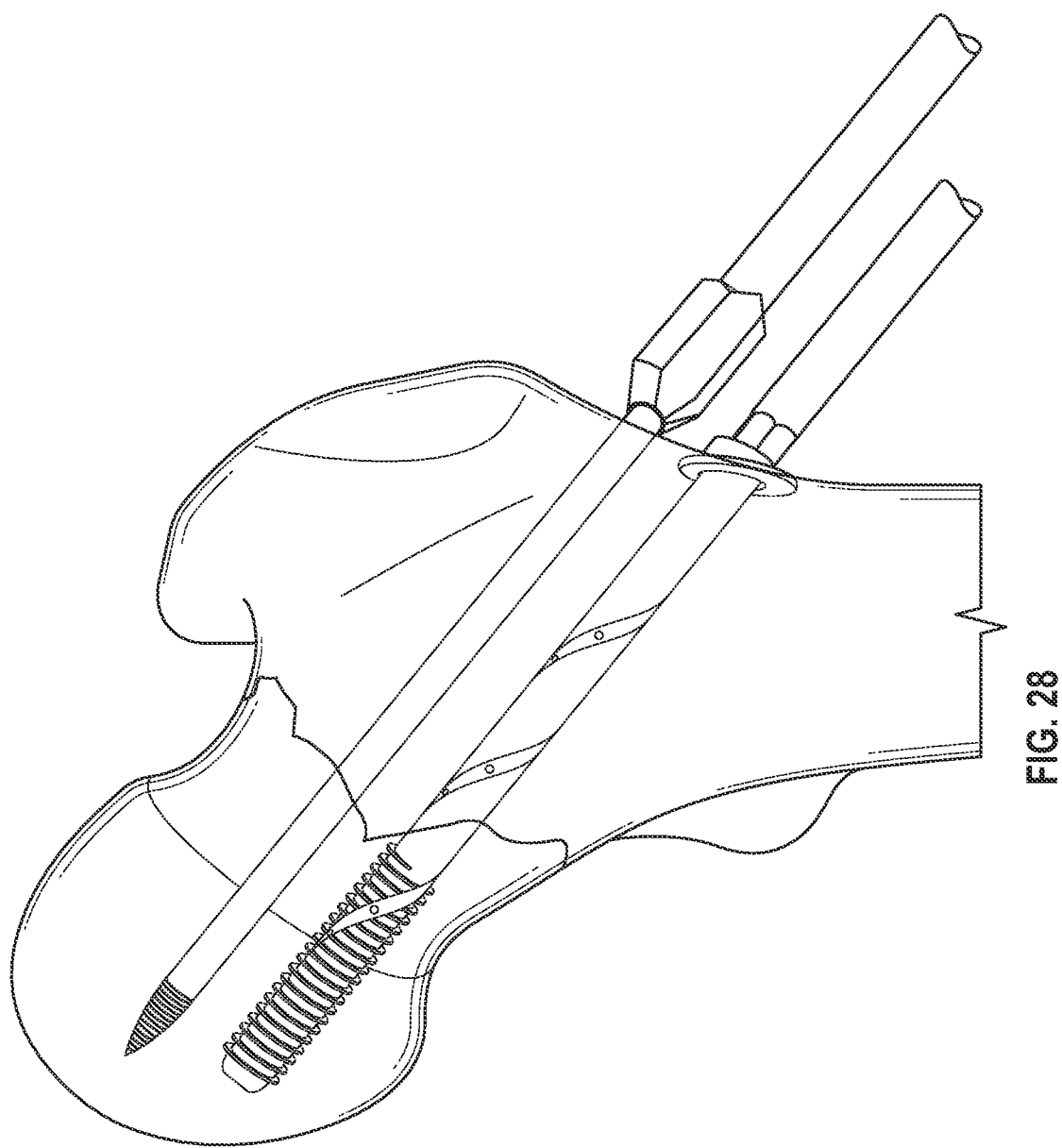
FIG. 28 is a graphic image showing a side view of the proximal femur showing a countersink drill bit inserted over a guide wire to prepare the bone for insertion of a cannulated and fenestrated bone screw. The femur is shown partially transparent for ease of illustrating the positioning of the cannulated bone screw and the guide wires.
Figure 29:
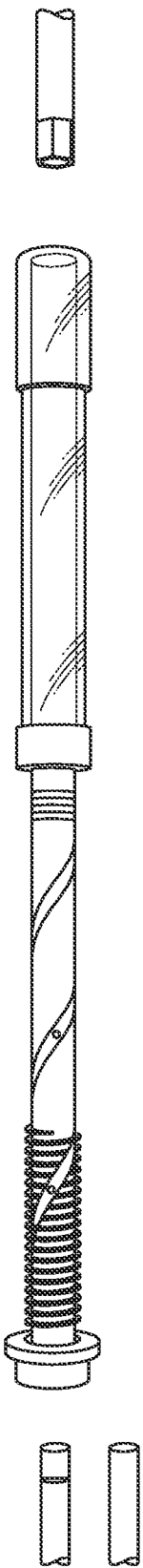
FIG. 29 is a graphic image showing (from left to right) a washer, a cannulated and fenestrated bone screw, a bone screw manifold, and a rotational driver prior to insertion of the bone screw over the guide wire and into the femur of FIG. 28.
Figure 30:
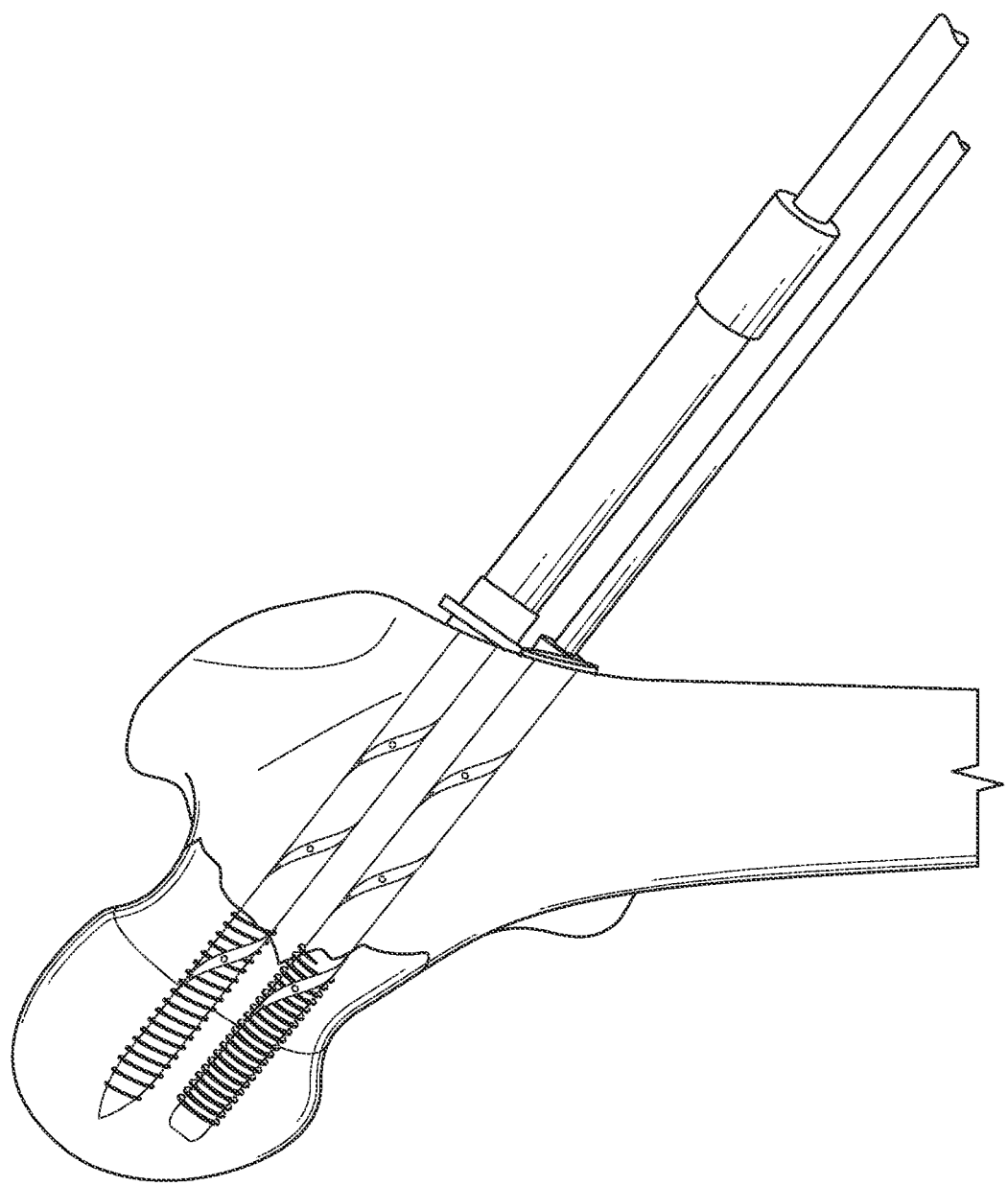
FIG. 30 is a graphic image showing a side view of the proximal femur after the cannulated and fenestrated bone screw of FIG. 29 has been inserted into the femur. The femur is shown partially transparent for ease of illustrating the positioning of the cannulated bone screw and the guide wires.

For the proximal two guide wires, a cannulated and fenestrated bone screw (e.g., a screw as described in U.S. Pat. No. 8,574,273 or PCT/US2014/020678, including a N-FORCE FIXATION SYSTEM™ (InnoVision, Memphis, Tenn. USA) cannulated and fenestrated bone screw) will be used with an inset washer for enhanced fixation and the ability to insert a flowable medium (e.g., bone cement) through the cannulated and fenestrated bone screw. The near cortex of the femur is overdrilled with a 7.3 mm countersink drill bit (FIG. 28). A cannulated and fenestrated bone screw (i.e. a N-FORCE FIXATION SYSTEM™ 7.3 mm fenestrated bone screw) is assembled to a proximal injection sheath (as described in U.S. Pat. No. 8,574,273 or PCT/US2014/020678) and a 7.3 mm inset washer is inserted over the screw with the expanded portion of the washer toward the head of the screw. A cannulated screwdriver is inserted through the sheath into the screw head (FIG. 29). The screw, inset washer, and sheath outer cannula is inserted into the femur over the 3.2 mm anterior guide wire until the washer contacts the lateral cortex of the femur (FIG. 30). The assembly is tightened snugly with hand force. This process may be repeated for the second anterior 3.2 mm guide wire (not shown).

Figure 31:
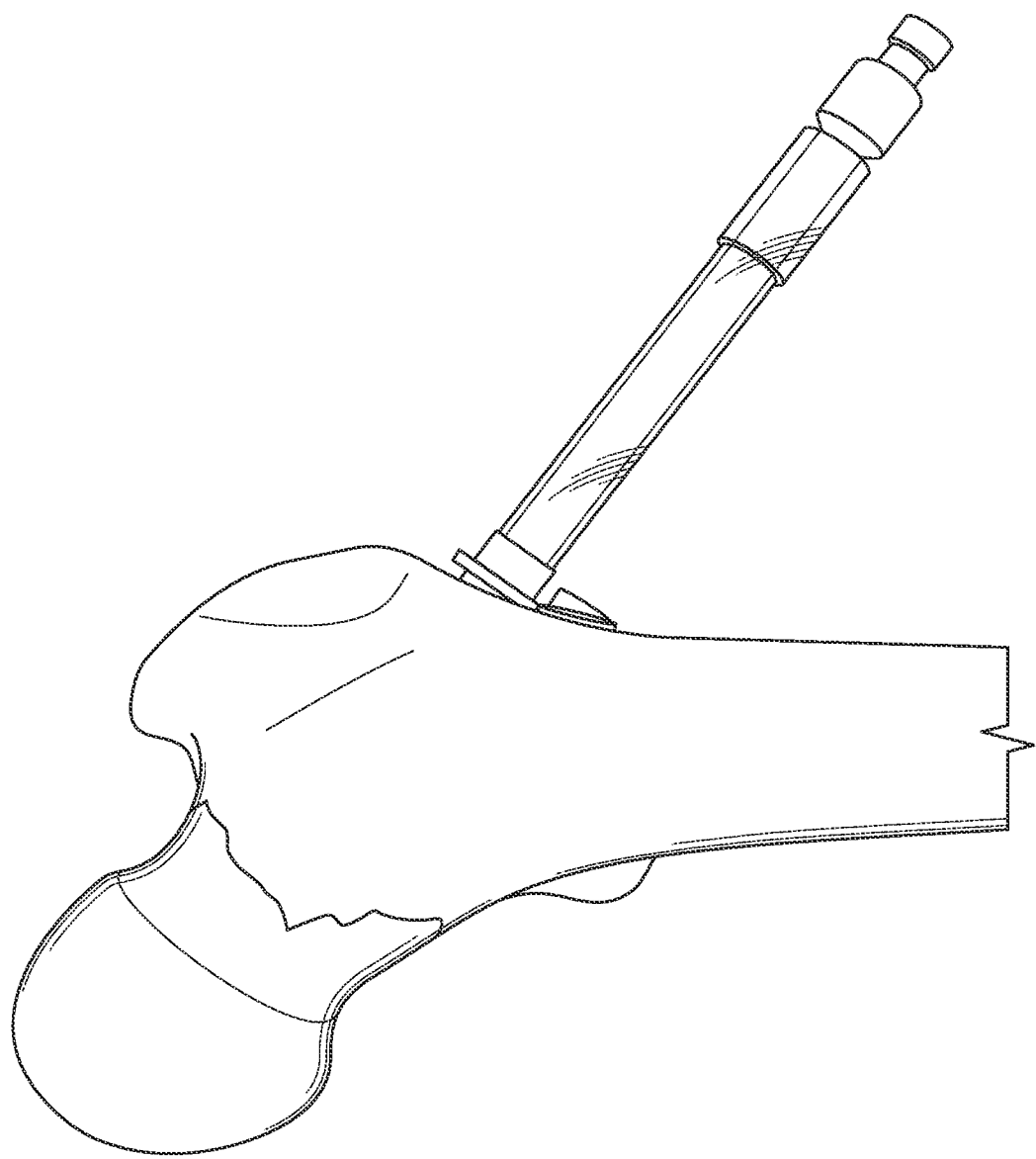
FIG. 31 is a graphic image showing a side view of the femur of FIG. 30 showing a bone screw manifold being prepared for injection of bone cement into the bone screw.
Figure 32:
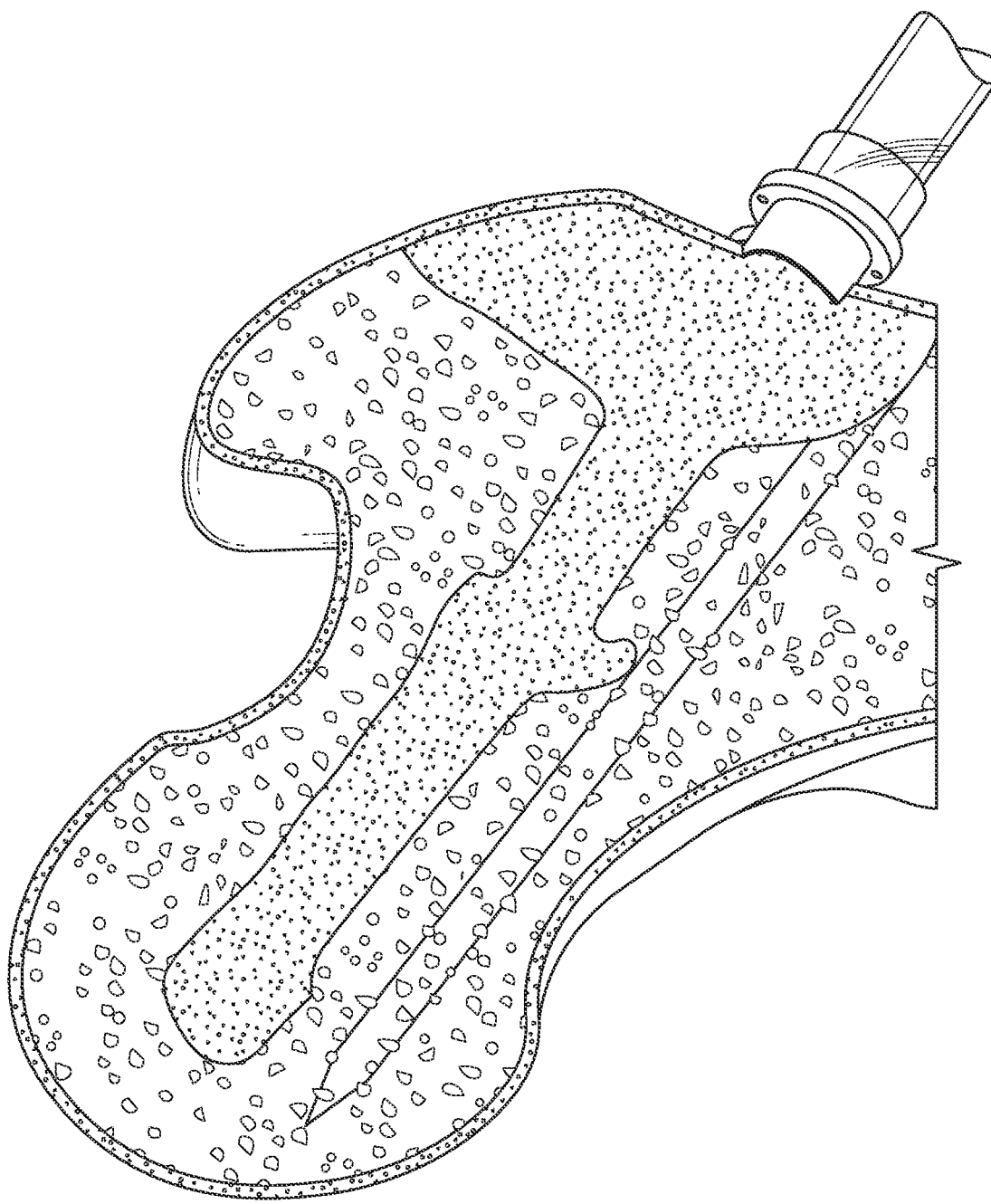
FIG. 32 is a graphic image showing a side sectional view of the proximal femur of FIG. 31. Shown in white is the circumferential augmentation of the upper bone screw by bone cement injected through the bone screw. This leads to formation of an internal buttress along the length of the screw and at the distal end of the screw near the head. The arrangement and positioning of bone screws to achieve this internal buttress is facilitated by the bone drill guide.
Figure 33:
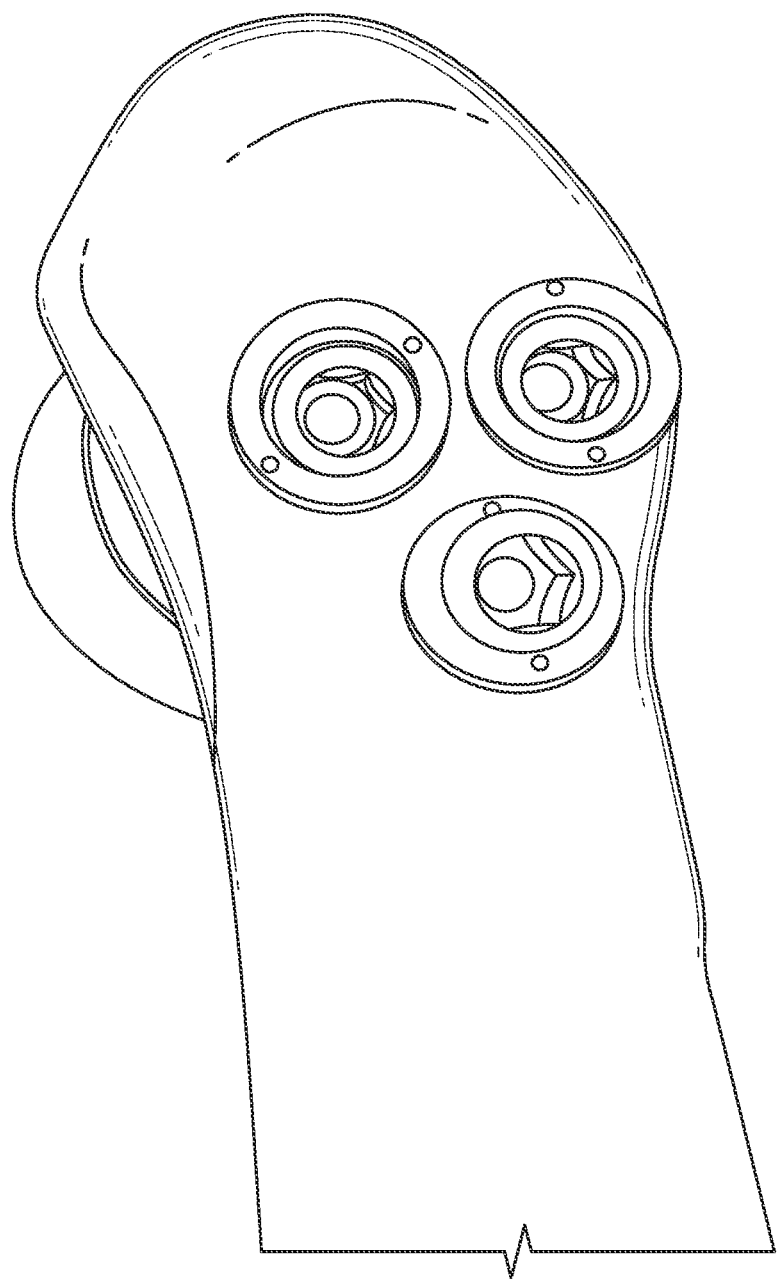
FIG. 33 is a graphic image showing a back view of the proximal femur showing washers and the heads of three bone screws which have been inserted into the femur using the bone drill guide.

The 3.2 mm guide wire is removed and an injector port for a Luer lock connection with the intended flowable medium is inserted into the proximal injection sheath (FIG. 31). Flowable medium may be injected into the bone through the cannulated and fenestrated bone screws. FIG. 32 shows a cross-section view of the flowable medium intrusion into the femoral proximal cancellous network of trabeculae. The coaxial alignment of screws allows the flowable medium to interact with all three screws within the bone. This circumferential augmentation can lead to formation of an internal buttress within the bone if bone cement is used. The sheaths are removed after injection of the flowable medium and the hand screwdriver is inserted into the head of the bone screw. Next, the interior injection sheaths are removed. This allows the operator to easily lock on the screw head with the screwdriver and complete the final tightening of the screws (FIG. 33). The outer sheaths will slide easily up the screw driver shaft to allow final tightening without loss of screwdriver engagement, in effect functioning as a self-retaining screwdriver component.

OTHER EMBODIMENTS

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

Other embodiments are in the claims.

What is claimed is:

1. A method for insertion of hardware into a bone comprising:
   positioning a bone drill guide in proximity to the bone using an arcuate element of the guide, wherein the guide comprises:
      a shaft having a proximal end and a distal end, wherein the arcuate element is attached to the distal end of the shaft and includes a distally-facing concave surface sized for seating on bone;
      a guide base attached to the proximal end of the shaft, wherein the guide base comprises at least two peripheral guide bores, wherein each of the peripheral guide bores is positioned about the shaft; and
      an interior channel extending through the guide base, the shaft, and the arcuate element; and
   inserting the hardware through the interior channel or through one of the peripheral guide bores of the guide and into the bone.

2. The method of claim 1, further comprising using X-ray or fluoroscopy to align the guide or the hardware with a position on the bone.

3. The method of claim 1, wherein the hardware includes at least one of a guide wire, a guide pin, an intramedullary nail, a fastener, a plate, an external fixation pin, or a drill bit.

4. The method of claim 1, wherein the hardware is inserted into the bone through the interior channel.

5. The method of claim 1, wherein inserting the hardware comprises inserting multiple pieces of hardware into the bone using the guide.

6. The method of claim 1, wherein inserting the hardware comprises inserting at least two pieces of hardware into the bone in a sequential manner, wherein a first piece of hardware is first inserted through the interior channel and into the bone and at least one subsequent piece of hardware is inserted through a first peripheral guide bore of the at least two peripheral guide bores and into the bone.

7. The method of claim 6, wherein the first piece of hardware and the at least one subsequent piece of hardware are guide wires.

8. The method of claim 7, wherein each of the guide wires is inserted to substantially the same depth into the bone.

9. The method of claim 7, further comprising:
   removing the guide; and
   overdrilling the guide wires using a cannulated drill bit.

10. The method of claim 9, further comprising inserting one or more bone screws into the bone along the guide wires.

11. The method of claim 10, wherein the bone screws are cannulated and fenestrated.

12. The method of claim 11, further comprising introducing a flowable medium into one of the one or more bone screws.

13. The method of claim 12, wherein the flowable medium includes at least one of a bone void filler, a bone cement, or a pharmaceutical agent.

14. The method of claim 1, wherein the method comprises repair of a bone defect in the bone.

15. The method of claim 14, wherein the bone defect is a fracture.

16. A method for insertion of hardware into a bone comprising:
   positioning a bone drill guide in proximity to the bone, wherein the guide comprises:
      a shaft including a proximal end, a distal end, and an interior channel extending from the proximal end to the distal end;

an arcuate bone-engaging element disposed at the distal end of the shaft, the arcuate bone-engaging element including a distally-facing concave surface sized for seating on bone; and a guide base disposed at the proximal end of the shaft and including a plurality of peripheral guide bores; and inserting the hardware through the interior channel or through one of the peripheral guide bores of the guide and into the bone.

17. The method of claim 16, wherein the hardware includes at least one of a guide wire, a guide pin, an intramedullary nail, a fastener, a plate, an external fixation pin, or a drill bit.

18. The method of claim 16, wherein inserting the hardware comprises inserting a first piece of hardware through the interior channel and inserting a second piece of hardware through one of the peripheral guide bores.

19. A method for treating a defect in a bone comprising:
positioning a bone drill guide in proximity to the bone, wherein the guide comprises:
a shaft including a proximal end, a distal end, and an interior channel extending from the proximal end to the distal end;
a bone-engaging element disposed at the distal end of the shaft and sized for seating on bone; and
a guide base disposed at the proximal end of the shaft and including a plurality of peripheral guide bores;
engaging a distally-facing concave surface of the bone-engaging element with the bone;
inserting a guide wire through the interior channel or through one of the peripheral guide bores of the guide and into the bone;
removing the guide; and
inserting a fastener along the guide wire and into the bone.

* * * * *